(12) United States Patent
Sengupta et al.

(10) Patent No.: US 11,701,429 B2
(45) Date of Patent: Jul. 18, 2023

(54) TARGETED DRUG DELIVERY THROUGH AFFINITY BASED LINKERS

(71) Applicant: AKAMARA THERAPEUTICS, INC., Philadelphia, PA (US)

(72) Inventors: Shiladitya Sengupta, Waltham, MA (US); Monideepa Roy, Delhi (IN); Nimish Gupta, Delhi (IN); Seikh Samad Hossain, Delhi (IN)

(73) Assignee: AKAMARA THERAPEUTICS, INC., Philadelphia, PA (US)

( * ) Notice: Subject to any disclaimer, the term of this patent is extended or adjusted under 35 U.S.C. 154(b) by 215 days.

(21) Appl. No.: 16/736,495

(22) Filed: Jan. 7, 2020

(65) Prior Publication Data
US 2020/0199249 A1    Jun. 25, 2020

Related U.S. Application Data

(62) Division of application No. 15/124,058, filed as application No. PCT/US2015/019960 on Mar. 11, 2015, now Pat. No. 10,533,059.

(30) Foreign Application Priority Data

Mar. 12, 2014   (IN) .......................... 00732/DEL/2014

(51) Int. Cl.
| | |
|---|---|
| *A61K 39/00* | (2006.01) |
| *A61K 47/68* | (2017.01) |
| *C07K 16/28* | (2006.01) |
| *C07K 16/32* | (2006.01) |

(52) U.S. Cl.
CPC ...... *A61K 47/6851* (2017.08); *A61K 47/6803* (2017.08); *A61K 47/6849* (2017.08); *A61K 47/6889* (2017.08); *C07K 16/2863* (2013.01); *C07K 16/32* (2013.01); *C07K 2317/52* (2013.01); *C07K 2317/73* (2013.01)

(58) Field of Classification Search
CPC ............ A61K 47/6803; A61K 47/6849; A61K 47/6889; C07K 16/2863; C07K 16/32; C07K 2317/52; C07K 2317/73
See application file for complete search history.

(56) References Cited

U.S. PATENT DOCUMENTS

| | | |
|---|---|---|
| 5,420,105 A | 5/1995 | Gustavson et al. |
| 6,218,367 B1 | 4/2001 | Jacob |
| 2005/0118164 A1 | 6/2005 | Herman |
| 2005/0271673 A1 | 12/2005 | Wilbur et al. |
| 2009/0068169 A1 | 3/2009 | Penney et al. |
| 2011/0286971 A1 | 11/2011 | Yacoby et al. |
| 2011/0312877 A1 | 12/2011 | Beringer et al. |

FOREIGN PATENT DOCUMENTS

| | | |
|---|---|---|
| EP | 2093287 A1 | 8/2009 |
| WO | 1998/19705 A1 | 5/1998 |
| WO | 2004/045642 A1 | 6/2004 |
| WO | 2005/113012 A2 | 12/2005 |
| WO | WO2005113012 | * 12/2005 |
| WO | WO20090138714 | * 11/2009 |
| WO | 2014/001326 A1 | 1/2014 |

OTHER PUBLICATIONS

King et al (Bioconjugate Chem 10:279-288, 1999. (Year: 1999).*
Chari R., "Targeted Cancer Therapy: Conferring Specificity to Cytotoxic Drugs", Accounts of Chemical Research 41 (1):98-107 (2008).
Kang et al., "Developing an antibody-binding protein cage as a molecular recognition drug modular nanoplatform", Biomaterials 33:5423-5430 (2012).
Lin et al., "Molecular Insight into the Ligand-IgG Interactions for 4-Mercaptoethyl-pyridine Based Hydrophobic Charge-Induction Chromatography", The Journal of Physical Chemistry B 116:1393-1400 (2012).
Lin et al., "Molecular mechanism of hydrophobic charge-induction chromatography: Interactions between the immobilized 4-mercaptoethyl-pyridine ligand and IgG", Journal of Chromatography A 1260:143-153 (2012).
Zong et al., "Bifunctional PAMAM Dendrimer Conjugates of Folic Acid and Methotrexate with Defined Ratio", Biomacromolecules 13:982-991 (2012).

* cited by examiner

*Primary Examiner* — Lei Yao
(74) *Attorney, Agent, or Firm* — Nixon Peabody LLP; David S. Resnick; Ravinderjit S. Braich

(57) ABSTRACT

The current invention describes a conjugate of a targeting moiety linked to a drug via a molecule having high affinity for the targeting moiety at physiological pH such that the drug releases at low pH from the targeting moiety.

4 Claims, 25 Drawing Sheets

TARGETED DRUG DELIVERY THROUGH AFFINITY BASED LINKERS

CROSS-REFERENCE TO RELATED APPLICATION

This application is a divisional of U.S. Ser. No. 15/124,058 filed Sep. 7, 2016, now U.S. Pat. No. 10,533,059 issued Jan. 14, 2020, which is a 371 National Phase Entry of International Patent Application No. PCT/US15/19960 filed on Mar. 11, 2015, which claims benefit under 35 U.S.C. § 119(a)-119(d) of Indian Patent Application No. 0732/DEL/2014, filed Mar. 12, 2014, the contents of which are incorporated herein by reference in their entireties.

TECHNICAL FIELD

The present invention relates to targeted drug delivery compositions and methods of making and use thereof.

BACKGROUND

One of the major limitations in therapy today is the toxicity or side effect of drugs. The maximum tolerated dose of a drug can thus be a hindrance for many therapies including those for cancer. There is a need for conjugates that specifically bind to a disease specific target and release the drug at the disease site. Targeted drug delivery using antibodies, for example, has been investigated extensively (R. V. J. Chari, "Targeted cancer therapy: conferring specificity to cytotoxic drugs," *Accounts of chemical research*, vol. 41, no. 1, pp. 98-107, January 2008). There are currently two antibody drug conjugates (ADCs) on the market for cancer therapy namely KADCYLA™ and ADCETRIS™. They both use a cytotoxic drug covalently conjugated to an antibody through a cleavable linker.

Protein A is a small bacterial protein that has an affinity for the Fc region of IgG class of antibodies (T. Moks, L. Abrahmsén, B. Nilsson, U. Hellman, J. Sjöquist, and M. Uhlén, "Staphylococcal protein A consists of five IgG-binding domains," *European journal of biochemistry/FEBS*, vol. 156, no. 3, pp. 637-43, May 1986). The domain that non-covalently binds to the Fc region is already known and is used for monoclonal antibody chromatographic purification extensively (S. Hober, K. Nord, and M. Linhult, "Protein A chromatography for antibody purification," *Journal of chromatography. B, Analytical technologies in the biomedical and life sciences*, vol. 848, no. 1, pp. 40-7, March 2007). Several protein A mimetics and small molecules have been explored in the past to replace protein A chromatography such as triazines, 4-mercaptoethyl pyridine (4-MEP), peptides (V S. Kabir, "Immunoglobulin purification by affinity chromatography using protein A mimetic ligands prepared by combinatorial chemical synthesis," *Immunological investigations*, vol. 31, no. 3-4, pp. 263-78, 2002) etc. They all have affinity for the Fc region similar to protein A but each offering some advantage over the conventional protein A (S. Ghose, B. Hubbard, and S. M. Cramer, "Evaluation and comparison of alternatives to Protein A chromatography Mimetic and hydrophobic charge induction chromatographic stationary phases," *Journal of chromatography. A*, vol. 1122, no. 1-2, pp. 144-52, July 2006). 4-MEP and triazines have also been investigated for treatment of autoimmune diseases (J. Ren, L. Jia, L. Xu, X. Lin, Z. Pi, and J. Xie, "Removal of autoantibodies by 4-mercaptoethylpyridine-based adsorbent," *Journal of chromatography. B, Analytical technologies in the biomedical and life sciences*, vol. 877, no. 11-12, pp. 1200-4, April 2009 and B. Zacharie, S. D. Abbott, J.-F. Bienvenu, A. D. Cameron, J. Cloutier, J.-S. Duceppe, A. Ezzitouni, D. Fortin, K. Houde, C. Lauzon, N. Moreau, V. Perron, N. Wilb, M. Asselin, A. Doucet, M.-E. Fafard, D. Gaudreau, B. Grouix, F. Sarra-Bournet, N. St-Amant, L. Gagnon, and C. L. Penney, "2,4,6-Trisubstituted Triazines As Protein a Mimetics for the Treatment of Autoimmune Diseases," *Journal of medicinal chemistry*, vol. 53, no. 3, pp. 1138-45, February 2010).

Some of the peptides, owing to their affinity for the antibody, have also been used for targeting nanoparticles for drug delivery (H. J. Kang, Y. J. Kang, Y.-M. Lee, H.-H. Shin, S. J. Chung, and S. Kang, "Developing an antibody-binding protein cage as a molecular recognition drug modular nanoplatform," *Biomaterials*, vol. 33, no. 21, pp. 5423-30, July 2012 and US Patent Publication No. 2011/0312877, and European Patent Application No. EP 2 093 287 A1). The targeting antibody directs the nanoparticles in close proximity to the target site wherein the nanoparticle can deliver its cargo. Non-covalent interactions between the linker and drug have been employed to conserve the activity of the drug U.S. Pat. No. 5,420,105. Biotin labelling of biomolecules has been reported for affinity-based diagnostics (US 2001/0023288 A1) wherein the affinity of biotin towards streptadivin is employed.

The binding site on IgG of the different affinity molecules has been found to be different from each other. Binding site for 4-MEP on IgG Fc has been computationally determined previously (Lin, D.-Q., Tong, H., Wang, H. & Yao, S. Molecular insight into the ligand-IgG interactions for 4-mercaptoethyl-pyridine based hydrophobic charge-induction chromatography. *J. Phys. Chem. B* 116, 1393-400 (2012).) Binding site of traizine on IgG Fc has also been similarly determined computationally (Branco, R. J. F., Dias, A. M. G. C. & Roque, A. C. A. Understanding the molecular recognition between antibody fragments and protein A biomimetic ligand. *J. Chromatogr. A* 1244, 106-15 (2012)).

SUMMARY

The current invention discloses targeted drug delivery conjugates comprising a targeting moiety linked to a drug via a molecule having an affinity for the targeting moiety.

A targeted drug delivery system is described. The targeting moiety could be an antibody, antibody fragment or any other molecule that specifically recognizes a target. The antibody is linked to a molecule which has an affinity for it. This molecule, the affinity ligand, for example, could be 4-mercaptoethyl pyridine or triazines or peptides. These molecules non-covalently bind to the conserved Fc region of the antibody with high affinity at physiological pH in a specific manner. In case of low affinity molecules, the bond can be strengthened by cross linking using covalent linkages. The covalent linkages could be through click-chemistry, photo-crosslinking etc.

The affinity ligand is further covalently or non-covalently linked to a drug or therapeutic agent. The drug can be modified to make it more soluble and so that it cleaves from the linking molecule at the target site. As an example for cancer therapy, after administering the conjugate in the bloodstream of the patient, the mechanism of action will involve the targeting moiety binding to the specific antiligand on the cancer cell, internalization of the entire conjugate through receptor-mediated endocytosis, disruption of the linkage between the affinity ligand and the targeting moiety at low pH in the endosome, cleavage of the drug from the linking molecule, if needed, and the drug translocating to the site of action.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 shows an antibody linked non-covalently to an affinity ligand which is linked covalently to a drug. FIG. 2 shows an antibody linked non-covalently to an affinity ligand which is linked covalently to a drug via a spacer. FIG. 3 shows an antibody linked non-covalently to an affinity ligand which is linked covalently to a drug via a cleavable linker. FIG. 4 shows an antibody linked non-covalently to an affinity ligand which is linked covalently to a drug via a spacer and a cleavable linker (like peptide bonds, ester linkage etc.). FIG. 5 shows an antibody linked non-covalently to MEP affinity ligand which is linked via a linker to a drug.

FIG. 6 (2.1) shows an antibody non-covalently linked with 4-MEP which is linked to a drug via a cleavable peptide linker. FIG. 7 (2.2) shows an antibody non-covalently linked with 4-MEP which is linked to a drug via a cyclodextrin-polyethylene glycol (PEG) linker. FIG. 8 (2.3) shows 4-MEP which is linked to a cytotoxic drug, camptothecin, via a PEG spacer and cleavable peptide linker. FIG. 9 (2.4) shows 4-MEP linked to two drug molecules using a branched linker with each branch comprising a PEG/peptide spacer. FIG. 10 (2.5) shows 4-MEP linked to two drug molecules using a branched cleavable peptide linker, wherein each branch comprises a PEG/peptide spacer. FIG. 11 (2.6) shows 4-MEP linked to two drug molecules using a branched cleavable peptide linker, wherein the drug is linked via an ester linkage in each branch. FIG. 12 (2.7) shows 4-MEP linked to DACH-Pt (cytotoxic drug) via a PEG spacer. FIG. 13 (2.8) shows a Triazine molecule linked with a drug. The heterocyclic compound in the rectangle can interact with antibody/other targeting moiety and any cytotoxic drug can be attached to it through a suitable linker. FIG. 14 (2.9) shows Fc-III (a cyclic peptide) linked to a drug. FIG. 15 (2.10) shows an antibody linked through 4-MEP to a drug via a hydrocarbon spacer and carboxylate linkage. FIG. 16 (2.11) shows an antibody linked through 4-MEP to a drug via a hydrocarbon spacer and peptide linkage. FIG. 17 (2.12) shows an antibody linked through 4-MEP to a drug via a hydrocarbon spacer and carbamate linkage. FIG. 18 (2.13) shows an antibody linked through 4-MEP to a drug directly via the thiol group. FIG. 19 (2.14) shows an antibody linked through 4-MEP to a drug via a peptide linker and an ester bond. FIG. 20 (2.15) shows a triazine molecule linked to a drug via a dipeptide and an ester bond.

FIG. 38A shows a profile of anti-EGFR antibody obtained at 280 nm with PDA detector. FIG. 38B shows a profile of anti-EGFR antibody obtained at 430 nm ($\lambda_{em}$) with fluorescence detector. FIG. 38C shows a profile of ADC with 2.18 conjugated to anti-EGFR antibody obtained at 280 nm with PDA detector. FIG. 38D shows a profile of ADC with 2.18 conjugated to anti-EGFR antibody obtained at 430 nm ($\lambda_{em}$) with fluorescence detector.

DETAILED DESCRIPTION

Figure 1:
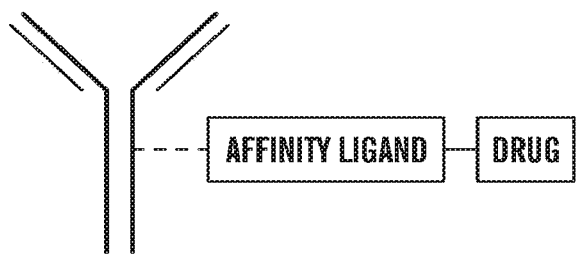
FIGS. 1-5 are schematic representations of targeted drug delivery conjugates according to some embodiments of the invention.
Figure 2:
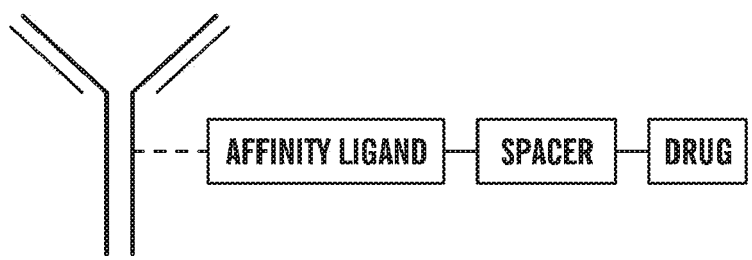
Figure 3:
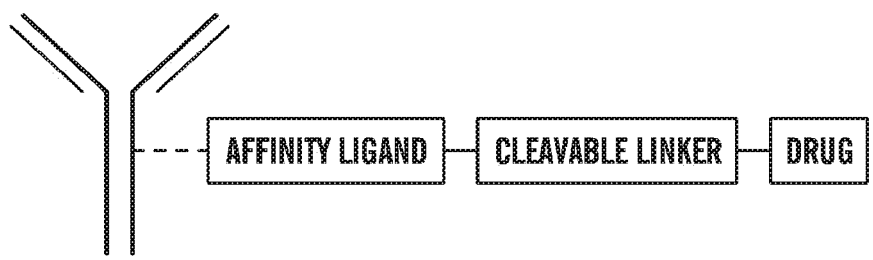
Figure 4:
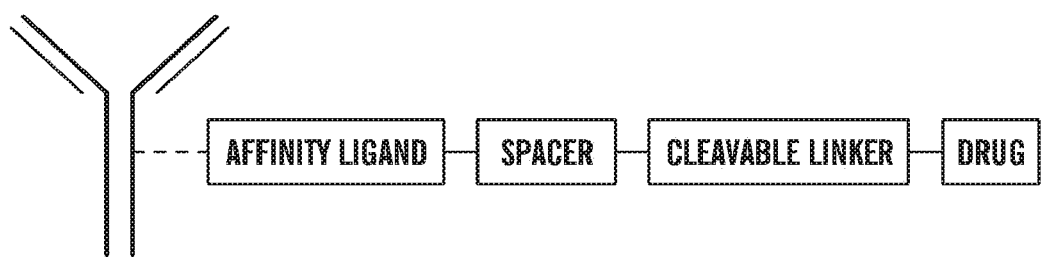
Figure 5:
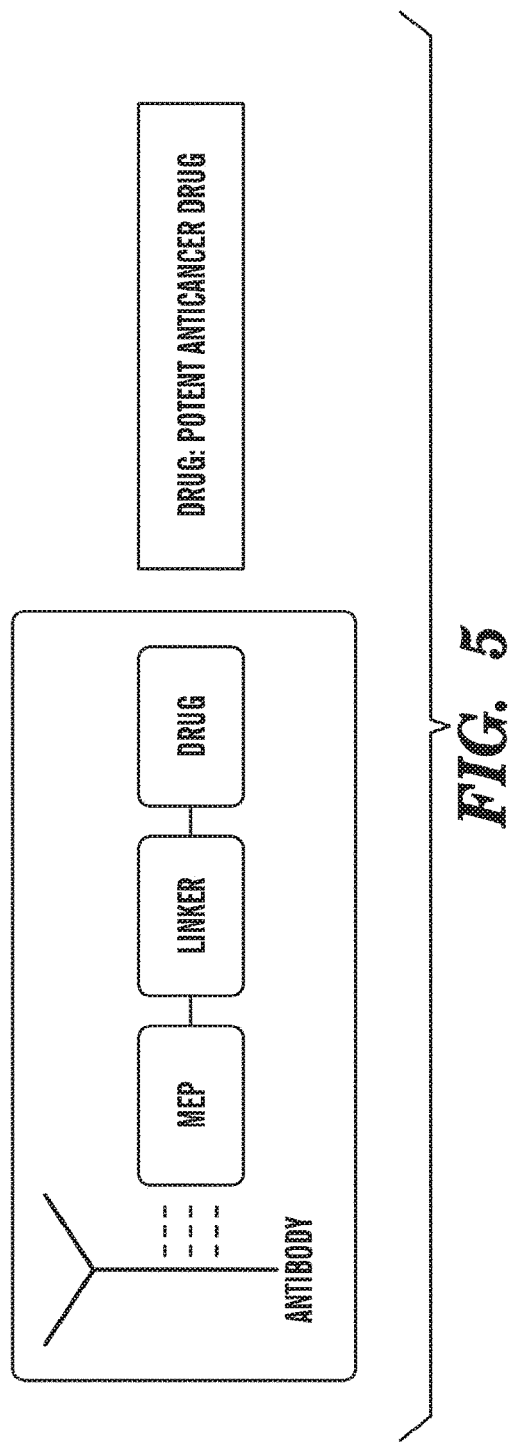
Figure 6:
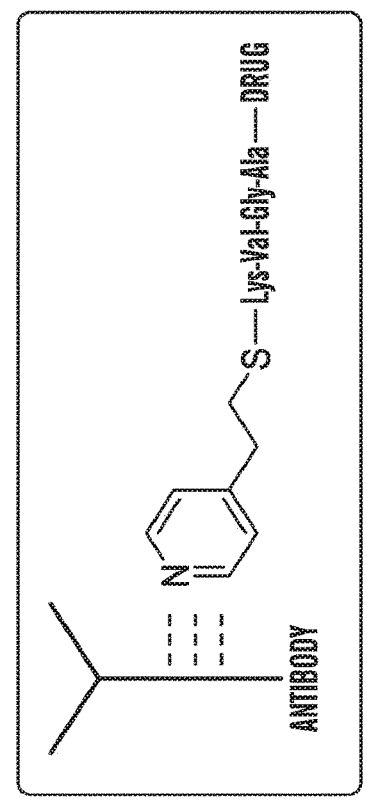
FIGS. 6-20 show exemplary targeted drug delivery conjugates according to some embodiments of the invention.
Figure 7:
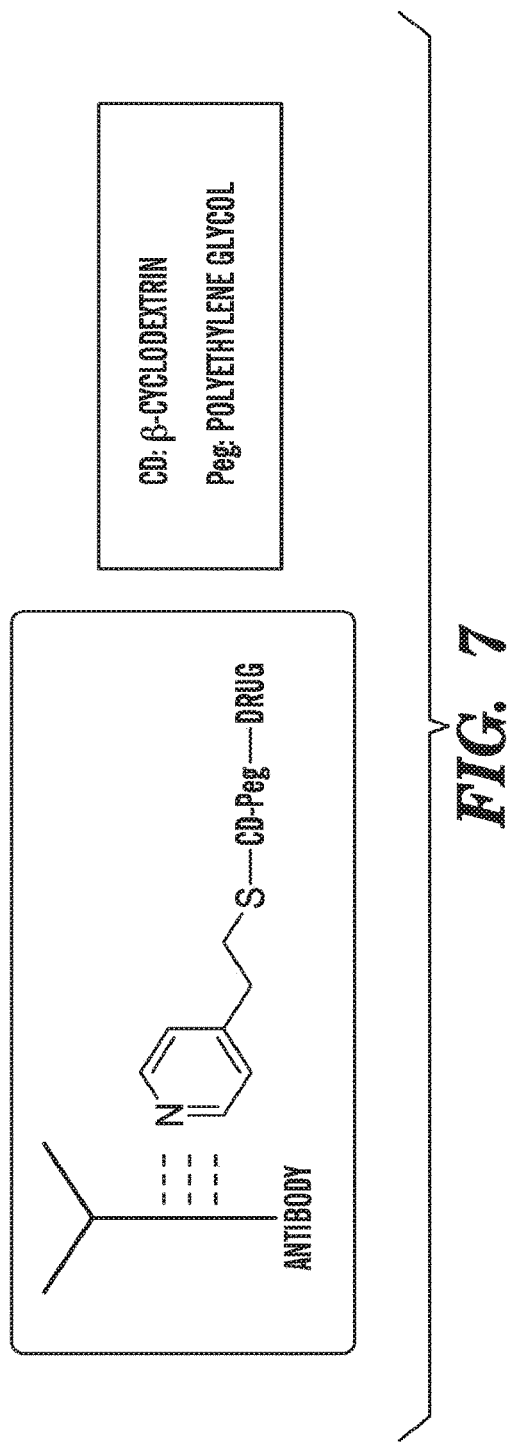
Figure 8:
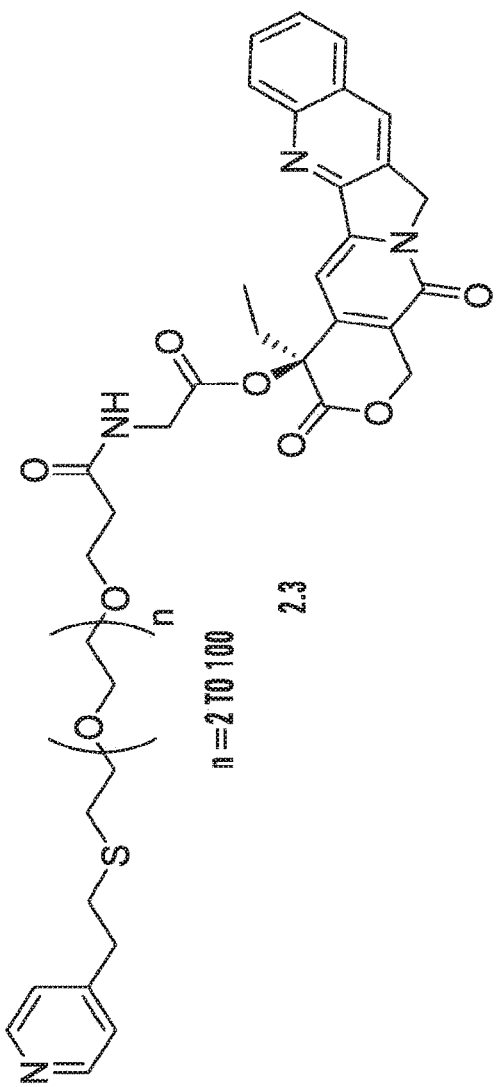
Figure 9:
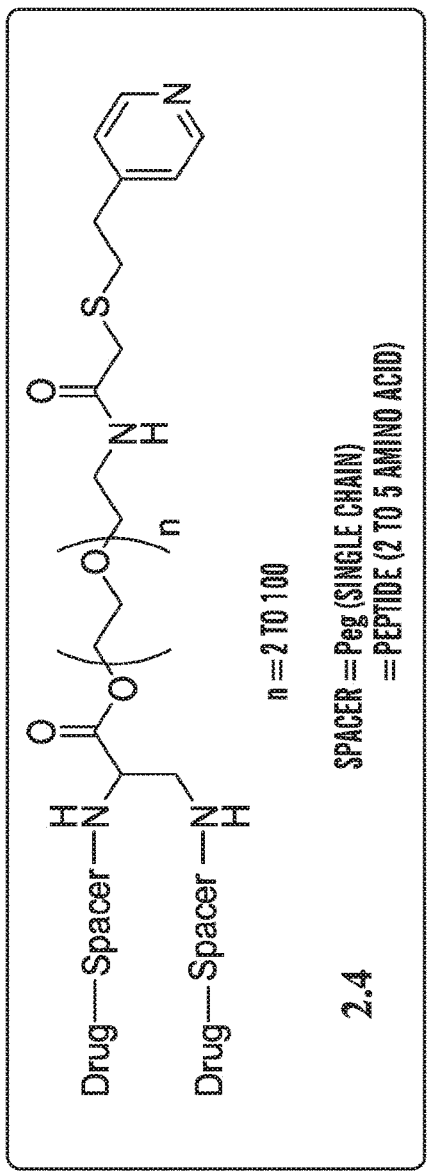
Figure 10:
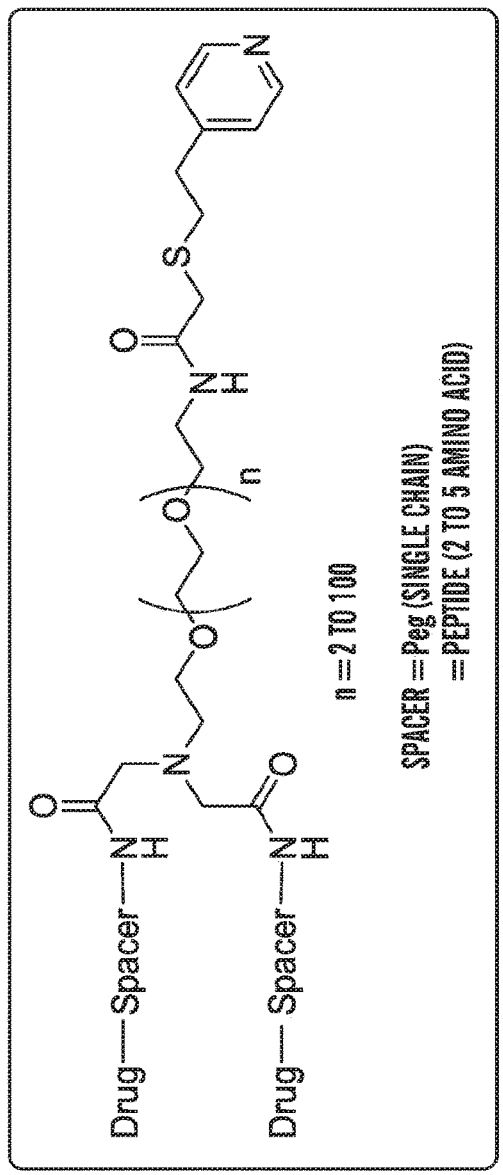
Figure 11:
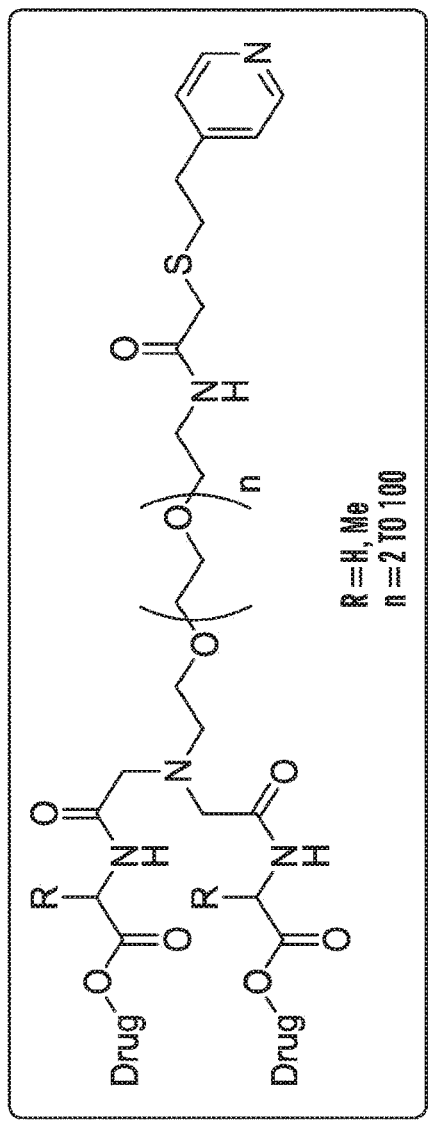
Figure 12:
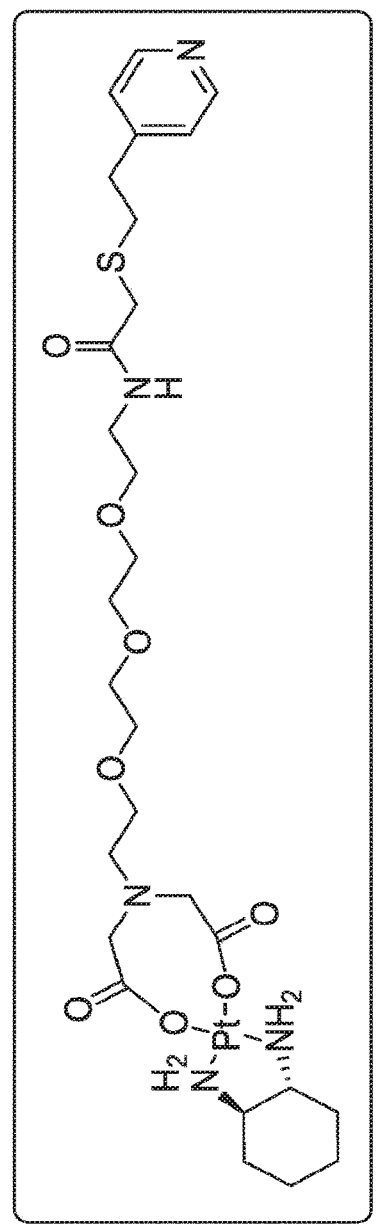
Figure 13:
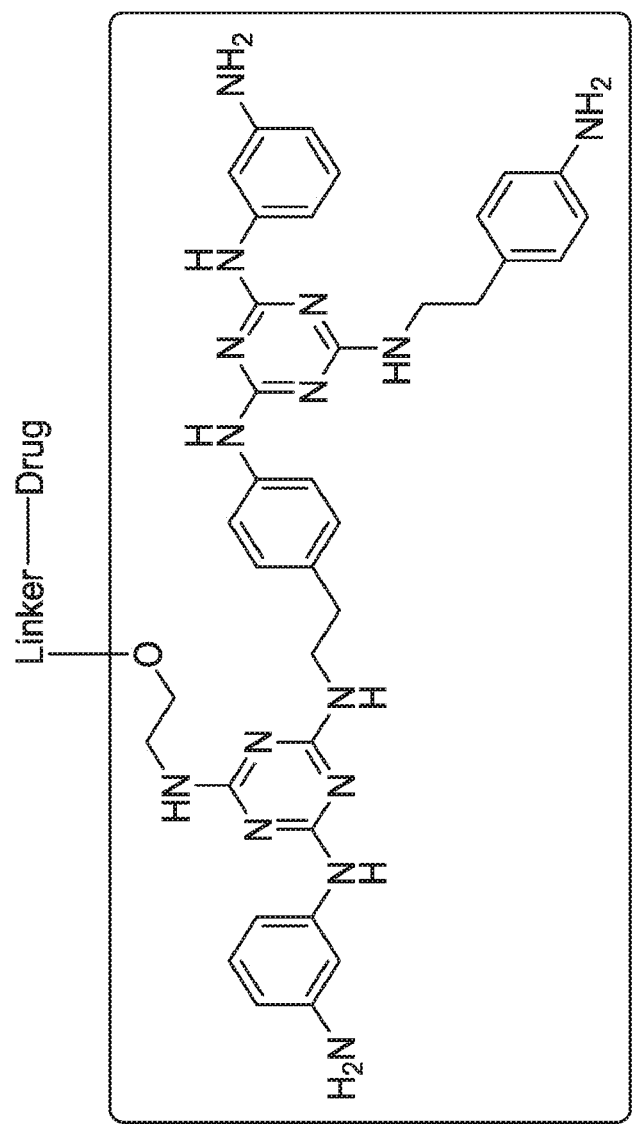
Figure 14:
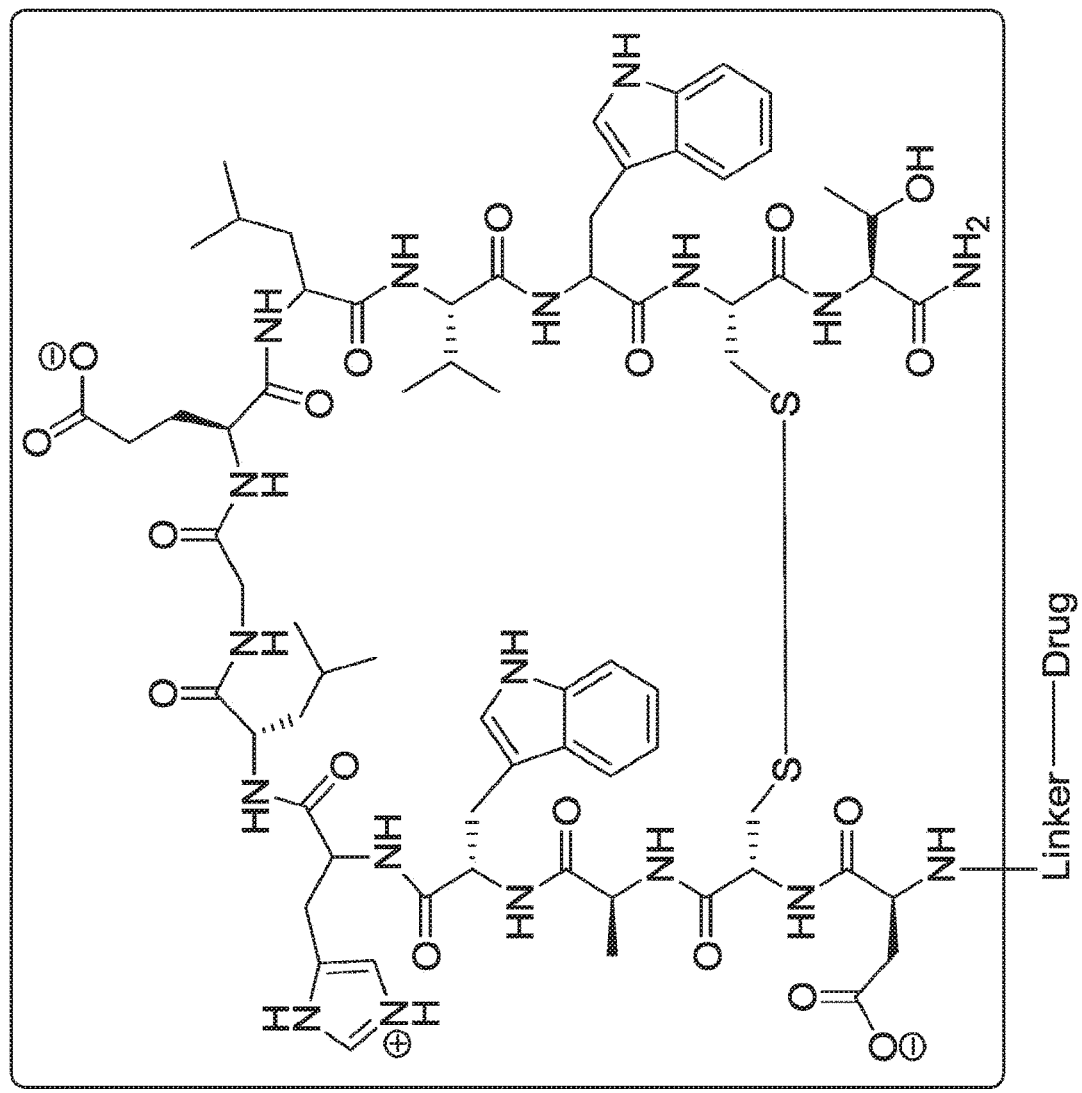
Figure 15:
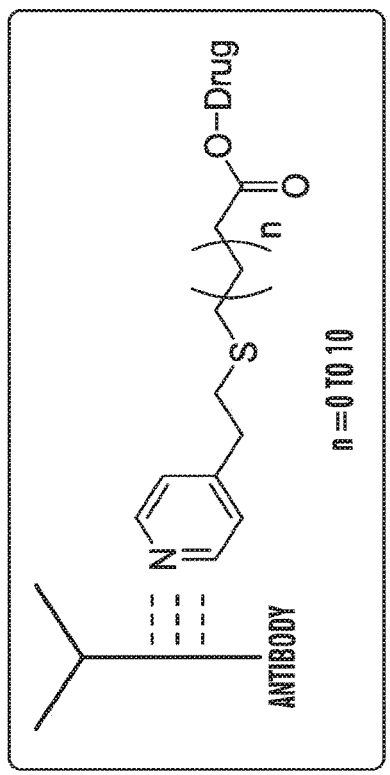
Figure 16:
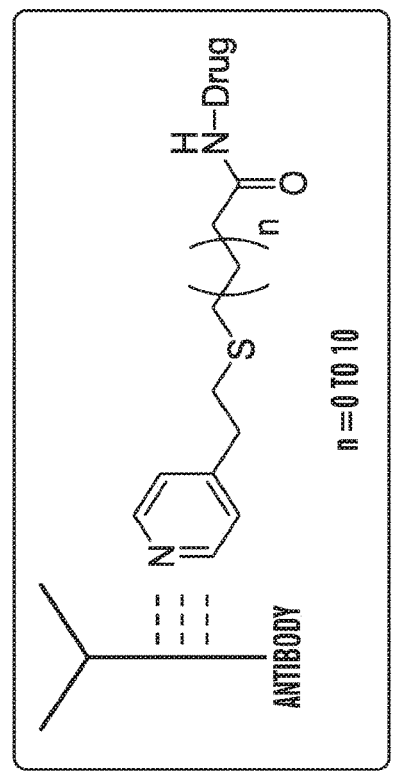
Figure 17:
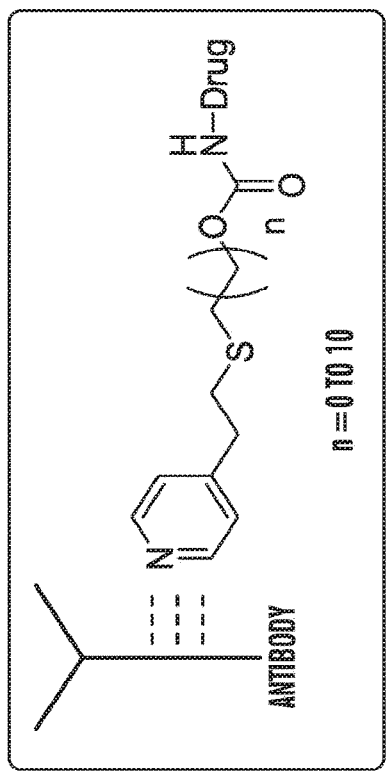
Figure 18:
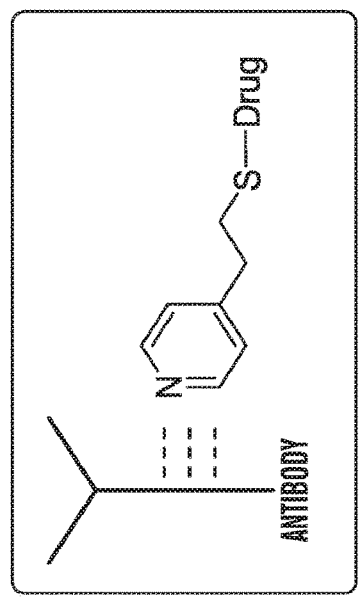

The present invention is directed to targeted drug delivery conjugates. Typically, the conjugate comprises a targeting ligand and a molecule of interest, e.g., a therapeutic agent. The targeting ligand and the molecule of interest are linked to each other via an affinity ligand.

As used herein the term "targeting moiety" or "targeting ligand" refers to any molecule that provides an enhanced affinity for a selected target, e.g., a cell, cell type, tissue, organ, region of the body, or a compartment, e.g., a cellular, tissue or organ compartment. The targeting moiety or ligand can comprise a wide variety of entities. Such ligands can include naturally occurring molecules, or recombinant or synthetic molecules.

Exemplary targeting ligands include, but are not limited to, antibodies, antigen binding fragments of antibodies, antigens, folates, EGF, albumin, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Additional exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 2-50 amino acids long, e.g., about 5, 10, 15, 20, 25, 30, 35, 40, 45, or 50 amino acids long.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-glucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,552,545; 6,335,434 and 7,128,893, contents of all of which are herein incorporated in their entireties by reference.

In some embodiments, the targeting ligand binds a protein, receptor, or marker expressed on the surface of a cancer cell.

In some embodiments, the targeting ligand binds EGFR.

In some embodiments, the targeting ligand is a polyclonal or monoclonal antibody or a fragment thereof retaining epitope binding activity or an antibody-based binding moiety.

In some embodiments, the targeting ligand is a polyclonal or monoclonal antibody, antibody fragments, a peptide, or a molecule that is capable of binding protein receptors expressed on the surface of cancer cells.

In some embodiments, the targeting ligand is an antibody selected from the group consisting of C242 antibody (CanAg), Rituximab (CD20), Trastuzumab (Her2), Cetuximab (EGFR), Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope binding fragments thereof and any combinations thereof.

As used herein, the term "affinity moiety" or "affinity ligand" refers to any molecule that binds to a targeting ligand. Generally, the affinity ligand binds with the targeting ligand at a site that does not inhibit or reduce binding of the targeting ligand to its target. According to one embodiment of the invention, the affinity ligand binds with to the targeting ligand non-covalently. Non-covalent interactions include, but are not limited to, hydrophobic interactions, ionic interactions, hydrogen bonding, van der Waals interactions, dipole-dipole interactions, electrostatic interactions, shape recognition interactions, ionic charge complex formation, π-π interactions, and host guest interaction (e.g., cyclodextrin/adamantine). Thus, the affinity ligand can be any molecule able to bind to the targeting moiety non-covalently, specifically and at definite sites on the targeting moiety with high affinity.

In some embodiments, the affinity ligand binds with the targeting ligand with high affinity. As used herein, the term "high affinity" means that the affinity ligand binds to the targeting ligand with a higher affinity than to a reference molecule or ligand. In some embodiments, the affinity ligand binds specifically to the targeting ligand, i.e., binds to such a targeting ligand more readily than it would bind to an unrelated, or random targeting ligand or competitively inhibits binding of a reference affinity ligand which itself binds specifically or preferentially to the target molecule. Generally, the term "specifically binds" or the like, means that the affinity ligand forms a complex with the targeting ligand that is relatively stable under physiologic conditions. Specific binding can be characterized by an equilibrium dissociation constant of at least about $1 \times 10^{-4}$ M or less (e.g., a smaller $K_d$ denotes a tighter binding). Methods for determining whether two molecules specifically bind are well known in the art and include, for example, equilibrium dialysis, surface plasmon resonance, and the like. An affinity ligand that specifically binds a particular targeting ligand may, however, exhibit cross-reactivity to other targeting ligands. Moreover, multi-specific affinity ligands (e.g., bispecifics) that bind to two or more different targeting ligands are nonetheless considered affinity ligands that "specifically bind" to the targeting ligand, as used herein.

It should be noted that the affinity or binding can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66), and can be calculated using, e.g., a dissociation constant, $K_d$, such that a lower $K_d$ reflects a higher affinity.

The affinity can be characterized by a dissociation constant $K_d$ of about $10^{-6}$ M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10}$ M, about $5 \times 10^{-11}$ M, about $10^{-11}$ M, about $5 \times 10^{-12}$ M, about $10^{-12}$ M, about $5 \times 10^{-13}$ M, about $10^{-13}$ M, about $5 \times 10^{-14}$ M, about $10^{-14}$ M, about $5 \times 10^{-15}$ M, or about $10^{-15}$ M or lower.

As used in the context of affinity ligand binding dissociation constants, the term "about" allows for the degree of variation inherent in the methods utilized for measuring affinity binding. For example, depending on the level of precision of the instrumentation used, standard error based on the number of samples measured, and rounding error, the term "about $10^{-2}$M" can include, for example, from 0.05 M to 0.005 M.

In some embodiments, the affinity ligand binds the target ligand with an off rate (k(off)) of less than or equal to about $5 \times 10^{-2}$ sec$^{-1}$, about $10^{-2}$ sec$^{-1}$, about $5 \times 10^{-3}$ sec$^{-1}$, about $10^{-3}$ sec$^{-1}$, about $5 \times 10^{-4}$ sec$^{-1}$, about $10^{-4}$ sec$^{-1}$, about $5 \times 10^{-4}$ sec$^{-1}$, about $10^{-4}$ sec$^{-1}$, about $5 \times 10^{-5}$ sec$^{-1}$, about $10^{-5}$ sec$^{-1}$, about $5 \times 10^{-6}$ sec$^{-1}$, about $10^{-6}$ sec$^{-1}$, about $5 \times 10^{-7}$ sec$^{-1}$, or about $10^{-7}$ sec$^{-1}$.

In some embodiments, the affinity ligand binds the target ligand with an on rate (k(on)) of greater than or equal to about $10^3$ M$^{-1}$ sec$^{-1}$, about $5 \times 10^3$ M$^{-1}$ sec$^{-1}$, $10^4$ M$^{-1}$ sec$^{-1}$, about $5 \times 10^4$ M$^{-1}$ sec$^{-1}$, $10^5$ M$^{-1}$ sec$^{-1}$, about $5 \times 10^5$ M$^{-1}$ sec$^{-1}$, $10^6$ M$^{-1}$ sec$^{-1}$, about $5 \times 10^6$ M$^{-1}$ sec$^{-1}$, $10^7$ M$^{-1}$ sec$^{-1}$, or about $5 \times 10^7$ M$^{-1}$ sec$^{-1}$.

The binding affinity and dissociation rate of the affinity ligand can be determined by any method known in the art. For example, the binding affinity can be measured by competitive ELISAs, RIAs, BIACORE™, or KINEXA™ technology. The dissociation rate also can be measured by BIACORE™ or KINEXA™ technology. The binding affinity and dissociation rate are measured by surface plasmon resonance using, e.g., a BIACORE™.

In some embodiments, the affinity ligand can modulate binding of a second or different affinity ligand to the targeting ligand. In some embodiments, the modulation is enhancement of the binding of the second or different affinity ligand to the targeting ligand. In some embodiments, the modulation is inhibition of the binding of the second or different affinity ligand to the targeting ligand. The $IC_{50}$ of such inhibition can be measured by any method known in the art, e.g., by ELISA, RIA, or Functional Antagonism. In some embodiments, the $IC_{50}$ is between 0.1 and 500 nM. In some embodiments, the $IC_{50}$ is between 10 and 400 nM. In yet other embodiments, the antibody or portion thereof has an $IC_{50}$ of between 60 nM and 400 nM.

In some embodiments, the affinity ligand has high affinity for the targeting ligand at physiological pH and reduced affinity at low pH. This can allow release of the affinity ligand from the targeting ligand at low pH.

Without limitations, the affinity ligand can be selected from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.

In some embodiments, the affinity ligand is selected from the group consisting of 4-mercaptoethyl pyridine, triazines, 2-mercapto-5-benzymidazole sulfonic acid, peptides, protein A, protein G, protein L, protein A/G/L mimetics, domains and sub-domains, Fc receptor, Fc receptor mimetics, phenyl boronic acid, boronic acid derivatives, N-benzyl-N-methyl ethanolamine, N-benzoyl-homocysteine, TRIM21 and its mimetics, Clusterin and its mimetics, histidyl-aminohexyl based, 2-mercaptoimidazole, 2-mercapto-1-methylimidazole, 2-benzamido-4-mercaptobutanoic acid, phenylpropylamine, hexylamine, 3-(2-mercaptoethyl)quinazoline-2,4(1H,3H)dione, ficolin and its mimetics, 4'-terpyridinylsulfanylethylamine, 4-(1H-imidazol-1-yl)aniline, Poly(4-vinylpyridine), ligands used for antibody purification which specifically bind to antibodies non-covalently, any combinations or modifications thereof.

In some embodiments, the affinity ligand is an antibody binding peptide as described in US Patent Application Publication No. 2011/0312877, content of which is incorporated herein by reference in its entirety for antibody binding peptides. In some embodiments, the affinity ligand is a antibody-binding protein cage as described in Kang et al., *Biomaterials*, vol. 33, no. 21, pp. 5423-30, July 2012, content of which is incorporated herein by reference in its entirety.

The affinity ligand can be linked to the molecule of interest via a linker. As used herein, the term "linker" means an organic moiety that connects two parts of a compound. Linkers typically comprise a direct bond or an atom such as oxygen or sulfur, a unit such as NH, C(O), C(O)NH, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, NH, C(O). The terms linker and spacer are used interchangeably herein. The linker can comprise any combinations of the above. Accordingly, in some embodiments, the linker can comprise hydrocarbons, amino acids, peptides, polyethylene glycol of various lengths, cyclodextrins, and derivatives and any combinations thereof.

In some embodiments, the linker is a branched linker. By a branched linker is meant a linker that can come together three or more part together. The branch-point of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branch-point is glycerol or derivative thereof, and normal chain sugars such as monosaccharides and polysaccharides. A branched linker can be used to connect two or more (e.g., 2, 3, 4, 5, 6, 7, 8, 9, 10 or more) molecules of interest (which can be same or different) to one affinity ligand; two or more (e.g., 2, 3, 4, 5, 6, 7, 8, 9, 10 or more) affinity ligands (which can be same or different) to one molecule of interest; or two or more (e.g., 2, 3, 4, 5, 6, 7, 8, 9, 10 or more) molecules of interest (which can be same or different) to two or more (e.g., 2, 3, 4, 5, 6, 7, 8, 9, 10 or more) affinity ligands (which can be same or different).

In some embodiments, two affinity ligands (which can be same or different) are attached to one therapeutic agent. For example, the two affinity ligands (which can be same or different) can be attached to one therapeutic agent via a branched linker, such as a linker comprising a trivalent branch-point.

In some embodiments, the linker comprises at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. The cleavable linking group can comprise esters, peptides, carbamates, acid-labile, reduction-labile, oxidation-labile, disulfides, and modifications thereof.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)—S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C$_1$-C$_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleavable in an acidic environment with a pH of about 6.5 or lower (e.g., about 6.0, 5.5, 5.0, or lower), or by agents such as enzymes that can act as a general acid.

In some embodiments, the linker comprises an acid labile group, e.g., hydrazone or carbamate. In some embodiments, the linker comprises an enzyme labile group e.g., maleimidecaproyl-valyl-citrullinyl-p-aminobenzylcarbamate.

The cleavable linking group can be located anywhere in the linker. For example, the cleavable linking group can be located at a terminus of the linker. In some embodiments, the cleavable linking group is located at the linker terminus distal to the affinity ligand. In some embodiments, the cleavable linking group is located at the linker terminus distal to the molecule of interest, e.g., therapeutic agent. In some embodiments, the cleavable linking group is in the linker itself. In some embodiments, the cleavable linking group connects the linker to the molecule of interest, e.g., therapeutic agent. In some embodiments, the cleavable linking group connects the linker to the affinity ligand. Thus, in some embodiments of the invention, the linker can be linked to the affinity ligand and/or the molecule of interest via a cleavable linking group.

In some embodiments, the linker can be linked to the affinity ligand and/or the molecule of interest via a non-cleavable group such as, for example, a bond, ether, thio-ether and hydrocarbon.

In some embodiments, the linker comprises a thio-ether linkage.

In some embodiments, the linker comprises a peptide, e.g., a dipeptide, a tripeptide, a tetrapeptide, or a pentapeptide. The peptide can be optionally substituted.

In some embodiments, the linker comprises a disulfide linkage.

In some embodiments the linker comprises a self-immolative disulfide linkage.

In some embodiments, the linker is a bond.

In some embodiments, the linker is a hydrocarbon, PEG, an amino acid, a peptide, or a combination thereof. The hydrocarbon or PEG can be substituted or unsubstituted.

In some embodiments, the linker is a PEG of a molecular weight of about 200 Da to about 50 kDa.

In some embodiments, the linker comprises an optionally modified PEG and at least one amino acid, (e.g., one, two, three, four, five, six, seven, eight, nine, ten or more amino acids).

In some embodiments, the linker comprises an optionally modified PEG and two amino acids, e.g., a dipeptide.

In some embodiments, the linker comprises an optionally modified PEG and three amino acids, e.g., a tripeptide.

In some embodiments, the linker comprises a peptide of amino acid sequence Lys-Val-Gly-Ala.

In some embodiments, the linker comprises β-cyclodextran-PEG conjugate.

In some embodiments, the linker comprises a co-ordination metal complex, e.g., the linker is —B—C—B'—, wherein B and B' are independently a linker as defined herein and C is coordination metal complex. The coordination metal complex can either form part of the linker backbone or be present as a sidechain to the linker backbone. Exemplary co-ordination metal complexes include complexes of Pt, Fe, Si and the like. For example the co-ordination complex can comprise tetraamminecopper(II) sulphate, iron, or silicon. Thus, as used herein, the linker can also include a Pt(II) coordination complex capable of being covalently bonded to a drug or cytotoxic agent. The drug can be attached to the platinum coordination complex via an amide, ester, amine, ether, hydrazide, disulfides or imine linkages.

In some embodiments, the co-ordination metal complex is a platinum complex. In some embodiments, the complex comprises at least one coordination bond.

In some embodiments, the platinum complex is

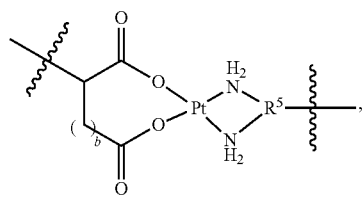

wherein b is 0, 1, 2, 3, 4, or 5 and $R^5$ is a cyclic or acyclic linker joining the two amino groups to rest of the linker. In some embodiments, b is 1.

In some embodiments, $R^5$ is

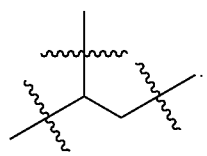 [SMILES: *CC(*)*]

In some embodiments, $R^5$ is a cyclic linker selected from aryl, heteroaryl, cyclyl or heterocyclyl. In some embodiments, the platinum complex is

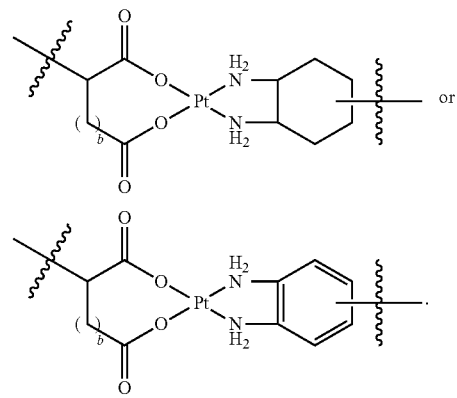

In one embodiment, the platinum complex is

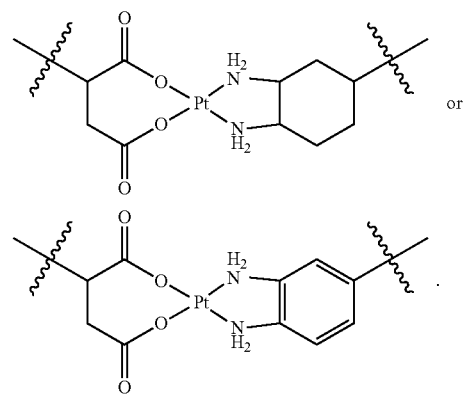

In one embodiment, the platinum complex is

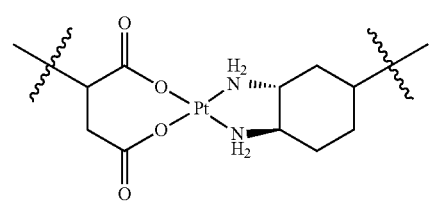

In some embodiments, the platinum complex is

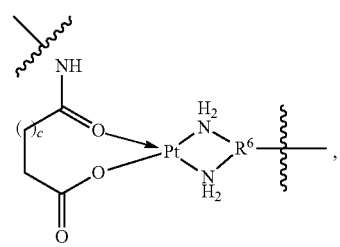

wherein c is 0, 1, 2, 3, 4, or 5 and $R^6$ is a cyclic or acyclic linker joining the two amino groups to rest of the linker. In some embodiments, c is 1.

In some embodiments, R⁶ is

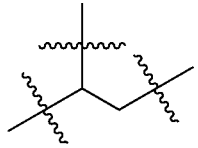

In some embodiments, R⁶ is a cyclic linker selected from aryl, heteroaryl, cyclyl or heterocyclyl. In some embodiments, the platinum complex is

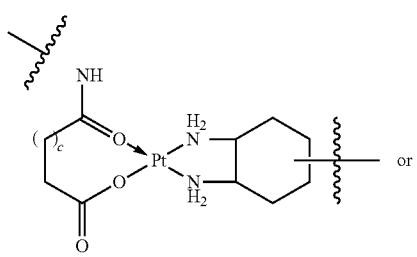 or

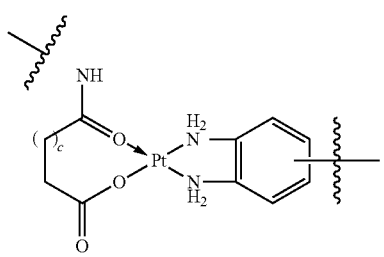.

In one embodiment, the platinum complex is

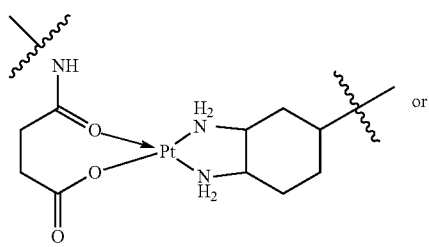 or

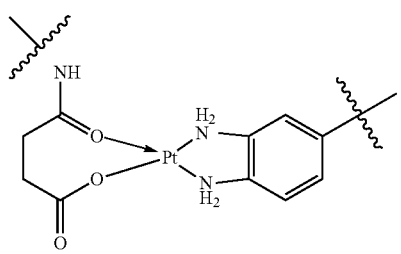.

In some embodiments, the platinum complex is

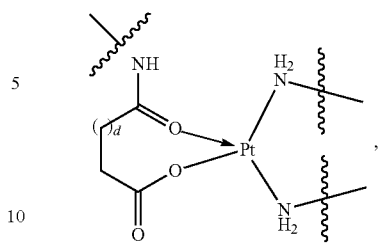, wherein d is 0, 1, 2, 3, 4, or 5. In some embodiments, d is 1.

In some embodiments, the platinum complex is

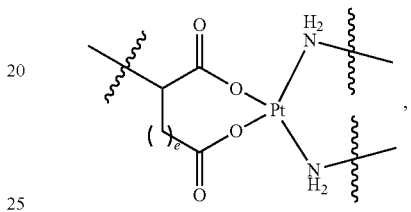, wherein e is 0, 1, 2, 3, 4, or 5. In some embodiments, e is 1.

In some embodiments, the platinum complex is

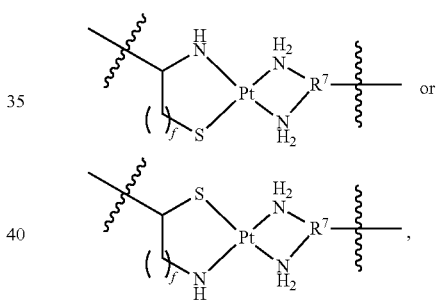

wherein f is 0, 1, 2, 3, 4, or 5 and R⁷ is a cyclic or acyclic linker joining the two amino groups to rest of the linker.

In one embodiment, f is 1.

In some embodiments, R⁷ is

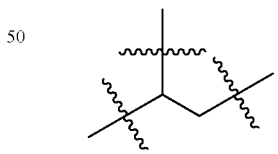.

In some embodiments, R⁷ is a cyclic linker selected from aryl, heteroaryl, cyclyl or heterocyclyl.

In some embodiments, the platinum complex is

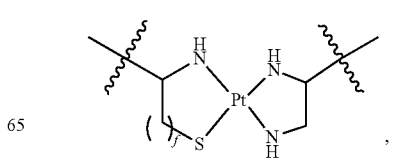,

-continued

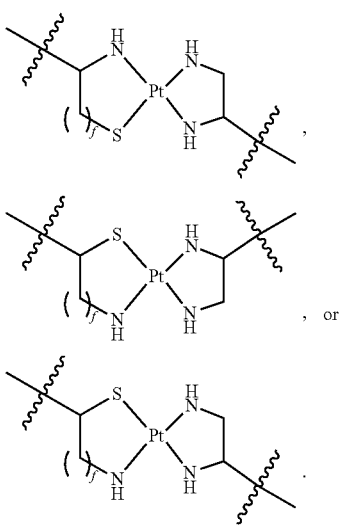

In some embodiments, the platinum complex is

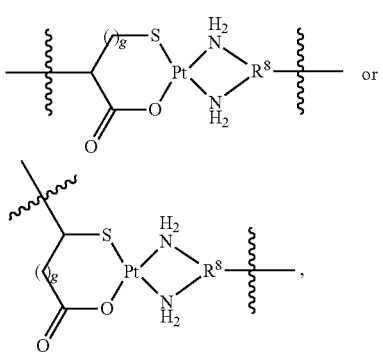

wherein g is 0, 1, 2, 3, 4, or 5 and $R^8$ is a cyclic or acyclic linker joining the two amino groups to rest of the linker. In one embodiment g is 1

In some embodiments, $R^8$ is

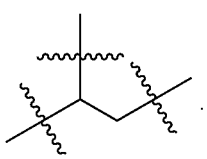 [SMILES: *CC(*)*]

In some embodiments, $R^8$ is a cyclic linker selected from aryl, heteroaryl, cyclyl or heterocyclyl.

In some embodiments, the platinum complex is

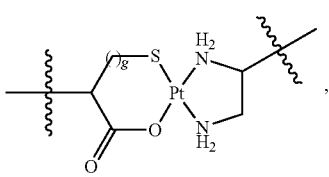

-continued

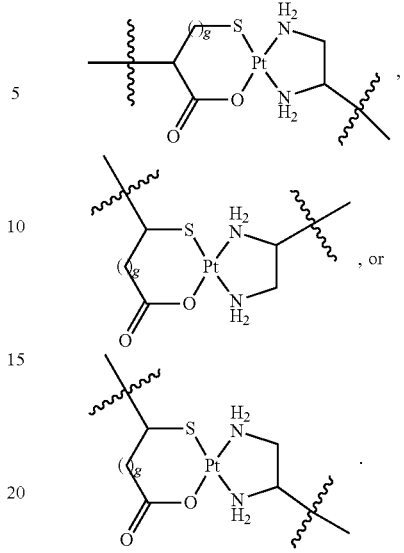

In some embodiments, the platinum complex is

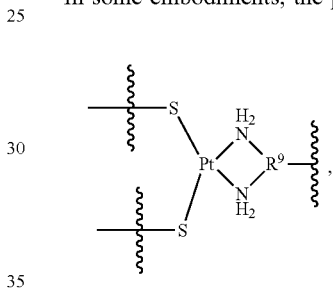

wherein $R^9$ is a cyclic or acyclic linker joining the two amino groups to rest of the linker. In some embodiments, $R^9$ is

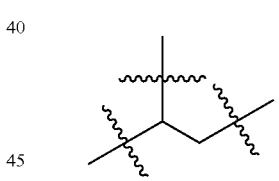

In some embodiments, $R^9$ is a cyclic linker selected from aryl, heteroaryl, cyclyl or heterocyclyl.

In some embodiments, the spacer could be a peptide such as lysine-valine-glycine-alanine.

In some embodiments, the spacer could be a β-cyclodextrin attached to a polyethylene glycol unit.

In some embodiments, the spacer could be a polyethylene glycol unit attached to a glycine or alanine which is further linked to a camptothecin cytotoxin through an ester bond.

In some embodiments, the spacer is a peptide (2 to 5 amino acids) or a polyethylene glycol unit linked to a diamine which is further branched and attached to 2 or more drug units.

In some embodiments, the spacer could be a combination of amino acids and polyethylene glycol unit.

In some embodiments, the spacer could be composed of amino acids and peptide bonds which also serve as cleavable linkers.

In certain embodiments, the spacer could be a hydrocarbon chain of varying length linked to the drug via a cleavable ester bond.

In certain embodiments, the spacer could be a hydrocarbon chain of varying length linked to the drug via a cleavable peptide bond.

In certain embodiments, the spacer could be a hydrocarbon chain of varying length linked to the drug via a cleavable carbamate bond.

In some embodiments, the affinity ligand is directly bonded with the drug without any spacer which could be cleavable or non-cleavable.

Without limitations any molecule of interest, e.g., therapeutic agent can be conjugated in the targeted drug delivery conjugates described herein. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, antisense oligonucleotides, aptamers, ribozymes, viruses, proteins, lipids, pro-inflammatory molecules, antibodies, antibiotics, anti-inflammatory agents, anti-sense nucleotides and transforming nucleic acids or combinations thereof. Any of the therapeutic agents can be combined to the extent such combination is biologically compatible. The therapeutic agent is selected according to the treatment objective and biological action desired.

In some embodiments, the therapeutic agent can be modified to make it more soluble and/or so that it cleaves from the linking molecule at the target site. As an example for cancer therapy, after administering the conjugate in the bloodstream of the patient, the mechanism of action can involve the targeting moiety binding to the specific anti-ligand on the cancer cell, internalization of the entire conjugate through receptor-mediated endocytosis, disruption of the non-covalent linkage between the affinity ligand and the targeting moiety at low pH in the endosome, cleavage of the drug from the linking molecule, if needed, and the drug translocating to the site of action.

Exemplary therapeutic agents include, but are not limited to, those found in *Harrison's Principles of Internal Medicine*, 13$^{th}$ Edition, Eds. T. R. Harrison et al. McGraw-Hill N.Y., N.Y.; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

General classes of therapeutic agents include anti-microbial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, diagnostic agents, gene therapy agents, hormonal agents, mucolytic agents, radioprotective agents, radioactive agents including brachytherapy materials, tissue growth inhibitors, tissue growth enhancers, vasoactive agents, and thrombolytic agents.

Examples of therapeutic agents which can be used, include but are not limited to, narcotic analgesic drugs; salts of gold; corticosteroids; hormones; antimalarial drugs; indole derivatives; pharmaceuticals for arthritis treatment; antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weight controlling drugs; thyroid gland controlling drugs; analgesics; drugs controlling fertilization or contraception hormones; amphetamines; antihypertensive drugs; antiinflammatory agents; antitussives; sedatives; neuromuscular relaxants; antiepileptic drugs; antidepressants; antidisrhythmic drugs; vasodilating drugs; antihypertensive diuretics; antidiabetic agents; anticoagulants; antituberculous agents; antipsychotic agents; hormones and peptides. It is understood that above list is not full and simply represents the wide diversification of therapeutic agents that may be included in the compositions.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N°-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g., testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

In some embodiments, the therapeutic agent, e.g., the drug is an anti-cancer agent. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

In some embodiments, the therapeutic agent can be selected from the group consisting of cytotoxic drugs like Maytansinoid (DM1 and DM4); CC-1065; Adozelesin (DC1); DC4; Calicheamicins; Dolastatins; Auristatins E and F; Meamycin; Doxorubicin; Paclitaxel; Docetaxel; Laulimalide; Epothilones A and B; Discodermolide; Eleutherobin; Peloruside A; cyclophosphamide, chlorambucil, uramustine, ifosfamide, melphalan, and bendamustine; Carmustine, lomustine, semustine; Busulfan; Thiotepa; Dacarbazine; Methotrexate; 6-mercaptopurine, 6-thioguanine, pentostatin, fludarabine; 5-fluorouracil, cytarabine, leukovorin; Dactinomycin; Bleomycin; Daunorubicin; Mitomycin; Idarubicin; Plicamycin; Vincristine; Vinblastine; Vinorelbine; Etoposide; Teniposide; Asparaginase; Maitotoxin; Irinotecan (CPT-11); Fumagillin; Fumagalone; Fumarranol; O-(Chloroacetylcarbamoyl)-Fumagillol (AGM-1470, TNP-470); 27-hydroxybullatacin and other chemotherapeutic drugs, derivatives and analogues thereof, and any combinations thereof.

In some embodiments, the therapeutic agent can be a radioactive material. Suitable radioactive materials include, for example, $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{32}$phosphorous, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{123}$lead, $^{111}$Indium, $^{52}$iron, $^{167}$thulium, $^{57}$nickel, $^{62}$zinc, $^{62}$copper, $^{201}$thallium and $^{123}$iodine. Without wishing to be bound by a theory, aggregates comprising a radioactive material can be used to treat diseased tissue such as tumors, arteriovenous malformations, and the like.

In some embodiments, the molecule of interest can be an imaging or contrast agent. As used herein, the term "imaging agent" refers to an element or functional group in a molecule that allows for the detection, imaging, and/or monitoring of the presence and/or progression of a condition(s), pathological disorder(s), and/or disease(s). The imaging agent may be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p (2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H,15H-Xantheno[2,3,4-ij: 5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, *Mol. Microbiol*, 55:1767-1781 (2005), the GFP variant described in Crameri et al, *Nat. Biotechnol.*, 14:315319 (1996), the cerulean fluorescent proteins described in Rizzo et al, *Nat. Biotechnol*, 22:445 (2004) and Tsien, *Annu. Rev. Biochem.*, 67:509 (1998), and the yellow fluorescent protein described in Nagal et al, *Nat. Biotechnol.*, 20:87-90 (2002). DsRed variants are described in, e.g., Shaner et al, *Nat. Biotechnol.*, 22:1567-1572 (2004), and include mStrawberry, mCherry, mOrange, mBanana, mHoneydew, and mTangerine. Additional DsRed variants are described in, e.g., Wang et al, *Proc. Natl. Acad. Sci. U.S.A.*, 101:16745-16749 (2004) and include mRaspberry and mPlum. Further examples of DsRed variants include mRFPmars described in Fischer et al, *FEBS Lett.*, 577:227-232 (2004) and mRFPruby described in Fischer et al, *FEBS Lett*, 580:2495-2502 (2006).

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane.

Suitable non-metallic isotopes include, but are not limited to, $^{11}C$, $^{14}C$, $^{13}N$, $^{18}F$, $^{123}I$, $^{124}I$, and $^{125}I$. Suitable radioisotopes include, but are not limited to, $^{99m}Tc$, $^{95}Tc$, $^{111}In$, $^{62}Cu$, $^{64}Cu$, Ga, $^{68}Ga$, and $^{153}Gd$. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to the aggregate. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the nanoparticles.

In some embodiments, the imaging agent can be selected from the group consisting of [111In]B3; [111In]SRVII23; [124I]DIATHIS-1; [18F]-AH113804; [18F]DCFPyL; [18F] ICF-01006; [99mTc]Met; 105A5; 111In antisense oligonucleotide CDK inhibitor imaging agent (intravenous, Cancer), University of Toronto; 111In anti-tPA, Novo Nordisk; 111In RM-2; 111In-Benzyl-DTPA-Z(HER2:342)-pep2; 111In-capromab pendetide; 111In-GLP-1 analogs (neuroendocrine tumor imaging); 111In-labeled lactam bridge-cyclized alpha-melanocyte-stimulating hormone peptide (melanoma), NuView/University of New Mexico; 111In-labeled LFA-1 targeted imaging agent (lymphoma/leukemia), NuView/University of New Mexico; 11C-6-Me-BTA-1; 11C-atrasentan PET imaging agent (cancer), Abbott; 11C-AZD-2184; 11C-AZD-2995; 11C-carfentanil; 11C-GSK-215083; 11C-labeled sigma opioid receptor ligands, Santen; 11C-LY-2795050; 11C-MePPEP; 11C-MICA; 11C-MK-3168; 11C-MK-8278; 11C-PBR-170; 11C-PBR-28; 11C-R-129144; 11C-RU-40555; 123I-CMICE-013; 123I-DRM-106; 123I-eptacog alfa (bleeding), Novo Nordisk; 123I-IMPY; 123I-iodometomidate; 123I-iofetamine; 123I-ioflupane; 123I-iomazenil, Nihon Medi-Physics; 123I-iometopane; 123I-labeled dopamine antagonist (Parkinsonistic features), Copenhagen University; 123I-MIBG, Molecular Insight; 123I-MNI-168; 123I-MNI-330; 123I-MNI-420; 123-iodine labeled exendin derivatives (imaging GLP-1 receptors, diabetes), Kyoto University/Arkray; 123I-TM-601; 124I-A33; 124I-labeled 11-1F4; 124-iodine-labeled PSCA targeting minibody (cancer), ImaginAb; 124I-PGN-650; 125I-AnnA1 IgG; 125I-MIBG, Neoprobe/Childrens Cancer Group/CIS; 125-Iodine-labeled MFE-23; 131I-chTNT-1/B; 131I-radretumab; 131I-TM-601; 177Lu-AMBA; 178Tantalum; 18F ISO-1; 18F labeled ethanolamine derivatives (cancer imaging), Bayer Schering; 18F-AV-45 dimer; 18F-BAY-85-8050; 18F-FDDNP; 18F-FEDAA-1106; 18F-FEPPA; 18F-fluoromethylallylcholine; 18F-flutabine; 18F-F-PEB; 18F-FRP-170; 18F-labeled fluoropolyethylene glycol derivatives (Alzheimers disease detection), University of Pennsylvania; 18F-labeled glyburide analogs, University of Pennsylvania; 18F-labeled nAChR antagonists (Alzheimers disease), University of California Irvine; 18F-labeled PET imaging agent (melanoma), Wake Forest University; 18F-MNI-558; 18F-NST-ML-10; 18F-SKI-696; 18F-SMIBR-K5; 18F-SMIBR-W372; 18F-VEGF binding peptides (PET imaging), Genentech; 203Pb/212Pb-radiolabled ErbB-2 receptor targeting peptides (cancer), AlphaMed; 227Th-rituximab (cancer), Algeta; 28A32; 3E8; 5-aminolevulinic acid hydrochloride (glioma imaging), Nobelpharma; 62Cu-ATSM; 62Cu-ETS; 62Cu-PTSM; 64Cu-AMG-655; 64Cu-TM-601; 64-Cu-TP-3805; 68Ga-based PET tracer (cancer imaging), Novo; 68Ga-EC-G; 6-FPOL; 76Br-16alpha, 17alpha-dioxolane progestin analogs (breast cancer), Washington University/University of Illinois; 98mTC-CIM-ANT; 99mTc-betafectin; 99m-Tc labelled annexin V-128 (rheumatoid arthritis/Crohn's disease), Atreus; 99m-Tc MAG3-HER2/MUC1 peptide (breast cancer), King Faisal; 99mTc TR-21; 99mTc-anti-ED-B; 99mTc-AP(4)A; 99mTc-apcitide injection; 99mTc-besilesomab; 99mTc-ciprofloxacin, DRAXIS; 99mTc-ciprofloxacin, INMAS; 99mTc-Demogastrin 2 (medullary thyroid cancer), Biomedica Life Sciences; 99mTc-depreotide; 99mTc-DTPA; 99mTc-DTPA-Glipizide; 99mTc-EC-0652; 99mTc-EC-DG; 99mTc-EC-metronidazole; 99mTc-fanolesomab; 99mTc-glucarate; 99mTc-Hynic-Annexin V; 99mTc-labeled non-steroidal analogs (cancer, imaging/detection), Roche; 99mTc-labeled PSMA inhibitors (prostate cancer, imaging), Johns Hopkins University; 99mTc-labelled adrenomedullin (pulmonary disease), PulmoScience; 99mTc-maraciclatide; 99mTc-MAS3-TM-601; 99mTc-MIP-1340; 99mTc-MIP-1404; 99mTc-MIP-1405; 99mTc-MIP-1407; 99mTc-MSA; 99mTc-N4-Tyrosine; 99mTC-NC-100668; 99mTc-N-DBODC5; 99mTc-nitrocade; 99mTc-nitroimidazole, Bristol-Myers Squibb; 99mTc-P215; 99mTc-P424; 99mTc-P483H; 99mTc-P587; 99mTc-P748; 99mTc-rBitistatin; 99mTc-rotenone conjugates (cardiac perfusion), Molecular Insight; 99mTc-RP-128; 99mTc-seglitide analog, DRAXIMAGE; 99mTc-sestamibi; 99mTc-siboroxime; 99mTc-sulesomab; 99mTc-teboroxime; 99mTc-tetrofosmin; 99mTc-TP-850; 99m-Tc-tropantiol; 99m-Technetium labeled azetidinylmethoxypyridine derivatives (nervous system imaging), Kyoto University; A-84543; AB-3025-11; ABD-035; Abdoscan; ABY-025; ABY-026; ABY-028; acetylcholinesterase (AChE) inhibitors (Alzheimer's disease), University of California/Scripps Institute/Siemens Medical Solutions Molecular Imaging; Adenoscan; AdreView; AGT-100; AGT-160; Albunex; alpha-7 nicotinic receptor binding PET ligands (neurological disorders), NeuroSearch/University of Copenhagen; Altropane; AMI-121; AMI-25; AMI-HS; amyloid beta MRI contrast agents (Alzheimers), Mayo Clinic; amyloid beta oligomers (imaging agent), University of California Davis; amyloid binding PET ligands (Alzheimers disease), Aventis; ANA-5 analog (oral radiolabelled imaging agent, Alzheimers disease), Alzhyme; androgen receptor modulators (imaging, cancer) University of Nebraska Medical Center; anti PSA antibody conjugates (prostate cancer therapy/diagnosis), Molecular Imaging and Therapeutics; antibodies conjugated fluorochromes/radionuclides (cancer), TTFactor srl; antimelanoma antibodies, MabCure; Anti-ZnT8 antibody imaging agent (diabetes), Mellitech SAS; AP-2011; apadenoson; arcitumomab; AT-004; atrial natriuretic peptide, DRAXIMAGE; AVP-4; AVP-5; AVP-6; AVP-7; AZD-4694; Azedra; AZPET; BAY-1006451; BAY-1006578; BAY-1075553; BAY-1163615; BAY-85-8102; BAY-86-4367; BAY-86-4884; BAY-86-7548; BAY-86-9596; BChE inhibitors (imaging, Alzheimers disease), University of Nebraska Medical Center; BCI-632; beta1-adrenoceptor-targeted imaging agents (cardiovascular disease), Lantheus; BFPET; binodenoson; bivalirudin (nanoparticle, thrombosis), Kereos; BMIPP, Nihon; BMS-753951; BOT-502; BR-14; BR-55; BT-19; BT-20; BT-23; BW-42; BY-963; C11-SB-207145; calcium nanoparticles (cancer detection), BioLink; cancer imaging agent, AltaRex/Resolution Pharm; cancer imaging agents, MallincKrodt/Optimedx; Capiscint; carbonic anhydrase IX inhibitors (cancer, imaging), Molecular Insight; carborane-containing arylphosphonium salts (imaging/boron neutron capture therapy, cancer), University of Sydney; cardiac imaging agents (ACE targeting), Molecular Insight/University of Maryland; CardioPET; Cavisomes; CB1 antagonists (brain imaging), Johns Hopkins; cell penetrating peptide (diagnostic, cancer), CDG; CEN-109; CGRP-A2 radioligand agent (migraine), Merck; chlorin-e6-conjugated mucin-targeted aptamers (photodynamic therapy/imaging, cancer), Ontario Cancer Institute; CLR-1404 (fluorescent analogs); CMC-001; CMUS-100; CNS-1261; cocaine analogs, Indiana University; Collagelin; CTP, Hafslund Nycomed; CTT-54; Cu64-CND1-PNA; Cu64-CNND1-B; Cu64-CNND1-L; CUSCA; D-04; Demobesin; depelestat; diagnostic agent (infectious diseases), Univalor; DMP-444; DOTA-BASS (cancer), Salk Institute; DOTA-NT-MSH targeted alpha particle-emitting radionuclides (cancer), AlphaMed; DX-182; E-7210; EchoGen; Echovist; EM-2198; EM-3106B; ENDG-4010; EP-1242; EP-1873; EP-2104R; EP-3533; EP-862; EPI-HNE-2; EVP-1001-1; eye disease program, NuvOx Pharma; F-18 exendin-4 derivative PET tracers (diabetes), Kyoto University/Arkray; F-18-CCR1; F-18-HX4; F-18-VM4-037; FerriSeltz; ferumoxtran-10; ferumoxytol; fibrin-binding radiodiagnostic (thrombosis), DRAXIMAGE/Savient; florbenazine (18F); florbetaben (18F); florbetapir (18F); florilglutamic acid (18F); fluciclatide F 18; Fluoratec; fluorescein derivative contrast agent (imaging, ocular disease), Philogen; fluorescent LYVE-1 antibody (imaging agent, cancer), University of California/Anticancer Inc; fluorine-18-based PET imaging agents (neuropsychiatric disorders), Janssen; fluorine-18-labelled peptides (PET cancer imaging), Immunomedics; fluoropegylated indolylphenylacetylenes (Alzheimer's disease), Avid; flurpiridaz F 18; flutemetamol (18F); folate-targeted imaging agents (inflammation), Endocyte/Purdue University; fullerene-encapsulated MRI imaging agents, Luna Innovations; functionalized liposomes (stroke), Universidade de Santiago de Compostela; gadobenic acid; gadobutrol; gadocoletic acid; gadodiamide; gadofluorine 8; gadofosveset; gadolinium based C60 fullerene-paclitaxel-ZME-018 conjugates (prodrug/imaging, cancer), TDA Research/Rice University/MD Anderson; gadolinium texaphyrin; gadolinium texaphyrins (imaging, atherosclerosis), Pharmacyclics; gadolinium zeolite; gadomelitol; Gadomer-17; gadopenamide; gadopentetate dimeglumine; gadoteridol; gadoversetamide; gadoxetate disodium; gallium-68 pasireotide tetraxetan; Gd contrast agents (liposomal nanoparticles), ImuThes Therapeutics; GE-226; Glio-Image, Targepeutics; Gliolan; GL-ONC1; GlucaGen; GlucoMedix; Glysopep; GlyT1 PET radiotracers (schizophrenia), Merck & Co; GN-1140; GP-2-193; GTx-100; GW-7845; hedgehog labelled stem cells (cancer), Radiomedix; Hexvix; hMAG-1 targeting GRSA (imaging, breast cancer), Woomera; HRC-201; humanized ATA antibodies (imaging, cancer), Enlyton; humanized mAbs (breast cancer), Kalgene; HumaSPECT; hyaluronic acid-Gd, Hyal; I-124-CLR1404; ibritumomab tiuxetan; IL-8 analogs, Diatech; imaging agent (infectious disease), NuView; imaging agent (pancreatic cancer), NuView/University of New Mexico; imaging-theranostic nanoemulsion agents (multidrug resistant ovarian cancer), Nemucore/Fox Chase Cancer Center/Northeastern University; IN-N01-OX2; INP-04; intetumumab; iobitridol; iodine (124I) girentuximab; iodine-124-labeled F-16 scFv antibody (PET immunodetection, cancer), Philogen; iodixanol; iodofiltic acid (123 I); ioflubenzamide (131I); iofolastat I 123; ioforminol; iohexol; iomeprol; iopamidol; iopiperidol; iopromide; iosimenol; iosimide; iotrolan (oral, X-ray imaging), Schering AG; J-001X; KDF-07002; KI-0001; KI-0002; KI-0003; KI-100X; labeled TSH superagonists (thyroid cancer), Trophogen; landiolol (coronary imaging), Ono; LeucoTect; Levovist; LipoRed; LM-4777; LMI-1195; Lumacan; LumenHance; LymphoScan; mangafodipir; matrix metalloproteinase inhibitor (atherosclerosis), Lantheus; MB-840; meglumine gadoterate; Metascan; mGlu2 receptor PET ligand (psychiatric disease), Johnson & Johnson; mGluR5 PET tracers (neurodegenerative disease), Merck & Co; MH-1, American Biogenetic; MIP-160; MIP-170D; MIP-170S; MM-Q01; MN-2011; MN-3015; Monopharm-C; MRX-408; MRX-825; MS-136; MS-264; myocardial imaging agent, Mallinckrodt; Myomap; N-0861; N-1177-inh; N-1177-iv; N-1177-sq; nAChR PET agent, NIDA; Nano-Barium; NanoLymph; nanoparticle MRI agents (Alzheimers disease/cancer), Senior Scientific; nanotherapeutics (breast cancer, lung cancer, infectious diseases, sepsis, atherosclerosis), SignaBlok; NC-100150; NC-100182; NCL-124; NCTX; NK3 antagonist PET ligand (psychiatric disease), AstraZeneca; NMDA radioligands, Kyushu University; NMK-36; nociceptin/orphanin FQ receptor PET ligands (neuropsychiatric disorders), Eli Lilly; nofetumomab; NP-50511; NS-2381; NSI-1; NVLS/FMAU; NVLS/FX-18A; OBP-401; octafluoropropane; OctreoScan; oligonucleotide (HNE), NeXstar; omacianine; Oncotec; Oralex;

OvaFluor; oxidronic acid; oxilan; P-3378; P-773; P-947; PB-127; Pb-203 labeled[DOTA]-ReCCMSH targeted alpha particle-emitting radionuclides (cancer), AlphaMed/University of Missouri; PCP-Scan; PDL-506; Pentacea; Pepscan; peptide-based PET radiotracer (breast cancer), Stanford University Medical Center; perflexane-lipid microsphere; perflubutane (lipid microsphere-encapsulated, imaging), Daiichi Sankyo; perflubutane (polymer microsphere-encapsulated, heart disease), Acusphere; perflutren lipid microsphere; PET imaging agent (Alzheimer's disease), AC Immune; PET imaging agent (anti-5T4 tumor antigen Ab, ovarian cancer), ImaginAb; PET imaging agent (cancer), Cancer Targeted Technology/Bayer; PET imaging agent (melanoma), Acaduceus; PET imaging agent (neurodegenerative diseases), Fujisawa; PET imaging agent (thrombosis), Astellas; PET imaging agents (cancer), Affinity Pharmaceuticals; PET imaging agents (cardiovascular disease), ImaginAb/GE Healthcare; PET radiotracer (prostate cancer), Johns Hopkins University School of Medicine; PET radiotracer (solid tumors), MD Anderson Cancer Center; phosphodiesterase 10 imaging agent (PET, neurological disorders), Institute for Neurodegenerative Disorders; PIMBA; Prognox; ProScan-A; ProstaFluor; ProstaLite; Prostatec; Prostaview; PT-16; pyridyl benzofuran derived imaging agent (nervous system disorder), Kyoto University; Quantison; QW-7437; radiolabeled antibodies, University of Sydney/ANSTO; radiolabeled anti-CD4 monoclonal antibody fragment (imaging agent, chronic inflammation), Biotectid; radiolabeled anti-CEACAM6 antibodies (imaging/cancer), NIH; radiolabeled anti-PSMA huJ591 minibodies (prostate cancer), ImaginAb; radiolabeled anti-RECAF antibodies (cancer), BioCurex; radiolabeled DTPA-adenosylcobalamin, Copharos; radiolabeled HPMA copolymer conjugates (angiogenesis), Molecular Insight; radiolabeled iodobenzamide, INSERM; radiolabeled leukotrine B4 antagonist, University of Nijmegen/BMS; radiolabeled onartuzumab (imaging, cancer), Genentech; radiolabeled sigma-2 receptor ligands (solid tumor), Washington University in St Louis; radiolabeled VEGF (cancer), Sibtech/Stanford; radiolabeled VEGFR-1 inhibitors (cancer), IASON; radiolabeled WC-10 (neurological disease), Washington University; radiolabelled-A20FMDV2; radiotargeted gene therapy HSV1-tk (cancer), KIRAMS; recombinant TSH superagonists (thyroid cancer), Trophogen; regadenoson; RESP-3000; RG-7334; RP-431; RP-517; RP-748; samarium-153-DOTMP; SapC-DOPS, Molecular Targeting Technology/Bexion; secretin human; seprase inhibitors (cancer, imaging), Molecular Insight; SF-25; SH-U-555-C; SH-U-563; sigma-opioid ligand, NIH; SLX-1016; somatostatin analogs, Neoprobe; SonoRx; SPAGO Pix; SPIO-Stasix nanoparticles (imaging/therapeutic, prostate cancer), Androbiosys/Roswell Park Cancer Institute; sprodiamide; SPVF-2801-10; SR-4554; STARBURST dendrimer-based MRI contrast agents (cardiovascular disease/ovary cancer), Dendritic Nanotechnology; steroid mimics (breast cancer imaging/therapy), Daya Drug Discoveries; sulphur hexafluoride microbubble ultrasound agent, Bracco; targeted nanoparticle-enhanced pro-apoptotic peptides (glioblastoma), Sanford-Burnham/Salk Institute; targeted two-photon photodynamic therapy (cancer), SensoPath; tau-binding PET tracer (Alzheimer disease), Siemens; Tc99-labeled 14F7 humanized mAb (cancer imaging), The Center of Molecular Immunology; T-cell co-receptor targeting PET imaging agent (antibody fragment, cancer/inflammation/transplantation), ImaginAb; Tc-HL-91; TechneScan Q12; technetium (99m Tc) bicisate; technetium Tc 99m etarfolatide; technetium Tc 99m tilmanocept; technetium-99m-RP-414, Resolution; TF-12-radiolabeled IMP-288 (cancer), Immunomedics; TF-2 plus diagnostic/therapeutic (cancer), Immunomedics; Tin-117m-labeled annexin (heart disease), Clear Vascular; TKS-040; TLC I-16; TomoRx; TPM+imaging agents; transcript imaging technology, Sugen/NCI; TRC-105; triiodobenzene contrast agents, Nycomed; TruScint; TSARs, Cytogen/Elan; tumor endothelial marker antibodies (anticancer), Genzyme/John Hopkins; undisclosed compounds (epithelial/thyroid cancer), Kalgene; VasoPET; VEGF superagonists (neovascularization), Trophogen; ViaScint; VINP-28; VK-11; VMAT2 ligands (CNS disorder imaging), Molecular NeuroImaging/Institute for Neurodegenerative Disorders; WIN-70197; yttrium (90Y) clivatuzumab tetraxetan; Zn-DPA-B; Zn-DPA-G; Zn-DPA-H; Zn-DPA-I; Zn-DPA-P; and any combinations thereof.

In some embodiments, the contrast agent can be selected from the group consisting of [111In]SRVII23; [124I]DIATHIS-1; [18F]-AH113804; [18F]DCFPyL; 111In RM-2; 111In-Benzyl-DTPA-Z(HER2:342)-pep2; 11C-6-Me-BTA-1; 11C-atrasentan PET imaging agent (cancer), Abbott; 11C-AZD-2184; 11C-AZD-2995; 11C-carfentanil; 11C-GSK-215083; 11C-labeled sigma opioid receptor ligands, Santen; 11C-LY-2795050; 11C-MePPEP; 11C-MICA; 11C-MK-3168; 11C-MK-8278; 11C-PBR-170; 11C-PBR-28; 11C-R-129144; 11C-RU-40555; 123I-DRM-106; 123I-IMPY; 123I-iofetamine; 123I-iometopane; 123I-MIBG, Molecular Insight; 123I-MNI-168; 123I-MNI-420; 123-iodine labeled exendin derivatives (imaging GLP-1 receptors, diabetes), Kyoto University/Arkray; 124I-labeled 11-1F4; 131I-chTNT-1/B; 131I-radretumab; 18F ISO-1; 18F labeled ethanolamine derivatives (cancer imaging), Bayer Schering; 18F-AV-45 dimer; 18F-BAY-85-8050; 18F-FDDNP; 18F-FEDAA-1106; 18F-FEPPA; 18F-fluoromethylallylcholine; 18F-F-PEB; 18F-labeled fluoropolyethylene glycol derivatives (Alzheimers disease detection), University of Pennsylvania; 18F-labeled glyburide analogs, University of Pennsylvania; 18F-labeled nAChR antagonists (Alzheimers disease), University of California Irvine; 18F-labeled PET imaging agent (melanoma), Wake Forest University; 18F-MNI-558; 18F-NST-ML-10; 18F-SKI-696; 18F-SMIBR-K5; 18F-SMIBR-W372; 18F-VEGF binding peptides (PET imaging), Genentech; 62Cu-ATSM; 62Cu-ETS; 62Cu-PTSM; 64Cu-AMG-655; 64-Cu-TP-3805; 68Ga-EC-G; 76Br-16alpha, 17alpha-dioxolane progestin analogs (breast cancer), Washington University/University of Illinois; 99mTc TR-21; 99mTc-anti-ED-B; 99mTc-EC-DG; 99mTc-labeled PSMA inhibitors (prostate cancer, imaging), Johns Hopkins University; 99mTc-maraciclatide; 99mTc-MAS3-TM-601; 99mTc-teboroxime; 99m-Tc-tropantiol; A-84543; AdreView; Albunex; alpha-7 nicotinic receptor binding PET ligands (neurological disorders), NeuroSearch/University of Copenhagen; Altropane; amyloid beta MRI contrast agents (Alzheimers), Mayo Clinic; amyloid binding PET ligands (Alzheimers disease), Aventis; AP-2011; ASP-1001; AZD-4694; AZPET; BAY-1006451; BAY-1006578; BAY-1163615; BAY-86-4367; BAY-86-7548; BAY-86-9596; BCI-632; BFPET; BR-14; BR-55; BY-963; CardioPET; Cavisomes; CB1 antagonists (brain imaging), Johns Hopkins; CEN-109; CGRP-A2 radioligand agent (migraine), Merck; CMC-001; CMUS-100; CNS-1261; CTP, Hafslund Nycomed; CTT-54; E-7210; EchoGen; Echovist; EM-2198; EM-3106B; EP-3533; F-18 exendin-4 derivative PET tracers (diabetes), Kyoto University/Arkray; F-18-CCR1; florbenazine (18F); florbetaben (18F); florbetapir (18F); florilglutamic acid (18F); Fluoratec; fluorescein derivative contrast agent (imaging, ocular disease), Philogen; fluorine-18-based PET imaging agents (neuropsychiatric disorders), Janssen; fluorine-18-labelled peptides (PET cancer imaging), Immunomedics; fluoropegylated indolylphenylacetylenes (Alzheimer's disease), Avid; flurpiridaz F 18; flutemetamol (18F); gadoversetamide; gallium-68 pasireotide tetraxetan; Gd contrast agents (liposomal nanoparticles), ImuThes Therapeutics; GE-226; GlyT1 PET radiotracers (schizophrenia), Merck & Co; GW-7845; humanized ATA antibodies (imaging, cancer), Enlyton; HumaSPECT; I-124-CLR1404; INO-4885; INP-04; intetumumab; iobitridol; iodixanol; iohexol; iomeprol; iopamidol; iopiperidol; iopromide; iosimenol; iotrolan (oral, X-ray imaging), Schering AG; Levovist; LMI-1195; MB-840; mGlu2 receptor PET ligand (psychiatric disease), Johnson & Johnson; mGluR5 PET tracers (neurodegenerative disease), Merck & Co; MN-3015; MRX-408; Myomap; N-1177-inh; N-1177-iv; N-1177-sq; nAChR PET agent, NIDA; NanoBarium; NanoLymph; NK3 antagonist PET ligand (psychiatric disease), AstraZeneca; NMDA radioligands, Kyushu University; NMK-36; nociceptin/orphanin FQ receptor PET ligands (neuropsychiatric disorders), Eli Lilly; NP-50511; NSI-1; NVLS/FMAU; NVLS/FX-18A; octafluoropropane; omacianine; Oralex; oxilan; PB-127; Pb-203 labeled [DOTA]-ReCCMSH targeted alpha particle-emitting radionuclides (cancer), AlphaMed/University of Missouri; peptide-based PET radiotracer (breast cancer), Stanford University Medical Center; perflexane-lipid microsphere; perflubutane (lipid microsphere-encapsulated, imaging), Daiichi Sankyo; perflubutane (polymer microsphere-encapsulated, heart disease), Acusphere; perflutren lipid microsphere; PET imaging agent (Alzheimer's disease), AC Immune; PET imaging agent (anti-5T4 tumor antigen Ab, ovarian cancer), ImaginAb; PET imaging agent (neurodegenerative diseases), Fujisawa; PET imaging agent (thrombosis), Astellas; PET imaging agents (cardiovascular disease), ImaginAb/GE Healthcare; PET radiotracer (prostate cancer), Johns Hopkins University School of Medicine; PET radiotracer (solid tumors), MD Anderson Cancer Center; phosphodiesterase 10 imaging agent (PET, neurological disorders), Institute for Neurodegenerative Disorders; PIMBA; Quantison; QW-7437; radiolabeled anti-CEACAM6 antibodies (imaging/cancer), NIH; radiolabeled anti-PSMA huJ591 minibodies (prostate cancer), ImaginAb; radiolabeled onartuzumab (imaging, cancer), Genentech; radiolabeled sigma-2 receptor ligands (solid tumor), Washington University in St Louis; radiolabeled WC-10 (neurological disease), Washington University; radiolabelled-A20FMDV2; RESP-3000; RG-7334; SH-U-563; SonoRx; SR-4554; STARBURST dendrimer-based MRI contrast agents (cardiovascular disease/ovary cancer), Dendritic Nanotechnology; sulphur hexafluoride microbubble ultrasound agent, Bracco; tau-binding PET tracer (Alzheimer disease), Siemens; T-cell co-receptor targeting PET imaging agent (antibody fragment, cancer/inflammation/transplantation), ImaginAb; technetium Tc 99m etarfolatide; technetium Tc 99m tilmanocept; TF-2 plus diagnostic/therapeutic (cancer), Immunomedics; TKS-040; TRC-105; triiodobenzene contrast agents, Nycomed; VasoPET; VMAT2 ligands (CNS disorder imaging), Molecular NeuroImaging/Institute for Neurodegenerative Disorders; yttrium (90Y) clivatuzumab tetraxetan; and any combinations thereof.

A detectable response generally refers to a change in, or occurrence of, a signal that is detectable either by observation or instrumentally. In certain instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ). In certain other instances, the detectable response is radioactivity (i.e., radiation), including alpha particles, beta particles, nucleons, electrons, positrons, neutrinos, and gamma rays emitted by a radioactive substance such as a radionuclide.

Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol,* 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, *IEEE Transactions on Biomedical Engineering,* 48:1034-1041 (2001), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled aggregate. Positron emission tomography (PET) is another suitable technique for detecting radiation in a subject.

In some embodiments, the affinity ligand could be linked to a lipid moiety or any other moiety that can self-assemble to form a supramolecular structure. For example, the linker could be a chain of polyethylene glycol or any other hydrophilic moiety. In some embodiments, the lipid can be a cholesterol and the linker can be a PEG chain of length 30-60 to which an antibody can be coupled via the affinity ligand. The resulting compound self-assembles into a supramolecular structure for improved antibody delivery to target cells.

Yet another aspect of the invention is directed to a method of treating cancer or metastasis. The method includes administering to a subject in need thereof an effective amount of the conjugate described herein.

For administration to a subject, the conjugates described herein can be provided in pharmaceutically acceptable compositions. These pharmaceutically acceptable compositions comprise a therapeutically-effective amount of one or more of the conjugates described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 353,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of cancer or metastasis.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with inflammation.

In addition, the methods described herein can be used to treat domesticated animals and/or pets. A subject can be male or female. A subject can be one who has been previously diagnosed with or identified as suffering from or having a disorder a cancer or metastasis, but need not have already undergone treatment.

The conjugates of the invention are also useful in combination with known anti-cancer treatments, including radiation. The methods of the invention are especially useful in combination with anti-cancer treatments that involve administering a second drug that acts in a different phase of the cell cycle.

Exemplary embodiments of the various aspects disclosed herein can be described by one or more of the following paragraphs:

1. A targeted drug delivery conjugate comprising:
   (i) a targeting ligand;
   (ii) an affinity ligand linked to said targeting ligand; and
   (iii) a therapeutic agent linked to said affinity ligand.
2. The targeted drug delivery conjugate of paragraph 1 wherein said affinity ligand is non-covalently connected to said targeting ligand.
3. The targeted drug delivery conjugate of paragraph 1 or 2, wherein said affinity ligand is non-covalently connected to said therapeutic agent.
4. The targeted drug delivery conjugate of paragraph 1 or 2 wherein said affinity ligand is covalently connected to said therapeutic agent.
5. The targeted drug conjugate of any of paragraphs 1-4, wherein said affinity ligand is connected to said therapeutic agent via a linker.
6. The targeted drug conjugate of paragraph 5, wherein the linker comprises a cleavable group.
7. The targeted drug delivery conjugate of any of paragraphs 1-6, wherein the targeting ligand is selected from the group consisting of monoclonal antibodies, polyclonal antibodies, antigens, folates, EGF, albumin, receptor ligands, carbohydrates, aptamers, integrin receptor ligands, chemokine receptor ligands, transferrin, biotin, serotonin receptor ligands, PSMA, endothelin, GCPII, somatostatin, LDL ligands, HDL ligands, polylysine (PLL), poly L-aspartic acid, poly L-glutamic acid, lectins, glycoproteins, surfactant protein A, mucin, transferrin, sugar-albumin conjugates, peptides (e.g., an alpha helical peptide, amphipathic peptide, RGD peptide, cell permeation peptide, endosomolytic/fusogenic peptide), transport/absorption facilitators (e.g., naproxen, aspirin, vitamin E, folic acid), hormones, multivalent carbohydrates, vitamins (e.g., vitamin A, vitamin E, vitamin K, vitamin B, e.g., folic acid, B12, riboflavin, biotin and pyridoxal), D-galactose, multivalent galactose, N-acetyl-D-galactose (GalNAc), multivalent GalNAc, D-mannose, multivalent mannose, multivalent lactose, N-acetyl-galactosamine, N-acetyl-glucosamine, multivalent fucose, glycosylated polyaminoacids, and any combinations thereof.
8. The targeted drug delivery conjugate of any of paragraphs 1-7, wherein the targeting ligand binds a protein, receptor, or marker expressed on the surface of a cancer cell.
9. The targeted drug delivery conjugate of any of paragraphs 1-8, wherein the affinity ligand binds with high affinity and/or specificity with the targeting ligand.
10. The targeted drug delivery conjugate of any of paragraphs 1-9, wherein the affinity ligand is selected from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.
11. The targeted drug delivery conjugate of any of paragraphs 1-10, wherein the affinity ligand is selected from the group consisting of 4-mercaptoethyl pyridine, triazines, 2-mercapto-5-benzymidazole sulfonic acid, peptides, protein A, protein G, protein L, protein A/G/L mimetics, domains and sub-domains, Fc receptor, Fc receptor mimetics, phenyl boronic acid, boronic acid derivatives, N-benzyl-N-methyl ethanolamine, N-benzoyl-homocysteine, TRIM21 and its mimetics, Clusterin and its mimetics, histidyl-aminohexyl based, 2-mercaptoimidazole, 2-mercapto-1-methyl-imidazole, 2-benzamido-4-mercaptobutanoic acid, phenylpropylamine, hexylamine, 3-(2-mercaptoethyl)quinazoline-2,4(1H,3H)dione, ficolin and its mimetics, 4'-terpyridinylsulfanylethylamine, 4-(1H-imidazol-1-yl) aniline, Poly(4-vinylpyridine), ligands used for antibody purification which specifically bind to antibodies non-covalently, any combinations or parts or modifications thereof.
12. The targeted drug delivery conjugate of any of paragraphs 1-11, wherein the linker is selected from the group consisting of a bond, hydrocarbons, amino acids, peptides, polyethylene glycols, cyclodextrin, and any derivatives and combinations thereof.
13. The targeted drug delivery conjugate of any of paragraphs 1-12, wherein the therapeutic agent is linked to the linker via a non-cleavable linking group.
14. The targeted drug delivery conjugate of any of paragraphs 1-13, wherein the therapeutic agent is linked to the linker via a cleavable linking group.
15. The targeted drug delivery conjugate of any of paragraphs 1-14, wherein the affinity ligand is linked to the linker via a non-cleavable linking group.
16. The targeted drug delivery conjugate of any of paragraphs 1-15, wherein the affinity ligand is linked to the linker via a cleavable linking group.
17. The targeted drug delivery conjugate of any of paragraphs 1-16, wherein the linker is a branched linker.
18. The targeted drug delivery conjugate of paragraph 17, wherein the conjugate comprises two or more affinity ligands linked to the therapeutic agent via the branched linker.
19. The targeted drug delivery conjugate of paragraph 18, wherein the two or more affinity ligands are different affinity ligands.
20. The targeted drug delivery conjugate of paragraph 18, wherein the two or more affinity ligands are the same.
21. The targeted drug delivery conjugate of paragraph 17, wherein the conjugate comprises at least two therapeutic agents linked to the affinity molecule via the branched linker.
22. The targeted drug delivery conjugate of paragraph 21, wherein the at least two therapeutic agents are different therapeutic agents.
23. The targeted drug delivery conjugate of paragraph 21, wherein the at least two therapeutic agents are the same.
24. The targeted drug delivery conjugate of any of paragraphs 1-23, wherein the therapeutic agent is an anti-cancer agent.
25. A conjugate comprising:
    (i) a first biomolecule;
    (ii) a first affinity ligand linked to said first biomolecule;
    (iii) a second affinity ligand linked to said first affinity molecule; and
    (iv) a second biomolecule linked to said second affinity ligand.
26. The conjugate of paragraph 25, wherein the first affinity ligand and the second affinity ligand are linked to each other via a linker.

27. The conjugate of paragraph 26, wherein the linker comprises a cleavable group.
28. The conjugate of paragraph 26 or 27, wherein the first affinity ligand is linked to the linker via a cleavable linking group.
29. The conjugate of any of paragraphs 26-28, wherein the second affinity ligand is linked to the linker via a cleavable linking group.
30. The conjugate of any of paragraphs 26-29, wherein the first affinity ligand is non-covalently linked to the first biomolecule.
31. The conjugate of any of paragraphs 26-30, wherein the second affinity ligand is non-covalently linked to the second biomolecule.
32. The conjugate of any of paragraphs 26-31, wherein the first biomolecule and/or the second biomolecule comprises a targeting ligand, a therapeutic agent or a combination thereof.
33. The conjugate of any of paragraphs 26-33, wherein the affinity ligand is selected from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.
34. The conjugate of any of paragraphs 26-33, wherein the affinity ligand is selected from the group consisting of 4-mercaptoethyl pyridine, triazines, 2-mercapto-5-benzymidazole sulfonic acid, peptides, protein A, protein G, protein L, protein A/G/L mimetics, domains and sub-domains, Fc receptor, Fc receptor mimetics, phenyl boronic acid, boronic acid derivatives, N-benzyl-N-methyl ethanolamine, N-benzoyl-homocysteine, TRIM21 and its mimetics, Clusterin and its mimetics, histidyl-aminohexyl based, 2-mercaptoimidazole, 2-mercapto-1-methyl-imidazole, 2-benzamido-4-mercaptobutanoic acid, phenylpropylamine, hexylamine, 3-(2-mercaptoethyl)quinazoline-2,4(1H,3H)dione, ficolin and its mimetics, 4'-terpyridinylsulfanylethylamine, 4-(1H-imidazol-1-yl) aniline, Poly(4-vinylpyridine), ligands used for antibody purification which specifically bind to antibodies non-covalently, any combinations or parts or modifications thereof.
35. The conjugate of any of paragraphs 26-34, wherein the linker is selected from the group consisting of a bond, hydrocarbons, amino acids, peptides, polyethylene glycols, cyclodextrin, and any derivatives and combinations thereof.
36. A conjugate comprising:
    (i) a first biomolecule;
    (ii) an affinity ligand linked to said first biomolecule; and
    (iii) a second biomolecule linked to said affinity ligand.
37. The conjugate of paragraph 36, wherein the affinity ligand is non-covalently connected to said second biomolecule.
38. The conjugate of paragraph 36, wherein the affinity ligand is covalently connected to said second biomolecule.
39. The conjugate of any of paragraphs 36-38, wherein the affinity ligand is linked to the second biomolecule via a linker.
40. The conjugate of paragraph 39, wherein the linker comprises a cleavable group.
41. The conjugate of paragraph 39 or 40, wherein the affinity ligand is linked to the linker via a cleavable linking group.
42. The conjugate of any of paragraphs 39-41, wherein the second biomolecule is linked to the linker via a cleavable linking group.
43. The conjugate of any of paragraphs 36-42, wherein the first biomolecule is non-covalently connected the affinity molecule.
44. The conjugate of any of paragraphs 36-43, wherein the first biomolecule and/or the second biomolecule comprises a targeting ligand, a therapeutic agent or a combination thereof.
45. The conjugate of any of paragraphs 36-44, wherein the affinity ligand is selected from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.
46. The conjugate of any of paragraphs 36-45, wherein the affinity ligand is selected from the group consisting of 4-mercaptoethyl pyridine, triazines, 2-mercapto-5-benzymidazole sulfonic acid, peptides, protein A, protein G, protein L, protein A/G/L mimetics, domains and sub-domains, Fc receptor, Fc receptor mimetics, phenyl boronic acid, boronic acid derivatives, N-benzyl-N-methyl ethanolamine, N-benzoyl-homocysteine, TRIM21 and its mimetics, Clusterin and its mimetics, histidyl-aminohexyl based, 2-mercaptoimidazole, 2-mercapto-1-methyl-imidazole, 2-benzamido-4-mercaptobutanoic acid, phenylpropylamine, hexylamine, 3-(2-mercaptoethyl)quinazoline-2,4(1H,3H)dione, ficolin and its mimetics, 4'-terpyridinylsulfanylethylamine, 4-(1H-imidazol-1-yl) aniline, Poly(4-vinylpyridine), ligands used for antibody purification which specifically bind to antibodies non-covalently, any combinations or parts or modifications thereof.
47. The conjugate of any of paragraphs 36-47, wherein the linker is selected from the group consisting of a bond, hydrocarbons, amino acids, peptides, polyethylene glycols, cyclodextrin, and any derivatives and combinations thereof.
48. A conjugate comprising at least two affinity ligands linked to a therapeutic agent, wherein said at least two affinity ligands are linked to the therapeutic agent via a branched linker.
49. The conjugate of paragraph 48, wherein said at least two affinity ligands are different affinity ligands.
50. The conjugate of any of paragraphs 48-49, wherein the therapeutic agent is an anticancer agent or a cytotoxic drug.
51. The conjugate of any of paragraphs 48-50, wherein said at least two affinity ligands are selected independently from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.
52. The conjugate of any of paragraphs 48-51, wherein said at least two affinity ligands are selected independently from the group consisting of 4-mercaptoethyl pyridine, triazines, 2-mercapto-5-benzymidazole sulfonic acid, peptides, protein A, protein G, protein L, protein A/G/L mimetics, domains and sub-domains, Fc receptor, Fc receptor mimetics, phenyl boronic acid, boronic acid derivatives, N-benzyl-N-methyl ethanolamine, N-benzoyl-homocysteine, TRIM21 and its mimetics, Clusterin and its mimetics, histidyl-aminohexyl based, 2-mercaptoimidazole, 2-mercapto-1-methyl-imidazole, 2-benzamido-4-mercaptobutanoic acid, phenylpropylamine, hexylamine, 3-(2-mercaptoethyl)quinazoline-2,4(1H,3H)dione, ficolin and its mimetics, 4'-terpyridinylsulfanylethylamine, 4-(1H-imidazol-1-yl) aniline, Poly(4-vinylpyridine), ligands used for antibody purification which specifically bind to antibodies non-covalently, any combinations or parts or modifications thereof.

53. The conjugate of any of paragraphs 48-52, wherein the linker is selected from the group consisting of a bond, hydrocarbons, amino acids, peptides, polyethylene glycols, cyclodextrin, and any derivatives and combinations thereof.
54. The conjugate of any of paragraphs 48-53, wherein the linker comprises a cleavable group.
55. The conjugate of any of paragraphs 48-54, wherein at least one of said at least two affinity ligands is linked to the linker via a cleavable linking group.
56. The conjugate of any of paragraphs 48-55, wherein the therapeutic agent is linked to the linker via a cleavable linking group.
57. The conjugate of any of paragraphs 48-56, wherein at least one of said at least two affinity ligands is linked to a targeting ligand.
58. The conjugate of paragraphs 48-57, wherein at least two of said at least affinity ligands are linked to a targeting ligand.
59. The conjugate of paragraphs 48-58, wherein at least two of said at least affinity ligands are linked to a same targeting ligand.
60. The conjugate of paragraphs 48-59, wherein at least one of said at least two affinity ligands is linked to a first targeting agent and at least one of said at least two affinity ligands is linked to a second targeting ligand, and wherein the first and second targeting ligands are different.
61. The conjugate of any of paragraphs 48-60, wherein the targeting ligand is selected from the group consisting of monoclonal antibodies, polyclonal antibodies, antigens, folates, EGF, albumin, receptor ligands, carbohydrates, aptamers, integrin receptor ligands, chemokine receptor ligands, transferrin, biotin, serotonin receptor ligands, PSMA, endothelin, GCPII, somatostatin, LDL ligands, HDL ligands, polylysine (PLL), poly L-aspartic acid, poly L-glutamic acid, lectins, glycoproteins, surfactant protein A, mucin, transferrin, sugar-albumin conjugates, peptides (e.g., an alpha helical peptide, amphipathic peptide, RGD peptide, cell permeation peptide, endosomolytic/fusogenic peptide), transport/absorption facilitators (e.g., naproxen, aspirin, vitamin E, folic acid), hormones, multivalent carbohydrates, vitamins (e.g., vitamin A, vitamin E, vitamin K, vitamin B, e.g., folic acid, B12, riboflavin, biotin and pyridoxal), D-galactose, multivalent galactose, N-acetyl-D-galactose (GalNAc), multivalent GalNAc, D-mannose, multivalent mannose, multivalent lactose, N-acetyl-galactosamine, N-acetyl-glucosamine, multivalent fucose, glycosylated polyaminoacids, and any combinations thereof.
62. The conjugate of any of paragraphs 48-61, wherein the targeting ligand binds a protein, receptor, or marker expressed on the surface of a cancer cell.
63. A pharmaceutical composition comprising a conjugate of any of paragraphs 1-62 and a pharmaceutically acceptable carrier.
64. A method of treating a cancer in a subject in need thereof, the method comprising administering an effective amount of a conjugate of any of paragraphs 1-62.

Figure 29:
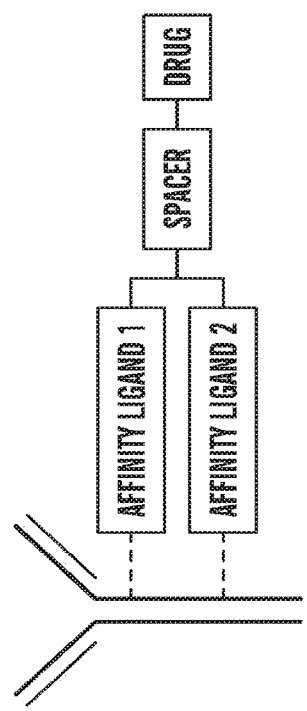
FIG. 29 shows an antibody linked to a cytotoxic drug via two affinity ligands.
Figure 30:
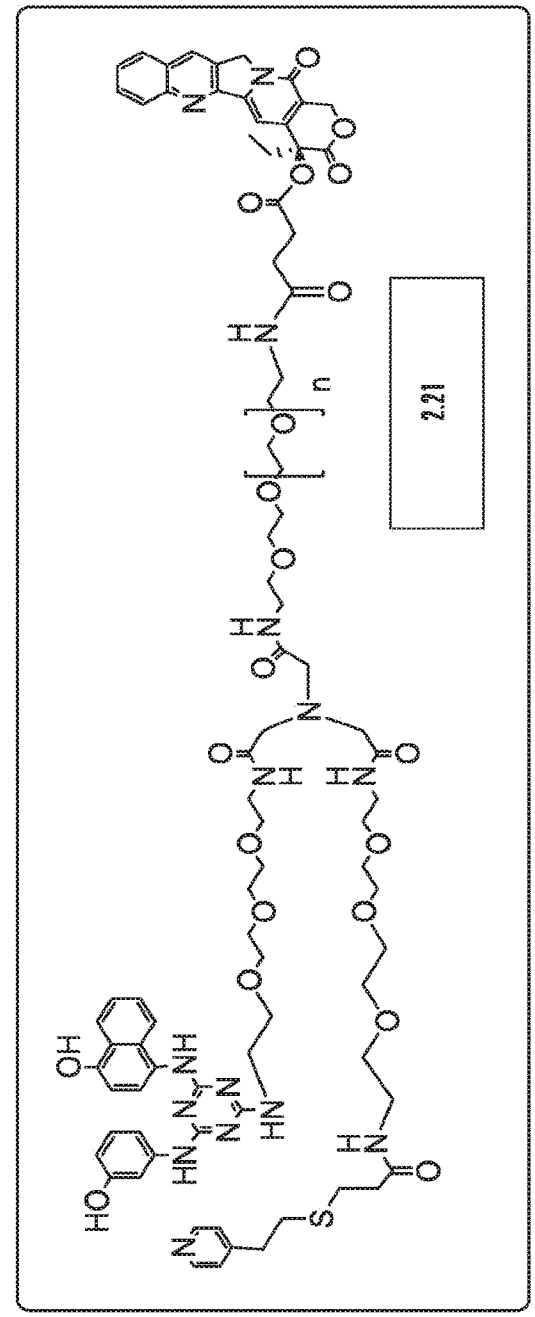
FIG. 30 shows the structure of compound 2.21 where camptothecin is linked to two different affinity ligands, 4-MEP and triazine moiety, via a spacer.

As shown in FIGS. 29 and 30, two or more affinity ligands can be linked to a therapeutic agent via a linker. For example, a branched linker can be used to connect two or more affinity ligands to a therapeutic agent. Without limitations, the affinity ligands can be the same or different. In some embodiments, the therapeutic agent can be a cytotoxic drug. The linker can be cleavable or non-cleavable.

Figure 31:
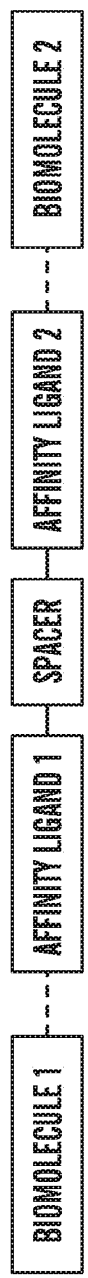
FIG. 31 shows two biomolecules linked via two affinity ligands.

Also provided herein are conjugates that comprise two or more affinity ligands connected together via a linker. In some embodiments, one or more affinity ligands can be used to link biomolecules. The affinity ligands can be same or different. The linker can be cleavable or non-cleavable. The biomolecules can be same or different. (FIG. 31)

In some embodiments, the conjugate comprises: (i) a first biomolecule; (ii) a first affinity ligand linked to said first biomolecule; (iii) a second affinity ligand linked to said first affinity molecule; and (iv) a second biomolecule linked to said second affinity ligand. Without limitations the first and the second biomolecule can be the same or different. Further, the first and the second affinity ligands can be the same or different.

In the conjugate of above paragraph, the first affinity ligand can be non-covalently linked to the first biomolecule. Independently, the second affinity ligand can be non-covalently linked to the second biomolecule In some embodiments of the above conjugate, the first affinity ligand and the second affinity ligand are linked to each other via a linker. The linker can be cleavable or non-cleavable. Accordingly, in some embodiments, the linker comprises a cleavable group. In some embodiment, the first and/or the second affinity ligand can be linked to the linker via a cleavable linking group.

Figure 32:
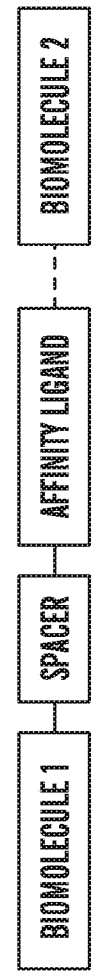
FIG. 32 shows two biomolecules linked via an affinity ligand where one biomolecule is linked via covalent bond and other by non-covalent bond.

In some embodiments of the various aspects disclosed herein, an affinity ligand is used to link two or more biomolecules. One biomolecule can be covalently linked to a linker and the second biomolecule can be linked via non-covalent interactions. The linker can be cleavable or non-cleavable. The biomolecules can be same or different. (FIG. 32)

Accordingly, in one aspect the disclosure provides a conjugate comprising: (i) a first biomolecule; (ii) an affinity ligand linked to said first biomolecule; and (iii) a second biomolecule linked to said affinity ligand. Without limitations the first and the second biomolecule can be the same or different. Further, the first biomolecule can be non-covalently connected to the affinity molecule.

In the conjugate of the above paragraph, the affinity ligand can be non-covalently connected to said second biomolecule. In some embodiments, the affinity ligand can be covalently connected to said second biomolecule.

In some embodiments, the affinity ligand can be linked to the second biomolecule via a linker. Without limitations the linker can be cleavable or non-cleavable. Accordingly, in some embodiments, the linker comprises a cleavable group. In some embodiments, the affinity ligand can be linked to the linker via a cleavable linking group. In some embodiments, the second biomolecule can be linked to the linker via a cleavable linking group.

As defined herein, a biomolecule is any molecule present in living organisms or a molecule which can engage in a biological activity or is effective in modulating a biological activity. Exemplary biomolecules include macromolecules (e.g., proteins, peptides, enzymes, antibodies, polysaccharides, polynucleotides), and small molecules (e.g., amino acids, monosaccharides, lipids, nucleic acids, vitamins, hormones, neurotransmitters, metabolites). In some embodiments, the biomolecule comprises a therapeutic agent as defined herein, a targeting ligand as defined herein, or a combination thereof.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like. Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynols that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain. For example, $C_1$-$C_6$ alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like.

As used herein, the term "alkylidene" means a straight or branched unsaturated, aliphatic, divalent radical having a general formula =CR$_a$R$_b$. $C_x$ alkylidene and $C_x$-$C_y$ alkylidene are typically used where X and Y indicate the number of carbon atoms in the chain. For example, $C_2$-$C_6$ alkylidene includes methylidene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$) alkyl includes chloromethyl, dichloromethyl, difluoromethyl, trifluoromethyl (—CF$_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisothiazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heteroaryl and $C_x$-$C_y$ heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$ cyclyl and $C_x$-$C_y$ cyclyl are typically used where X and Y indicate the number of carbon atoms in the ring system. The cycloalkyl group additionally can be optionally substituted, e.g., with 1, 2, 3, or 4 substituents. $C_3$-$C_{10}$ cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heterocyclyl and $C_x$-$C_y$ heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, —NR$^N$—, —N$^+$(O$^-$)═, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or hetero-cyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like. The term "alkoxycarbonyl" means —C(O)O-(alkyl), such as —C(═O)OCH$_3$, —C(═O)OCH$_2$CH$_3$, and the like. The term "alkoxyalkyl" means -(alkyl)-O-(alkyl), such as —CH$_2$OCH$_3$, —CH$_2$OCH$_2$CH$_3$, and the like. The term "aryloxy" means —O-(aryl), such as —O-phenyl, —O-pyridinyl, and the like. The term "arylalkyl" means -(alkyl)-(aryl), such as benzyl (i.e., —CH$_2$phenyl), —CH$_2$-pyridinyl, and the like. The term "arylalkyloxy" means —O-(alkyl)-(aryl), such as —O-benzyl, —O—CH$_2$-pyridinyl, and the like. The term "cycloalkyloxy" means —O-(cycloalkyl), such as —O-cyclohexyl, and the like. The term "cycloalkylalkyloxy" means —O-(alkyl)-(cycloalkyl), such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like. The term "mono- or di-alkylamino" means —NH(alkyl) or —N(alkyl)(alkyl), respectively, such as —NHCH$_3$, —N(CH$_3$)$_2$, and the like. The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like. The term "arylamino" means —NH(aryl), such as —NH-phenyl, —NH-pyridinyl, and the like. The term "arylalkylamino" means —NH-(alkyl)-(aryl), such as —NH-benzyl, —NHCH$_2$-pyridinyl, and the like. The term "cycloalkylamino" means —NH-(cycloalkyl), such as —NH-cyclohexyl, and the like. The term "cycloalkylalkylamino"—NH-(alkyl)-(cycloalkyl), such as —NHCH$_2$-cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH$_3$) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

The term "optionally substituted" means that the specified group or moiety is unsubstituted or is substituted with one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted.

The term "substituent" refers to a group "substituted" on the substituted entity at any atom of that entity. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some embodiments, the substituent group is selected from alkyl, ester, amide, monocarbonyl, dicarbonyl, ketones, aldehydes, and the like.

As used herein, the term "anti-cancer activity" or "anti-cancer properties" refers to the inhibition (in part or in whole) or prevention of unregulated cell growth and/or the inhibition (in part or in whole) or prevention of a cancer as defined herein. Anticancer activity includes, e.g., the ability to reduce, prevent, or repair genetic damage, modulate undesired cell proliferation, modulate misregulated cell death, or modulate mechanisms of metastasis (e.g., ability to migrate).

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. Metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including Glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

As used herein, the term "cancer" includes, but is not limited to, solid tumors and blood borne tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The compounds of the invention are useful for treating patients who have been previously treated for cancer, as well as those who have not previously been treated for cancer. Indeed, the methods and compositions of this invention can be used in first-line and second-line cancer treatments.

In some embodiments, the cancer or metastasis is selected from the group consisting of platinum susceptible or resistant tumors including breast, head and neck, ovarian, testicular, pancreatic, oral-esophageal, gastrointestinal, liver, gall bladder, lung, melanoma, skin cancer, sarcomas, blood cancers, brain tumors including glioblastomas, and tumors of neuroectodermal origin.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

As used herein, amino acids include natural or unnatural amino acids. Thus, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways. Exemplary amino acids amenable to the present invention include, but are not limited to, alanine; argnine; asparagine; aspartic acid; cysteine; glutamic acid; glutamine; glycine; histadine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; gamma-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (<Glu); α-aminoisobutyric acid (αAib); γ-aminobutyric acid (γAbu); α-aminobutyric acid (αAbu); αγ-aminobutyric acid (αγAbu); 3-pyridylalanine (Pal); Isopropyl-α-N$^ε$-lysine (ILys); Napthyalanine (Nal); α-naphtyalanine (α-Nal); β-napthyalanine (β-Nal); Acetyl-β-napthyalanine (Ac-β-napthyalanine); □napthyalanine; N$^ε$-picoloyl-lysine (PicLys); 4-halo-Phenyl; 4-pyrolidylalanine; isonipecotic carboxylic acid (inip); beta-amino acids; and isomers, analogs and derivatives thereof. One of skill in the art would know that this definition includes, D- and L-amino acids, alpha- and beta-amino acids, chemically modified amino acids, naturally occurring non-proteogenic amino acids, rare amino acids, and chemically synthesized compounds that have properties known in the art to be characteristic of an amino acid.

Peptide modifications are well known in the art. Thus, a peptide described herein, e.g., a linker peptide, can comprise one or more peptide modifications known in the art. Exemplary peptide modifications for modifying the fusion protein described herein include, but are not limited to, D amino acids, a amino acids, β amino acids, non-amide or modified amide linkages, chemically modified amino acids, naturally occurring non-proteogenic amino acids, rare amino acids, chemically synthesized compounds that have properties known in the art to be characteristic of an amino acid, and the like. Thus, as used herein, peptide includes natural or unnatural amino acids, or a combination thereof.

As used herein, the term "polyethylene glycol" or "PEG" means an ethylene glycol polymer that contains about 2 to about 2000000 linked monomers, typically about 50-1000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

As used herein, the term "antibody-based binding moiety" or "antibody" can include immunoglobulin molecules and immunologically active determinants of immunoglobulin molecules, e.g., molecules that contain an antigen binding site which specifically binds to the fusion protein. The term "antibody-based binding moiety" is intended to include whole antibodies, e.g., of any isotype (IgG, IgA, IgM, IgE, etc), and includes fragments thereof which also specifically bind with the fusion protein or a fragment thereof. Antibodies can be fragmented using conventional techniques. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-based binding moiety" includes polyclonal, monoclonal, or other purified preparations of antibodies and recombinant antibodies. The term "antibody-based binding moiety" is further intended to include humanized antibodies, bispecific antibodies, and chimeric molecules having at least one antigen binding determinant derived from an antibody molecule.

As used herein, the term "small molecule" refers to a molecule typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is highly preferred that a small molecule have a molecular mass equal to or less than 700 Daltons.

As used herein, the term "peptide" is used in its broadest sense to refer to compounds containing two or more amino acids, amino acid equivalents or other non-amino groups joined to each other by peptide bonds or modified peptide bonds. Peptide equivalents can differ from conventional peptides by the replacement of one or more amino acids with related organic acids (such as PABA), amino acids or the like or the substitution or modification of side chains or functional groups. A peptide can be of any size. Additionally, the peptide can be linear or cyclic.

In addition, the term "peptide" broadly includes proteins, which generally are polypeptides. As used herein, the term "protein" is used to describe proteins as well as fragments thereof. Thus, any chain of amino acids that exhibits a three dimensional structure is included in the term "protein", and protein fragments are accordingly embraced.

A peptidomimetic is a molecule capable of folding into a defined three-dimensional structure similar to a natural peptide.

As used herein, the term "nucleic acid" refers to a polymers (polynucleotides) or oligomers (oligonucleotides) of nucleotide or nucleoside monomers consisting of naturally occurring bases, sugars and intersugar linkages. The term "nucleic acid" also includes polymers or oligomers comprising non-naturally occurring monomers, or portions thereof, which function similarly. Such modified or substituted nucleic acids are often preferred over native forms because of properties such as, for example, enhanced cellular uptake and increased stability in the presence of nucleases. A nucleic acid can be single-stranded or double-stranded. A single-stranded nucleic acid can have double-stranded regions and a double-stranded nucleic acid can have single-stranded regions.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Synthesis of Conjugate 2.14 Shown in FIG. 19

Figure 19:
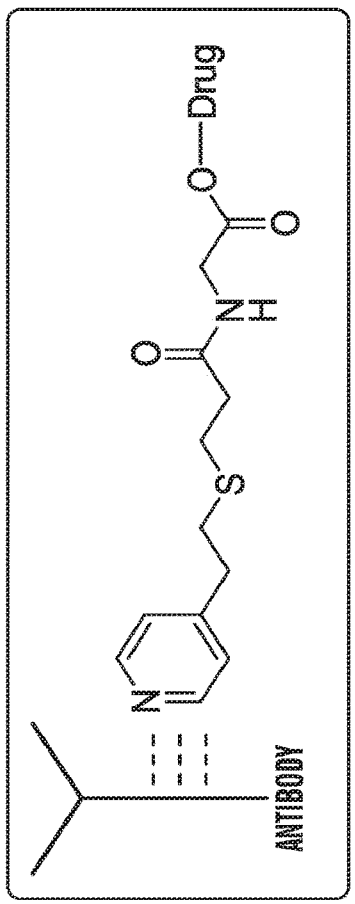

Conjugate 2.14, shown in FIG. 19, can be synthesized as outlined in Scheme 1.

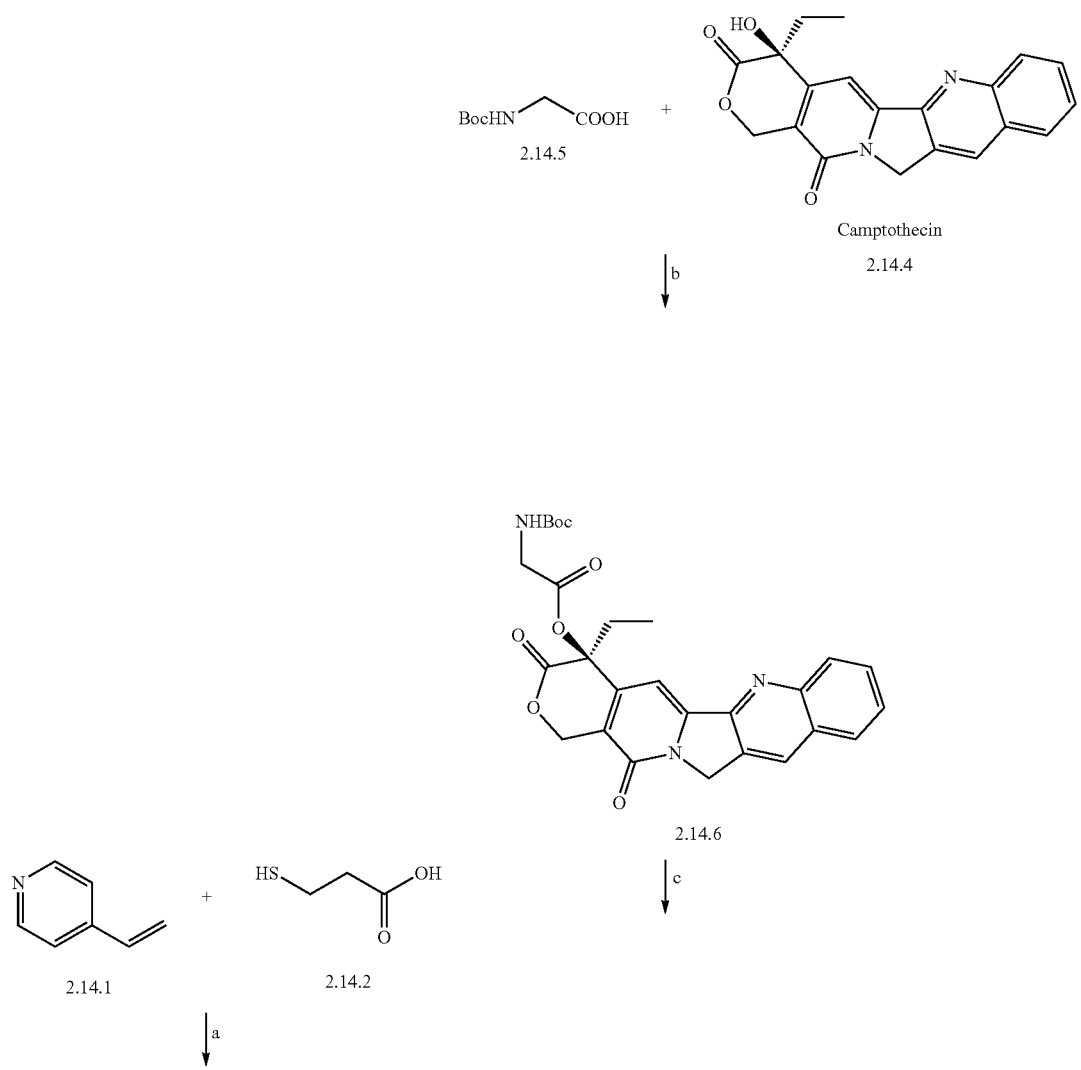

-continued

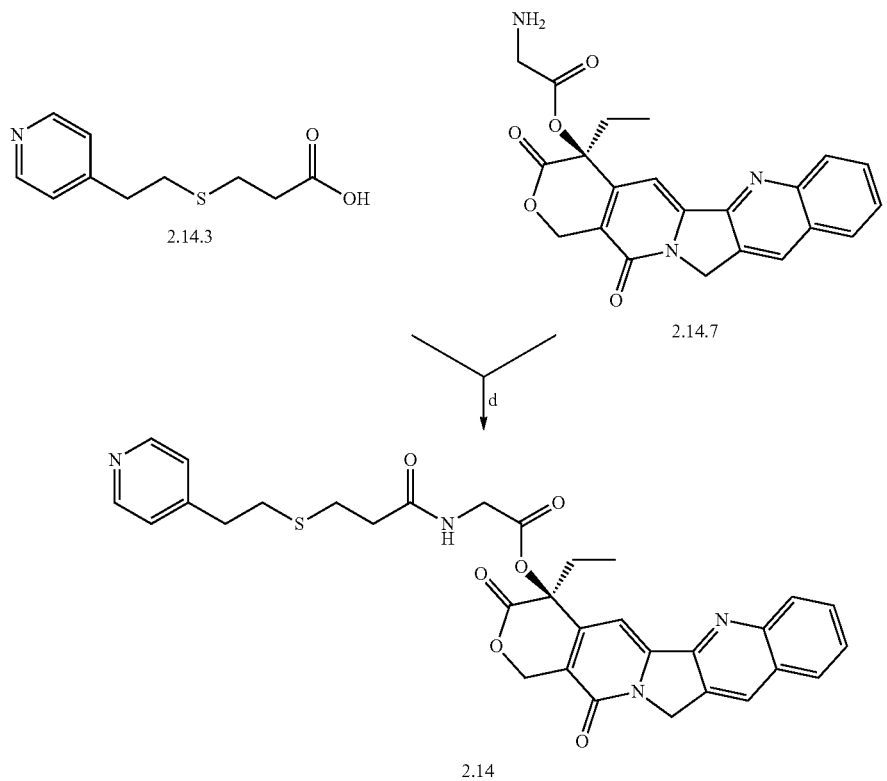

Scheme 1: Reagents and conditions: (a) Neat, 85° C., to 50° C., 30 minutes (b) DIPC, DMAP, CH2Cl2, 6 h (c) TFA, CH2Cl2, 0° C., 2 h (d) intermediate 2.14.7, DCC, DMAP, CH2Cl2, 3 h Step A:
In a 50 mL single-neck round-bottom flask, 4-Vinyl pyridine (2.14.1) (5 g, 47.5 mmol) and 3-Mercapto propionic acid (2.14.2) (5.05 g, 47.5 mmol) are taken under nitrogen atmosphere without addition of solvent and are heated at 85° C. for 0.5 h. The reaction mixture is cooled to 50° C. and water is added. The solid residue is filtered and washed successively with water and toluene to obtain product (2.14.3).

Step B:
In a 50 mL single-neck round-bottom flask, BocHNCH$_2$COOH (2.14.5) (75.4 mg, 0.430 mmol) is taken in dichloro methane (5 mL) under nitrogen atmosphere. DIPC (54.2 mg, 0.430 mmol) and DMAP (17.4 mg, 0.143 mmol) are added successively to the reaction mixture and stirred for 30 minutes at the same temperature. To this activated acid solution, camptothecin (100 mg, 0.287 mmol) is added and stirred at room temperature for 12 h and TLC is checked. After completion, the reaction mixture is quenched with water, extracted with chloroform, dried over anhydrous Na$_2$SO$_4$ and concentrated. The residue is purified by silica gel chromatography utilizing methanol-chloroform as eluent to obtain intermediate (2.14.6).

Step C:
In a 50 mL single-neck round-bottom flask, Boc-protected intermediate (2.14.6) (50 mg, 0.099 mmol) is taken in DCM and cooled to 0° C. To this solution TFA is added and stirred for 3 h at same temperature. After completion, the reaction mixture is concentrated under rotary evaporator and the crude product (2.14.7) is utilized for the next reaction without further purification.

Step D:
In a 50 mL single-neck round-bottom flask, acid intermediate (2.14.3) (27 mg, 0.128 mmol) is taken in DCM (5 mL) under Nitrogen atmosphere. DIPC (16 mg, 0.128 mmol) and DMAP (15 mg, 0.128 mmol) are added successively to the reaction mixture at the same temperature. To this activated acid solution, intermediate (2.14.7) (45 mg crude, 0.099 mmol) is added and stirred at room temperature for additional 12 h and TLC is checked. After completion, the reaction mixture is quenched with water; extracted with chloroform, dried over anhydrous Na$_2$SO$_4$ and concentrated. The solid residue is purified by neutral alumina utilizing methanol-chloroform as eluent to obtain pure final product (2.14).

Figure 23:
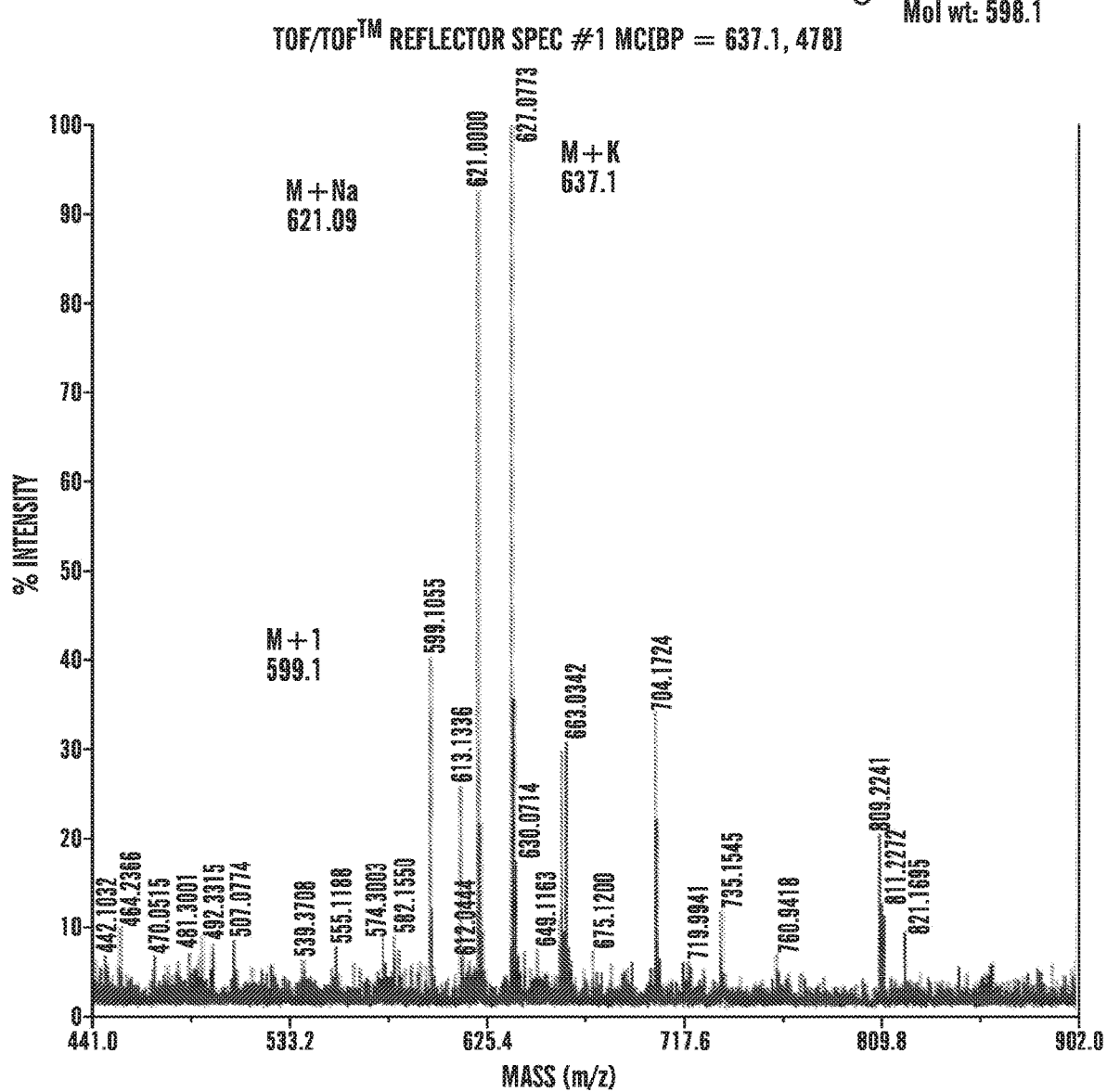
FIG. 23 shows the mass-spec of the crude mixture confirming the formation of compound 2.14.
Figure 24:
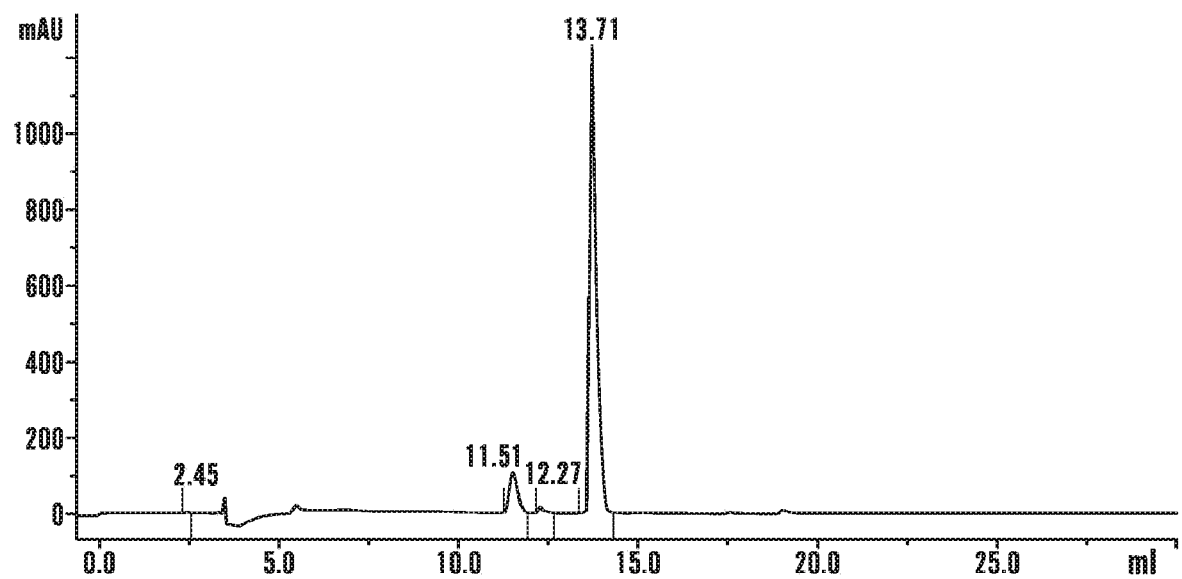
FIG. 24 shows the HPLC profile of the purified compound 2.14.
Figure 25:
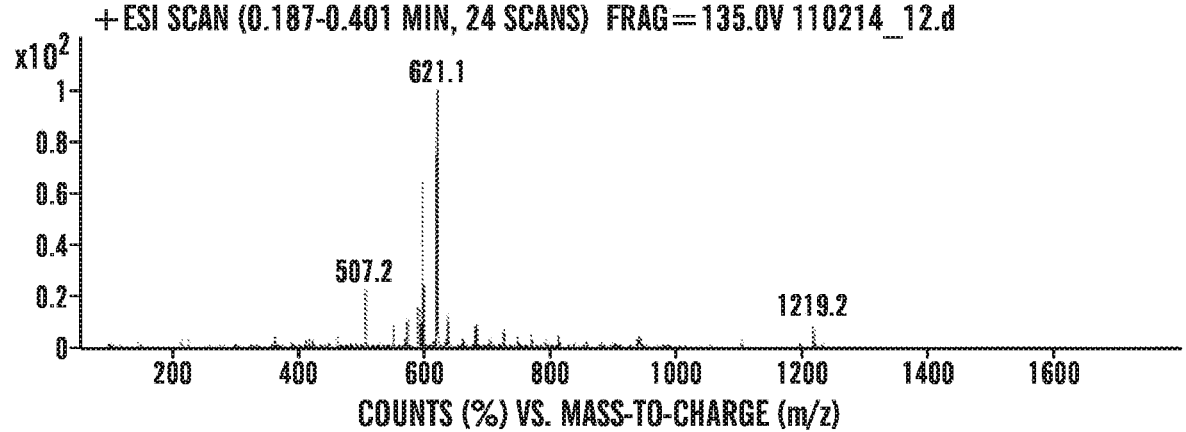
FIG. 25 shows the mass-spec data of the purified compound 2.14.

Compound 2.14 has been synthesized using the above described procedure and purified on semi-preparative HPLC system using reverse phase column. FIG. 23 shows the mass-spec [MALDI-TOF MS] of crude reaction mixture confirming the formation of compound 2.14. Calculated mass: C$_{32}$H$_{30}$N$_4$O$_6$S=598.19. Observed value 599.1 (M+H)$^+$, 621.09 (M+Na)$^+$, 637.1 (M+K)$^+$. FIG. 24 shows the HPLC profile of the purified compound 2.14 on C18 column using water/ACN gradient. Wavelength: 250 nm. Purity: 90%. FIG. 25 shows the mass-spec [ESI MS] data of the purified compound 2.14. Calculated mass: C$_{32}$H$_{30}$N$_4$O$_6$S=598.19. Observed value 599.1 (M+H)$^+$, 621.1 (M+Na)$^+$, 637.1 (M+K)$^+$.

Figure 22:
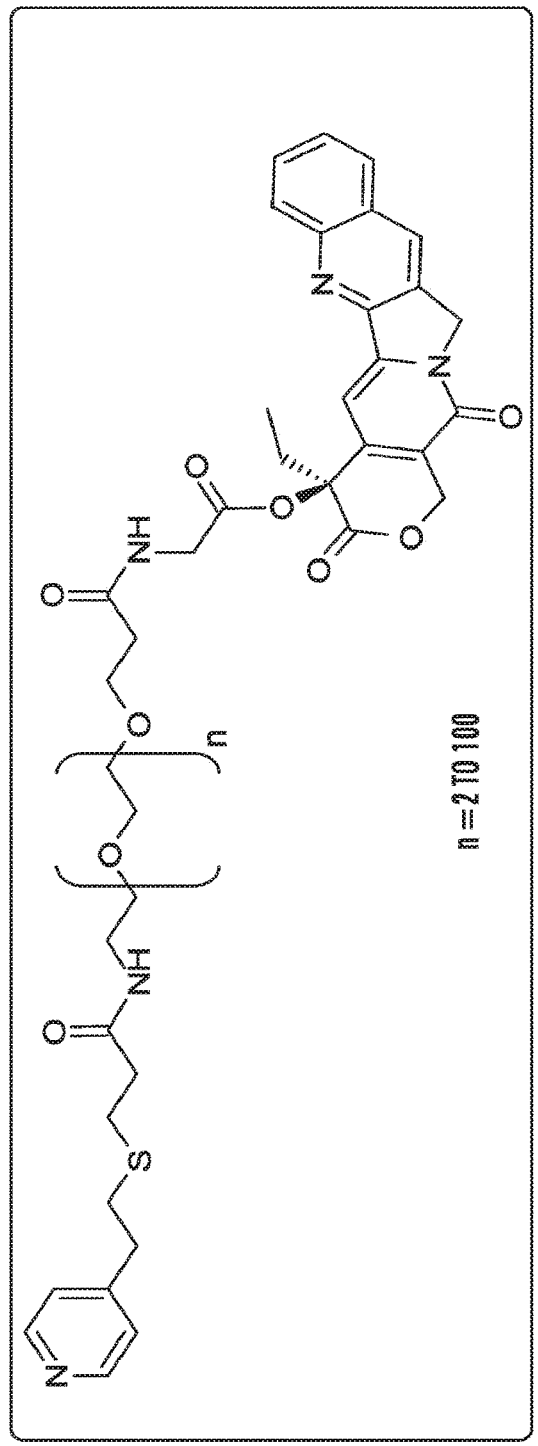
FIG. 22 (2.17) shows 4-MEP linked to a cytotoxic drug, camptothecin, via a PEG spacer, with peptide bond on both ends, and cleavable peptide linker.

Example 2: Synthesis of Conjugate 2.17
Conjugate 2.17, shown in FIG. 22, can be synthesized as outlined in Scheme 2.
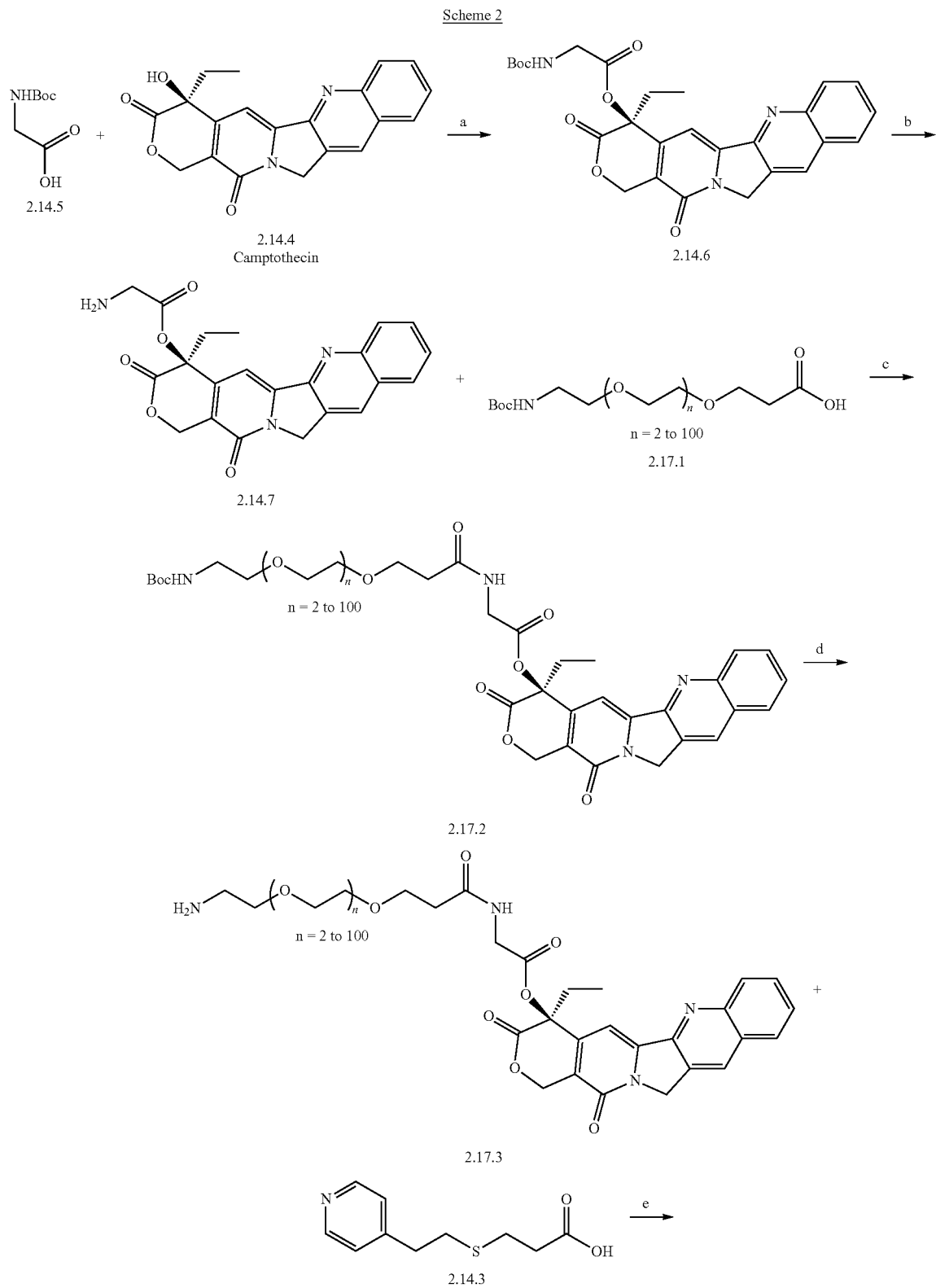

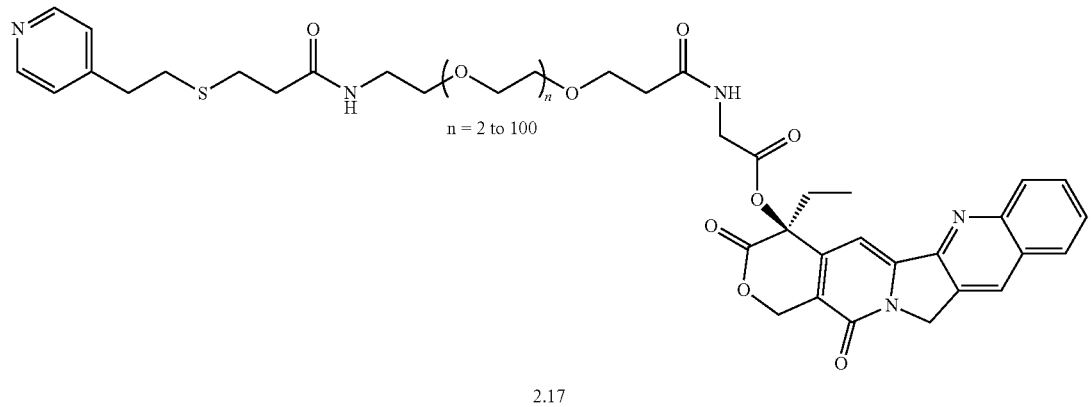

2.17

Reagents and conditions: (a) DIPC, DMAP, CH2Cl2, 12 h (b) TFA, CH2Cl2, 0° C. to r.t., 3 h.
(c) DIPC, DMAP, CH2Cl2, 12 h (d) TFA, CH2Cl2, 0° C. to r.t., 3 h. (e) DIPC, DMAP, CH2Cl2, 3 h Step A:

In a 50 mL single-neck round-bottom flask, BocHNCH$_2$COOH (2.14.5) is taken in dichloro methane (5 mL) under nitrogen atmosphere. DIPC and DMAP are added successively to the reaction mixture and stirred for 30 minutes at the same temperature. To this activated acid solution, camptothecin (2.14.4) is added and stirred at room temperature for 12 h and TLC is checked. After completion, the reaction mixture is quenched with water, extracted with chloroform, dried over anhydrous Na$_2$SO$_4$ and concentrated. The residue is purified by silica gel chromatography utilizing methanol-chloroform as mobile phase to obtain intermediate (2.14.6).

Step B:

In a 50 mL single-neck round-bottom flask, Boc-protected intermediate (2.14.6) is taken in DCM and cooled to 0° C. To this solution TFA is added and stirred for 3 h at same temperature. After completion, the reaction mixture is concentrated under rotary evaporator and the crude product (2.14.7) is utilized for the next reaction without further purification.

Step C:

In a 50 mL single-neck round-bottom flask, acid intermediate 2.17.1 is taken in dichloro methane under nitrogen atmosphere. DIPC and DMAP (17.4 mg, 0.143 mmol) are added successively to the reaction mixture and stirred for 30 minutes at the same temperature. To this activated acid solution, camptothecin amine (2.14.7) is added and stirred at room temperature for 12 h and TLC is checked. After completion, the reaction mixture is quenched with water, extracted with chloroform, dried over anhydrous Na$_2$SO$_4$ and concentrated. The residue is purified by silica gel chromatography utilizing methanol-chloroform as mobile phase to obtain intermediate (2.17.2).

Step D:

In a 50 mL single-neck round-bottom flask, Boc-protected intermediate (2.17.2) is taken in dichloro methane and cooled to 0° C. To this solution TFA is added and stirred for 3 h at same temperature. After completion, the reaction mixture is concentrated under rotary evaporator and the crude product (2.17.3) is utilized for the next reaction without further purification.

Step E:

In a 50 mL single-neck round-bottom flask, acid intermediate 2.14.3 is taken in dichloro methane under nitrogen atmosphere. DIPC and DMAP are added successively to the reaction mixture and stirred for 30 minutes at the same temperature. To this activated acid solution, amine intermediate 2.17.3 is added and stirred at room temperature for 12 h and TLC is checked. After completion, the reaction mixture is quenched with water, extracted with chloroform, dried over anhydrous Na$_2$SO$_4$ and concentrated. The residue is purified by silica gel chromatography utilizing methanol-chloroform as mobile phase to obtain final product (2.17).

Example 3: Synthesis of Conjugate 2.15

Figure 20:
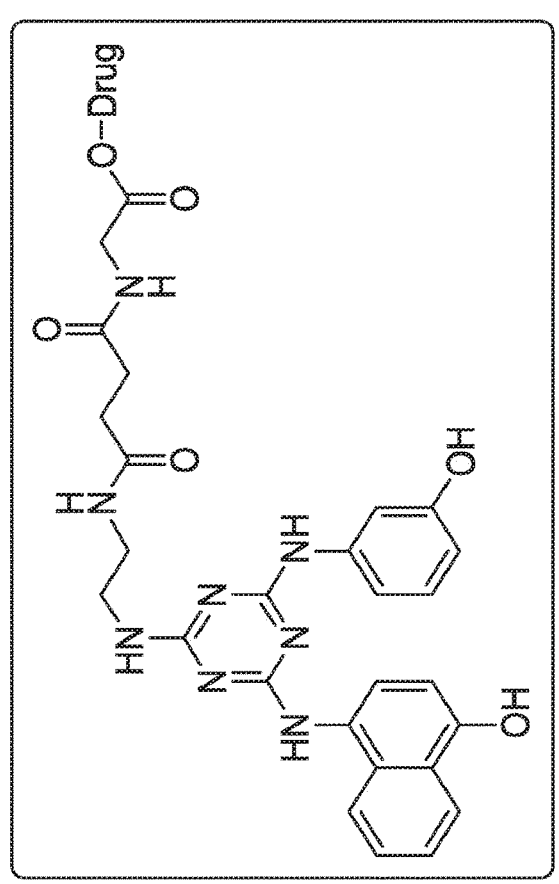

Conjugate 2.15, shown in FIG. 20, can be synthesized as outlined in Scheme 3.

Step A:

In a 50 mL single-neck round-bottom flask, triazine (2.15.1) is taken in anhydrous dichloro methane (5 mL) under nitrogen atmosphere. The reaction mixture is cooled under ice bath and diisopropyl ethyl amine is added. To this solution, succinic anhydride (2.15.2) is added and stirred at room temperature for additional 6 h and TLC is checked. After completion, the reaction mixture is quenched with water, extracted with chloroform, dried over anhydrous Na$_2$SO$_4$ and concentrated under vacuum. The residue is purified by neutral alumina utilizing methanol-chloroform solution as eluent to obtain intermediate (2.15.3).

Scheme 3
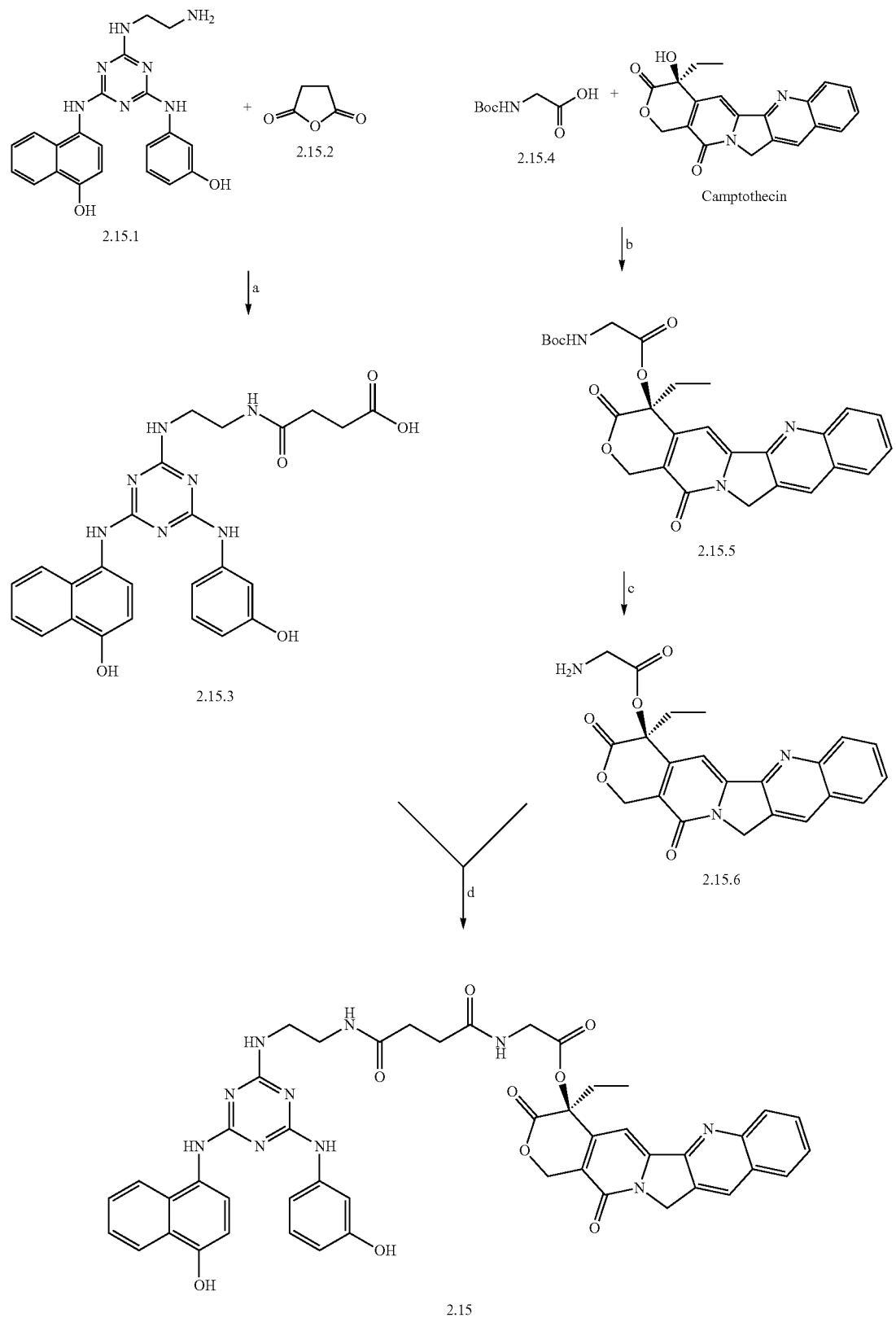
2.15
Scheme 3: Reagents and conditions: (a) DIPEA, CH2Cl2, 12 h (b) DIPC, DMAP, CH2Cl2, 12 h (c) TFA, CH2Cl2, 3 h (d) Drug, DCC, DMAP, CH2Cl2, 12 h Step B:

In a 50 mL single-neck round-bottom flask, BocHNCH₂COOH (2.15.4) is taken in anhydrous dichloro methane under nitrogen atmosphere. DIPC and DMAP are added successively to the reaction mixture at 0° C. and stirred for 30 minutes. To this activated acid solution, camptothecin is added and stirred at room temperature for additional 12 h and TLC is checked. After completion, the reaction mixture is quenched with water, extracted with chloroform, dried over anhydrous Na₂SO₄ and concentrated in vacuum. The solid residue is purified by silica gel chromatography utilizing methanol-chloroform solution as eluent to obtain intermediate (2.15.5).

Step C:

In a 50 mL single-neck round-bottom flask, Boc protected glycine (2.14.5) is taken in dichloro methane under nitrogen atmosphere and cooled to 0° C. To this solution, TFA is added and stirred at same temperature for 3 h. After completion, the reaction mixture is concentrated under rotary evaporator and the crude product (2.15.6) is utilized for the next reaction without further purification.

Step D:

In a 50 mL single-neck round-bottom flask, acid intermediate (2.15.3) is taken in dichloro methane under nitrogen atmosphere. DIPC and DMAP are added successively to the reaction mixture at 0° C. and stirred for 30 minutes. To this activated acid solution, amine intermediate (2.15.6) is added and stirred at room temperature for additional 12 h and TLC is checked. After completion, the reaction mixture is quenched with water, extracted with chloroform, dried over anhydrous Na₂SO₄ and concentrated in vacuum. The solid residue is purified by neutral alumina utilizing methanol-chloroform solution as eluent to obtain pure final product (2.15).

Example 4: Synthesis of Conjugate 2.16

Figure 21:
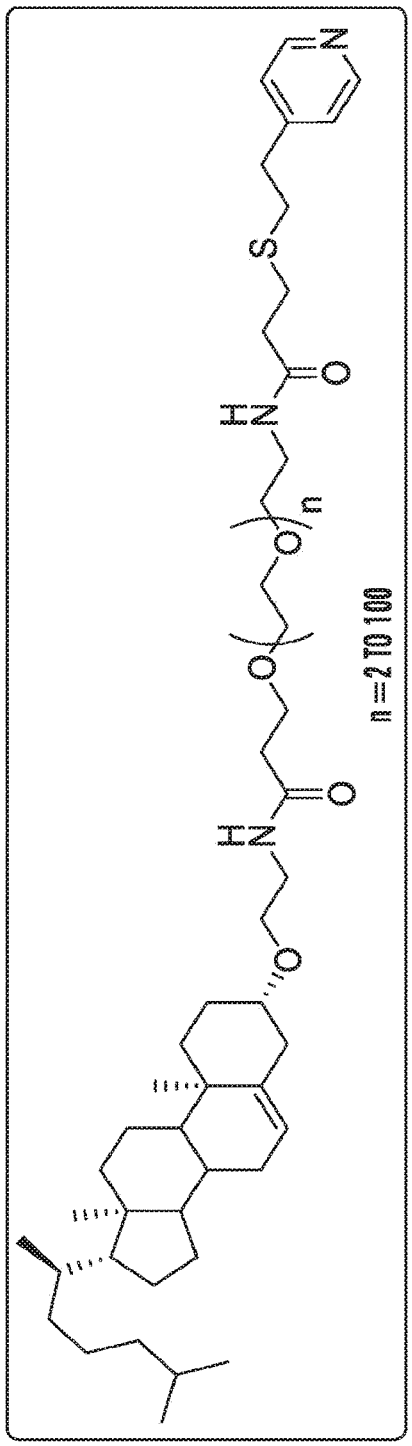
FIG. 21 (2.16) shows 4-MEP linked to a lipid moiety, cholesterol, via a PEG spacer, with peptide bond on both ends.

Conjugate 2.16, shown in FIG. 21, can be synthesized as outlined in Schemes 4 and 5.

Step A:

To an ice cooled solution of cholesterol (10 g, 0.026 mol, 2.16.1) in 45 ml CH₂Cl₂, 15 ml pyridine is added and stirred for about 15 minutes. To this solution, p-toluene sulphonyl chloride (9.8 g, 0.052 mol) is added and stirred for about 6 h at about 0° C. and thereafter, TLC is checked. After completion, the reaction mixture is diluted with CHCl₃ (20 mL) and washed with 1N HCl (3×50 mL) and brine (20 mL) successively. The organic layer is dried over anhydrous Na₂SO₄ and concentrated under vacuum to give intermediate 2.16.2 and the said intermediate is directly taken for the next reaction without further purification.

Step B:

To the solution of tosylated cholesterol 2.16.2 (10 g, 0.018 mol) in 45 ml dioxane, 15 ml ethylene glycol is added and refluxed for about 4 h and the TLC is checked. After completion, the reaction mixture is extracted with ethyl acetate and washed with water (3×50 mL) and brine (20 mL) successively. The organic layer is dried over anhydrous Na₂SO₄ and concentrated under vacuum and column purified to give intermediate 2.16.3.

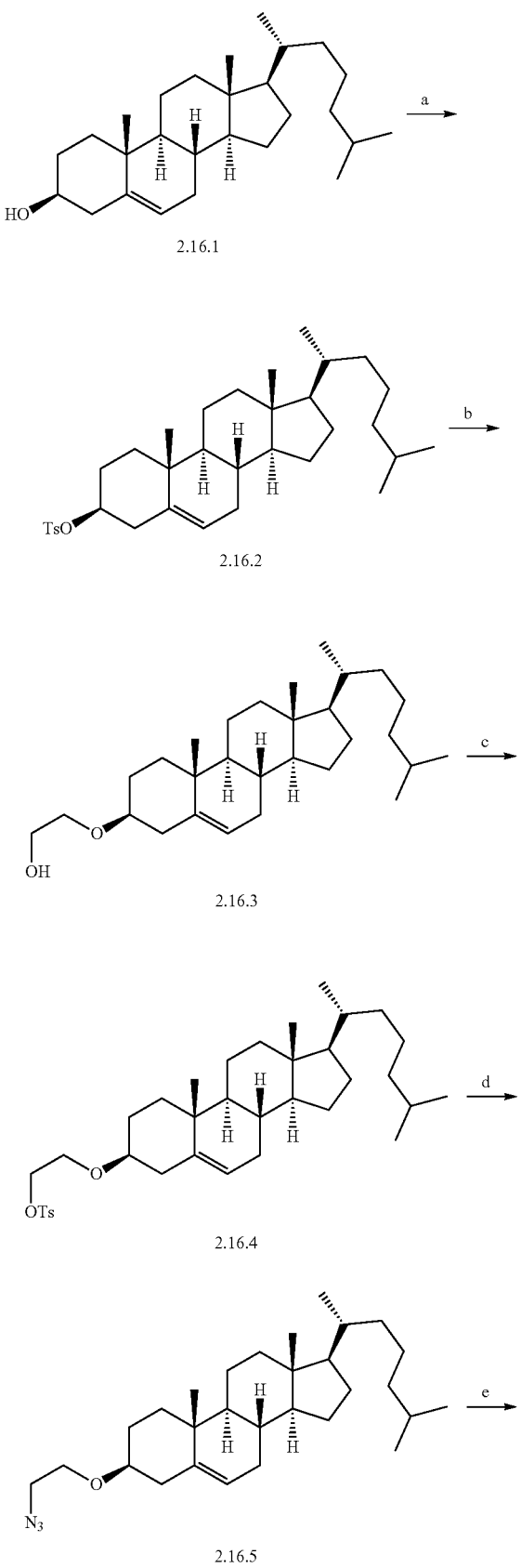

Scheme 4

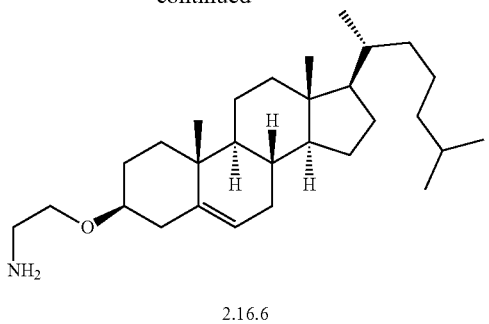

2.16.6

Reagents and conditions: (a) Tossyl chloride, Pyridine, Dry CH₂Cl₂, 0° C. to r.t, 6 h (b) 1,4-Dioxane 110° C., 12 h, 55% over two steps. (c) Tossyl chloride, Pyridine, Dry CH₂Cl₂, 0° C. to r.t, 12 h, 54%, (d) NaN₃, DMF, r.t, 12 h, 94%, (e) TPP, THF:H₂O (3:1), r.t, 4 h, 94%

Step C:

To an ice cooled solution of cholesteryl ethylene glycol 2.16.3 (6.95 g, 16.13 mmol) in 15 ml dichloro methane, 13 ml pyridine is added under nitrogen atmosphere and stirred for about 15 minutes. To this solution, p-toluene sulphonyl chloride (3.7 g, 19.35 mmol) is added and stirred for about 5 h at about 0° C. and TLC is checked. After completion, the reaction mixture is diluted with CHCl₃ (20 mL) and washed with 1N HCl (3×50 mL) and brine (20 mL) successively. The organic layer is dried over anhydrous Na₂SO₄ and concentrated under vacuum and purified by silica gel chromatography to obtain intermediate 2.16.4.

Step D:

In a 50 mL round bottomed flask, compound 2.16.4 (6 g, 10.26 mmol) is taken in 20 ml of DMF under nitrogen atmosphere and is stirred for about 30 minutes to get a clear solution (warm if necessary). To this solution, sodium azide (3.4 g, 51.33 mmol) is added and stirred for about 18 h at room temperature and TLC is checked. After completion, the reaction mixture is concentrated under vacuum to remove THF and is purified by flash chromatography to obtain intermediate 2.16.5.

Step E:

To a solution of azide 2.16.5 (3 g, 7.6 mmol) in 15 ml dry DMF, TPP (1.5 g, 15.2 mmol) is added under nitrogen atmosphere. The reaction is stirred for about 6 h at room temperature and about 2 mL of water is added to the reaction mixture. The reaction mixture is stirred for an additional time-period of 6 h and TLC is checked. After completion, the reaction mixture is concentrated under reduced pressure and is purified by silica gel chromatography utilizing methanol/chloroform as eluent to achieve amine intermediate 2.16.6.

Scheme 5

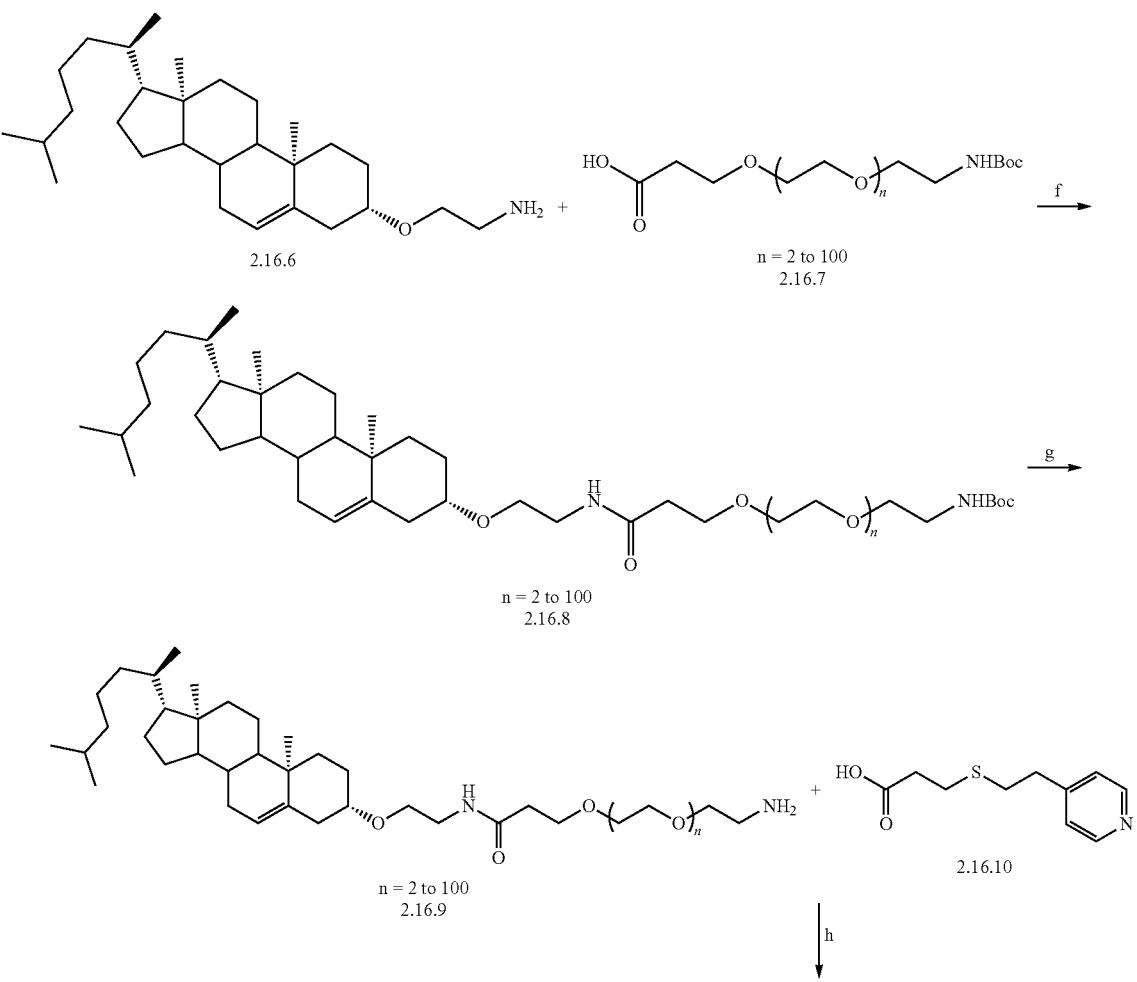

-continued

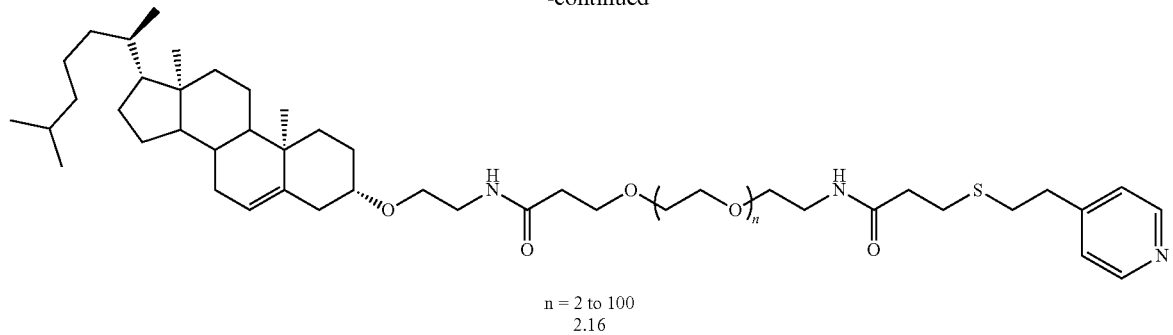

n = 2 to 100
2.16

Reagents and conditions: (f) EDCl, HOBT, CH2Cl2, 0° C. to r.t, 12 h; (g) TFA, CH2Cl2, 0° C. to r.t, 3 h;
(h) EDCl, HOBT, CH2Cl2, 0° C. to r.t, 12 h.

Step F:

In a 50 mL single neck round bottom flask, BocHN-PEG-COOH 2.16.7 is taken in 10 ml $CH_2Cl_2$ under nitrogen atmosphere. Solid EDCl and HOBT are added successively to the reaction mixture. DIPEA is added to make the solution alkaline and the reaction mixture is stirred for another 20 minutes. To this activated acid solution, amine 2.16.6 is added and the mixture is stirred at room temperature for about 12 h and TLC is checked. After completion, the reaction mixture is quenched with water, extracted with chloroform, dried over anhydrous $Na_2SO_4$ and thereafter concentrated. The residue is purified by silica gel chromatography utilizing methanol-chloroform as eluent to obtain intermediate 2.16.8.

Step G:

In a 50 mL single neck round bottom flask, Boc protected amine 2.16.8 is taken in $CH_2Cl_2$ and the flask is cooled to about 0° C. To this solution, TFA is added and the mixture is stirred for about 3 hours at the same temperature. After completion, the reaction mixture is concentrated under rotary evaporator and the crude product 2.16.9 is utilized for the next reaction without further purification.

Step H:

In a 50 mL single neck round bottom flask intermediate 2.16.10 is taken in $CH_2Cl_2$ under nitrogen atmosphere. Solid EDCl and HOBT are added successively to the reaction mixture. DIPEA is added to make the solution alkaline and the reaction mixture is stirred for another 20 minutes. To this activated acid solution, amine 2.16.9 is added and the mixture is stirred at room temperature for about 12 h and TLC is checked. After completion, the reaction mixture is quenched with water, extracted with chloroform, dried over anhydrous $Na_2SO_4$ and thereafter concentrated. The residue is purified by silica gel chromatography utilizing methanol-chloroform as eluent to obtain final product 2.16.

Example 5: Synthesis of 2.18

Figure 26:
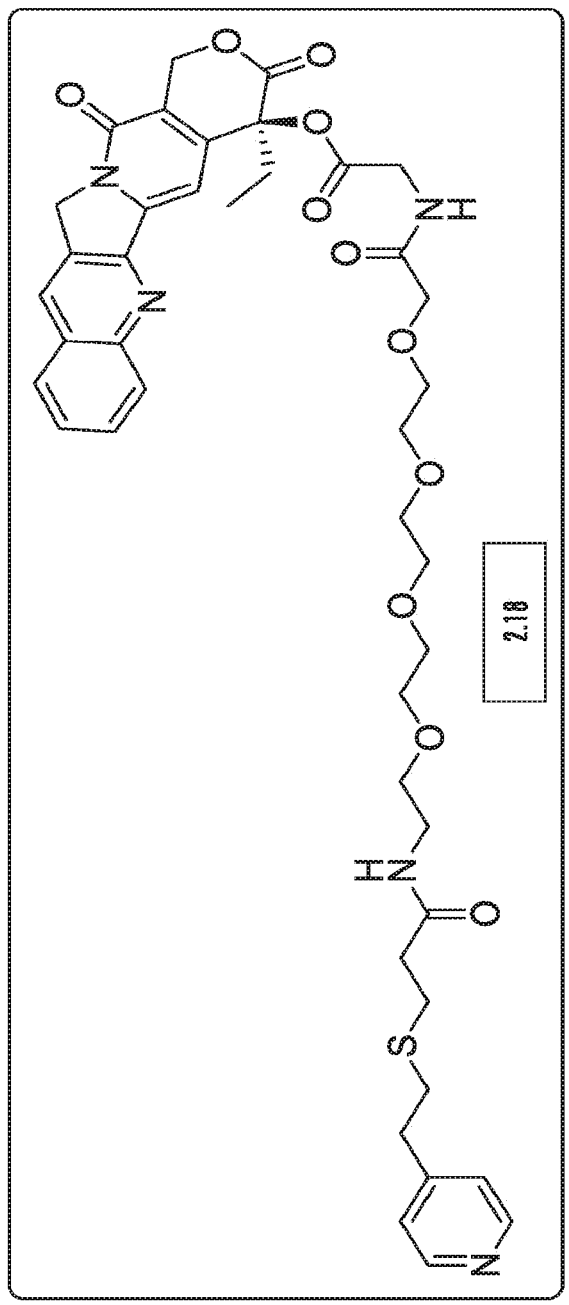
FIG. 26 shows the structure of compound 2.18 where 4-MEP is linked to camptothecin via a cleavable linker.

Conjugate 2.18, shown in FIG. 26, can be synthesized as outlined in Scheme 6.

Step A:

In a 100 ml round bottom flask, Boc-Glycine (1.5 g, 8.61 mmol) was taken in dry dichloromethane (30 ml) under nitrogen atmosphere. To this solution, DIPC (1.20 mL, 8.616 mmol) followed by DMAP (210 mg, 8.616 mmol) was added and stirred for 45 minutes at 0° C. To this activated acid solution, Camptothecin (1 g, 2.872 mmol) was added and allowed to stir overnight at room temperature and TLC was checked. After completion, the reaction mixture was quenched with water (50 mL) and extracted with chloroform (3×10 mL). The combined organic layer was concentrated on rotary evaporator. 1 ml of DCM was added and the residue was precipitated using diethyl ether to obtain intermediate 2.18.1 (1.2 g) as yellow solid. $^1H$ NMR of 2.18.1 (400 MHz, DMSO-D6) δ: 8.70 (s, 1H), 8.14 (dd, J=8.1, 5.1 Hz, 2H), 7.88 (t, J=7.6 Hz, 1H), 7.72 (t, J=7.6 Hz, 1H), 7.44 (t, J=6.0 Hz, 1H), 7.25 (s, 1H), 5.50 (s, 2H), 5.37-5.23 (m, 2H), 3.94 (dd, J=17.9, 6.1 Hz, 1H), 3.82 (dd, J=17.9, 5.9 Hz, 1H), 2.12 (dt, J=18.6, 6.6 Hz, 2H), 1.39 (s, 9H), 0.92 (t, J=7.3 Hz, 3H). $^{13}C$ NMR of 2.18.1 (125 MHz, DMSO) δ: 169.80, 167.33, 157.03, 156.70, 156.12, 152.46, 148.04, 146.05, 145.49, 131.62, 130.54, 129.77, 129.02, 128.64, 128.04, 127.81, 118.99, 95.78, 78.72, 76.42, 66.43, 50.31, 42.33, 40.89, 28.38, 7.77. ESIMS m/z=506.2 [M+H]$^+$ for $[C_{27}H_{27}N_3O_7]^+$.

Scheme 6

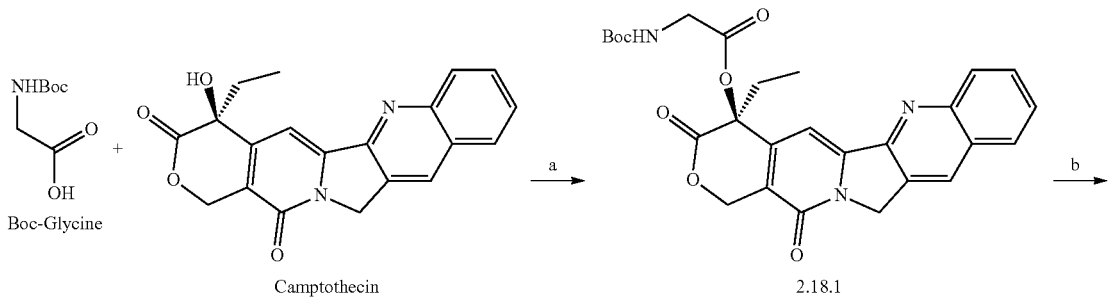

-continued
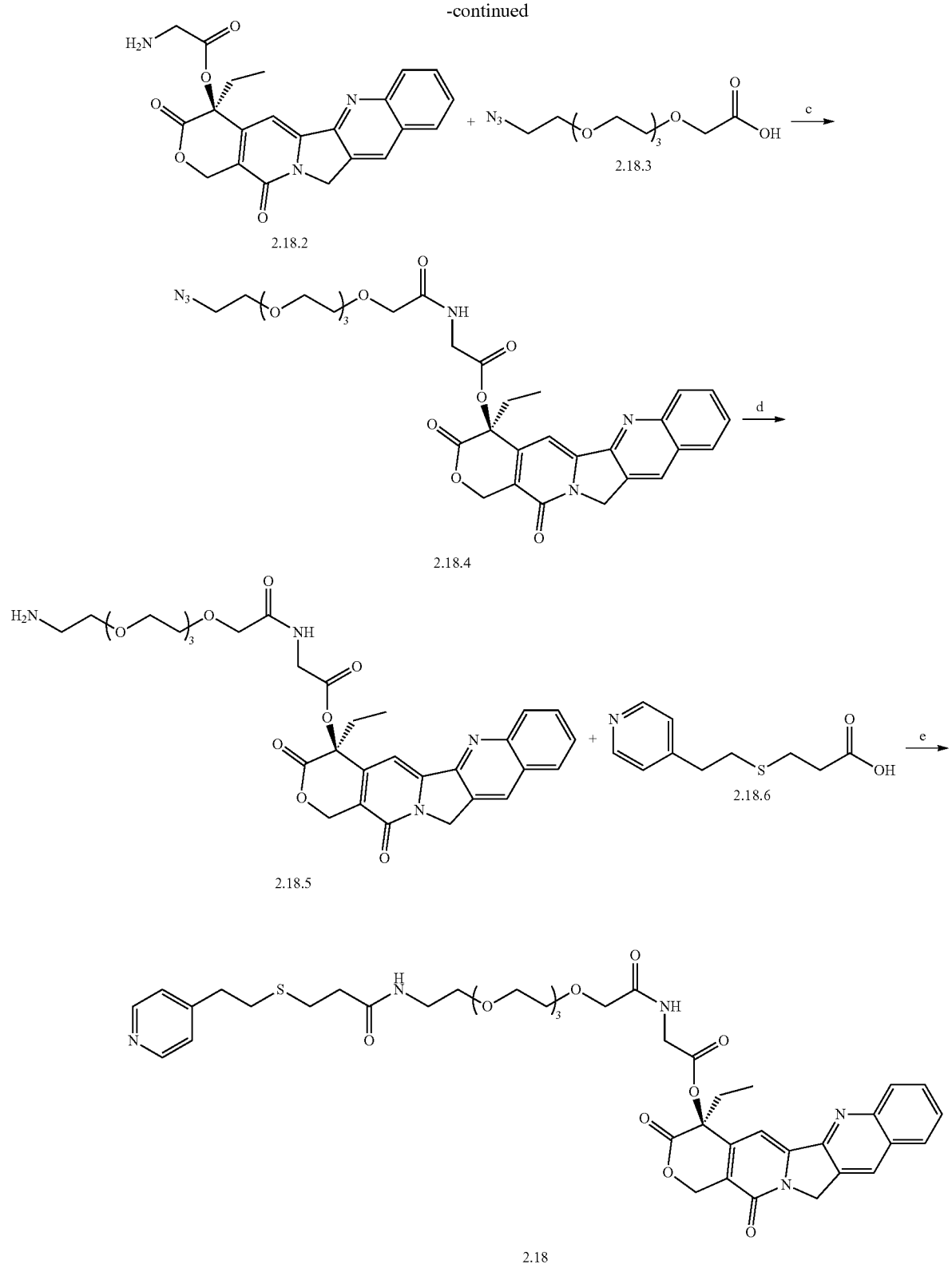
Reagents and conditions: (a) DIPC, DMAP, CH2Cl2, 12 h (b) TFA, CH2Cl2, 0° C. to r.t, 1 h. (c) EDCl, HOBT, DIPEA, CH2Cl2, 12 h (d) H2, Pd/C, Methanol, cat. TFA, r.t, 45 min. (e) EDCl, HOBT, DIPEA, CH2Cl2, 3 h Step B:

In a 100 ml round bottom flask, intermediate 2.18.1 (3 g, 5.93 mmol) was taken in dichloromethane (20 mL) under nitrogen and cooled to 0° C. To this solution TFA (10 mL) was added drop wise and stirred for 1 h at room temperature. After completion the reaction mixture was concentrated on rotary evaporator using NaOH trap. The residue was diluted with 1 ml DCM and excess of diethyl ether (2×20 mL). Precipitate of intermediate 2.18.2 (2.02 g crude) was centrifuged and utilized for the next reaction.

Step C:

In a 100 mL single neck round bottom flask, intermediate 2.18.3 (2.77 g, 10 mmol) was taken in dry dichloromethane (40 mL) under nitrogen atmosphere and cooled to 0° C. To this ice-cooled solution EDCI (2.68 g, 14 mmol), HOBt (1.89 g, 14 mmol) and DIPEA (10 mL) were added successively. The reaction mixture was stirred for 30 minutes and amine intermediate 2.18.2 (2.02 g, crude) was added. The reaction mixture was stirred for another 12 h and TLC was checked. After completion the reaction mixture was quenched with water (2×50 mL) and extracted with dichloromethane (2×30 mL). The combined organic layer was concentrated under vacuum and precipitated with dichloromethane:diethyl ether (1:10) to remove remaining HOBT. The crude intermediate 2.18.4 (2.5 g) was used for next reaction without further purification. IR of 2.18.4 (KBr) ν: 3374.3, 2100.8, 1751.0, 1661.5, 1602.7, 1123.9 cm$^{-1}$. ESIMS m/z=687.1 [M+Na]$^+$ for $[C_{32}H_{36}N_6O_{10}]^+$.

Step D:

In a 100 mL single neck round bottom flask, intermediate 2.18.4 (4 g, 6.02 mmol) was taken in methanol (30 mL) and ethyl acetate (10 mL) was added till the solution became clear. Palladium-Carbon (100 mg) and TFA (0.5 mL) were added and allowed to stir for 45 minutes under hydrogen atmosphere. After completion the reaction was filtered through a thin pad of celite, washed with methanol (10 mL) and concentrated. The residue was precipitated with dichloromethane:diethyl ether (1:10) to obtain intermediate 2.18.5 (3 g).

Figure 33:
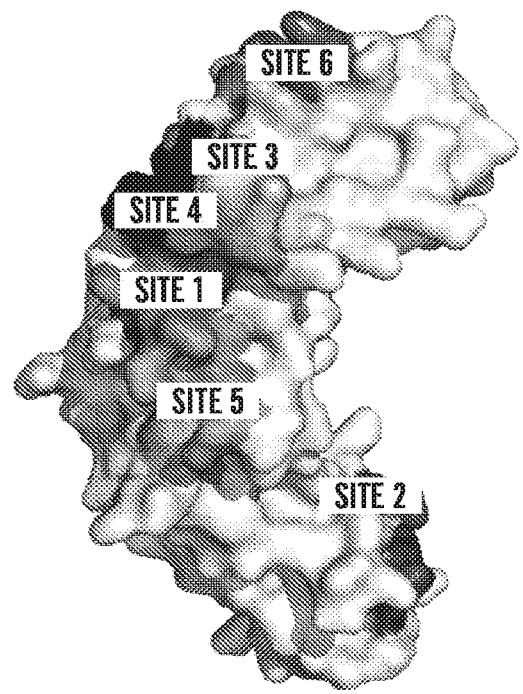
FIG. 33 shows the six binding sites of 4-MEP on Fc fragment of IgG as reported by Lin et al.

Step E:

In a 100 mL single neck round bottom flask, intermediate 2.18.6 (385 mg, 1.818 mmol) was taken in dry dichloromethane (15 mL) under nitrogen atmosphere and cooled to 0° C. To this ice-cooled solution, EDCI (250 mg, 1.3636 mmol), HOBt (190 mg, 1.3636 mmol) and DIPEA (0.3 mL) were added successively. The reaction mixture was stirred for 30 minutes and amine intermediate 2.18.5 (580 mg, 0.909 mmol) was added. The reaction mixture was stirred for another 3 h and TLC was checked. After completion the reaction mixture was quenched with water (2×20 mL), washed with citric acid solution (5%, 10 mL) and extracted with dichloromethane (2×20 mL). The combined organic layer was concentrated under vacuum and precipitated with diethyl ether (20 mL). The residue was purified by silica gel chromatography to obtain 2.18 (600 mg, 79%) as yellow solid. The crude compound (~70% pure) was further purified by RP-HPLC using a C18 column (250×20, 5 μm) and a water/acetonitrile gradient to yield final compound 2.18 with 88% purity. $^1$H NMR of 2.18 (500 MHz, CDCl$_3$) δ: 8.47 (d, J=5.9 Hz, 2H), 8.37 (s, 1H), 8.24 (d, J=8.6 Hz, 1H), 7.92 (d, J=8.0 Hz, 1H), 7.82 (ddd, J=8.4, 6.9, 1.3 Hz, 1H), 7.77 (t, J=5.7 Hz, 1H), 7.67-7.63 (m, 1H), 7.34 (s, 1H), 7.11 (d, J=5.9 Hz, 2H), 6.68 (s, 1H), 5.67 (d, J=17.1 Hz, 1H), 5.38 (d, J=17.1 Hz, 1H), 5.26 (d, J=2.4 Hz, 2H), 4.51 (dd, J=18.3, 6.8 Hz, 1H), 4.16 (dd, J=18.3, 4.9 Hz, 1H), 4.00 (dd, J=35.1, 16.1 Hz, 2H), 3.67-3.36 (m, 16H), 2.87-2.73 (m, 6H), 2.44 (t, J=7.4 Hz, 2H), 2.31-2.10 (m, 2H), 0.98 (t, J=7.5 Hz, 3H). $^{13}$C NMR of 2.18 (125 MHz, CDCl$_3$) δ: 171.14, 170.82, 169.00, 167.30, 157.27, 152.16, 149.73, 149.24, 148.77, 146.43, 145.50, 131.18, 130.69, 129.68, 128.41, 128.15, 128.09, 123.89, 119.87, 96.23, 76.78, 71.01, 70.37, 70.35, 70.30, 70.27, 70.09, 70.00, 69.82, 67.10, 49.97, 40.48, 39.24, 36.58, 35.25, 32.47, 31.75, 27.75, 7.53. IR of 2.18 (KBr) ν: 3423.3, 2918.7, 1751.0, 1637.9, 1398.6, 1088.1, 1040.5 cm$^{-1}$. ESIMS m/z=832.3 [M]$^+$ for $[C_{42}H_{49}N_5O_{11}S]^+$ Example 6: Binding Site of 2.18 on Anti-EGFR Antibody Interaction of 4-MEP ligand with the Fc fragment of IgG antibody has been studied by Lin et al using docking and molecular simulations techniques. They have reported six possible binding sites for 4-MEP substrates (Table 1, FIG. 33). Among the six sites, Lin et al. have observed higher binding affinity of 4-MEP with site 1.

TABLE 1

| MEP binding site residues on Fc fragment | |
|---|---|
| Sites | Active site Residues |
| Site 1 | VAL279, VAL284, ALA287, LEU306, VAL308, LEU309, ASN312, LYS317, TRY319 |
| Site 2 | GLN32, GLU388, ASN389, ASN390, LEU410, VAL412, ASP413, ARG416 |
| Site 3 | LYS274, PHE275, ASN276, GLN283, HIS285, ASN286, THR289, PRO291 |
| Site 4 | TRY278, GLY281, VAL282, GLN283, GLU318, LYS320 |
| Site 5 | THR250, LEU251, ILE253, HIS310, GLN311, HIS435 |
| Site 6 | SER324, ASN325, LYS326, ALA327, LEU328, PRO329, PRO331 |

Molecular interactions and affinity relationship of ligand 2.18 with the six possible 4-MEP binding sites on Fc fragment of antibody were investigated. Following computational techniques were used:
  (i) BLAST: used for the sequence search analysis of protein for the selection of template;
  (ii) QM for optimization of ligand: to obtain lowest energy conformation of ligand and to calculate force field parameters to perform molecular dynamics simulations;
  (iii) Docking: to obtain starting conformations of protein ligand complexes;
  (iv) Molecular dynamic simulations: to study protein and ligand interactions; and
  (v) Umbrella sampling simulations: to compute free energy of binding of ligand 2.18 at different binding sites The crystal structure of Fc fragment of anti-EGFR antibody was not available. Thus, BLAST sequence search (Altschul, S. F., Madden, T. L., Schaffer, A. A., Zhang, J., Zhang, Z., Miller, W. and Lipman, D. J. (1997) "Gapped BLAST and PSI-BLAST: a new generation of protein database search programs." Nucleic Acids Res. 25:3389-3402) was performed using the anti-EGFR antibody Fc sequence. From the resultant PSI-BLAST search, the 1FC1 fragment was found to be more than 95% identical to the anti-EGFR Fc sequence. The molecular structure of the Fc fragment of IgG with PDB ID 1FC1 (Deisenhofer, J. Biochemistry 1981, 20, 2361-2370) was obtained from the Protein Data Bank (PDB). 1FC1 consists of two chains of A and B with CH2-CH3 constant domains of IgG1, which are identical in the amino acid sequence and are similar in the 3D structure.

Therefore, only chain A of 1FC1 (defined as 1FC1-A) was considered here for further study.

Ligand Structure Optimization

Figure 34:
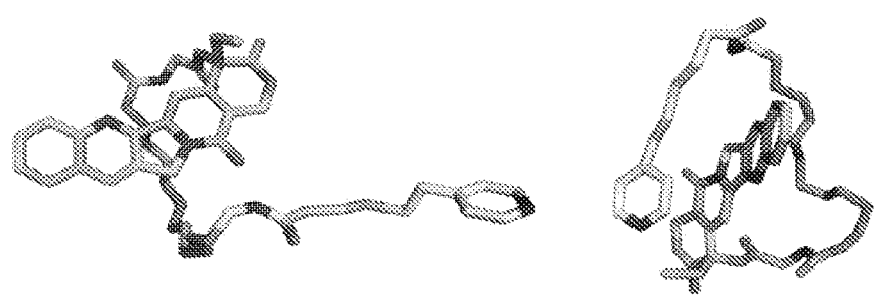
FIG. 34 shows the structure of ligand 2.18 after QM optimization and after short MD in vacuum.

Quantum chemical geometry optimization of ligand 2.18 was performed to obtain its lowest energy conformation. Force field development was performed for ligand 2.18 for classical MD simulations. The bonded and LJ-parameters were adapted from CHARMM force field. Parameters for one dihedral angle and partial charges on each atom in ligand 2.18 were computed using quantum chemical calculations. Further, a short MD simulation in vacuum was performed starting with the geometry optimized structure. Structure obtained after quantum chemical geometry optimization and short MD simulation are provided in FIG. 34 validating the force field parameters.

Docking

Autodock Tools 1.5.6 (Michel F. Sanner. Python: A Programming Language for Software Integration and Development. J. Mol. Graphics Mod., 1999, Vol 17, February. pp 57-61) was used to extract the crystalline water and chain B from 1FC1 crystal structure. The polar hydrogens were assigned, Gasteiger charges were added and the rigid protein structure was saved in the PDBQT format. Similarly ligand 2.18 obtained from the quantum chemical optimization was taken and nonpolar hydrogens were merged. Gasteiger charges were added to the ligand and flexibility was introduced by allowing 25 torsional angles. Finally, the structure was saved in the PDBQT format to perform docking with 1FC1-A.

Autodock Vina 1.1.2 (Trott O., Olson A. J. (2009) AutoDock Vina: Improving the speed and accuracy of docking with a new scoring function, efficient optimization, and multithreading. J Comput Chem; 31:455-461) was used for docking. Docking grid size of 16 Å×22 Å×26 Å was used for the search space. The same grid dimensions were taken for all the other reported binding sites (Table 1). The grid size was selected in order to allow the whole ligand molecule to scan possible conformations. For each binding site the center of co-ordinates were obtained from the center of mass of active site residues. The docking results were assessed based on their energy criteria, conformation with the best estimated free energy of binding. For each docking calculation, 10 poses were ranked according to the Autodock Vina scoring function.

Figure 35:
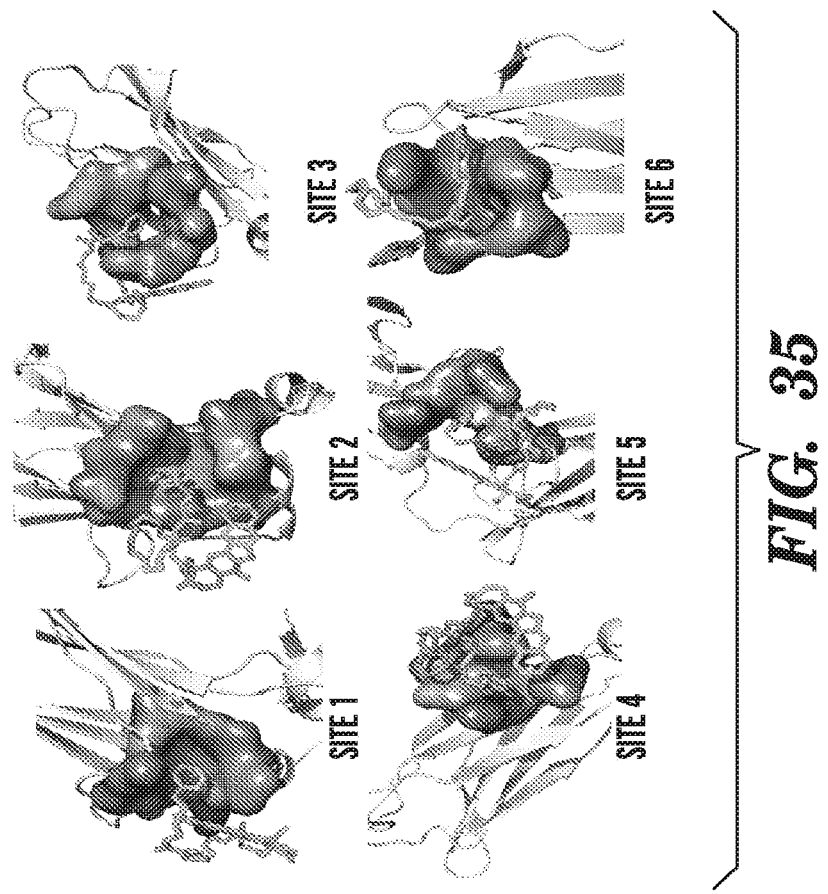
FIG. 35 shows the docked conformations of ligand 2.18 in the six binding sites on 1FC1-A.

The top scoring conformations of ligand 2.18 at different sites were found to contain 4-MEP part inside the cavity (FIG. 35). It also indicates that the camptothecin part has low affinity for the six 4-MEP binding sites reported by Lin et al. The docked ligand-1FC1-A complex for the six binding sites was further used to perform MD simulations.

MD Simulation

Separate simulations were performed for each of the six sites shown in Table 1. All the simulations were performed using Gromacs 4.6.7 (Hess, et al. (2008) J. Chem. Theory Comput. 4: 435-447). For each simulation setup, the protein-ligand complex was first placed in a cubic simulation box maintaining a 2 nm distance with the box walls. Then the complex was solvated with TIP3P model water molecules. 4 chloride counter ions were added to maintain electroneutrality in all the simulations. All the bonded and non-bonded interaction potential parameters for protein were adapted from CHARMM 36 force field. Force field details for the ligand have been explained above. Solvated systems were energy minimized using steepest-descent algorithm.

Following energy minimization, NPT simulation was performed for 1000 ps keeping the protein-ligand complex position restrained with force constant of 1000 kJ/mol as implemented in Gromacs 4.6.7. After this, NPT simulation was carried out by removing the position restrain on ligand but maintaining the position restrain on protein with 1000 kJ/mol force constant as implemented in Gromacs 4.6.7. Following this, position restrain on protein was removed slowly by decreasing the force constant in steps with 800, 500, 250, 100, 50 and 1 kJ/mol. At each step, 100 ps of NPT run were performed. These position restrained simulations allow the water molecules near the protein surface to equilibrate resulting in better solvation of the protein-ligand complex. This equilibration protocol is followed for the simulations at all the six binding sites of 1FC1-A.

Finally, production NPT simulations were performed without any position restrain for ligand 2.18-1FC1-A complexes separately for the six binding sites for 5 ns. P-LINCS algorithm was used to constrain all the covalent bonds and time step of 2 fs was used for all the simulations. Electrostatic interactions were taken care of by PME method with cutoff of 1.2 nm, and van der Waals interactions were switched off between 1.0 to 1.2 nm. Pressure was kept constant at 1 bar using Parrinello-Rahman barostat and temperature was fixed at 300 K using Nose-Hoover thermostat.

Figure 36:
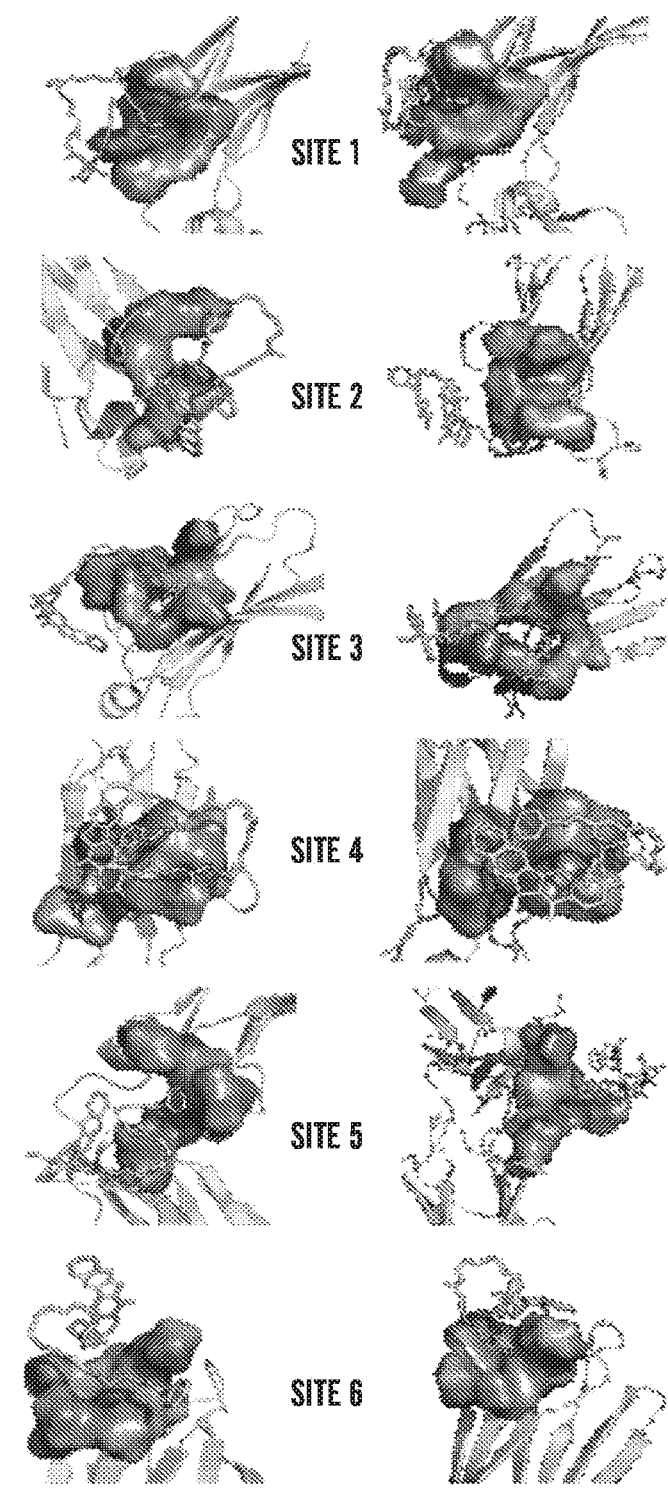
FIG. 36 shows snapshots before (left) and after (right) 5 ns of production MD simulation for six binding sites. The 4-MEP part of ligand 2.18 is inside the binding cavity for sites 1, 3, 4, and 6.

Snapshots before and after 5 ns production run are depicted in FIG. 36. It is evident that the ligand comes out of the binding sites 2 and 5 during the 5 ns production run. It indicates that the binding affinity of these sites for ligand 2.18 is low. Ligand remains in the binding sites 1, 3, 4, and 6 during the 5 ns production run implying higher affinity of these sites for ligand 2.18.

Figure 37:
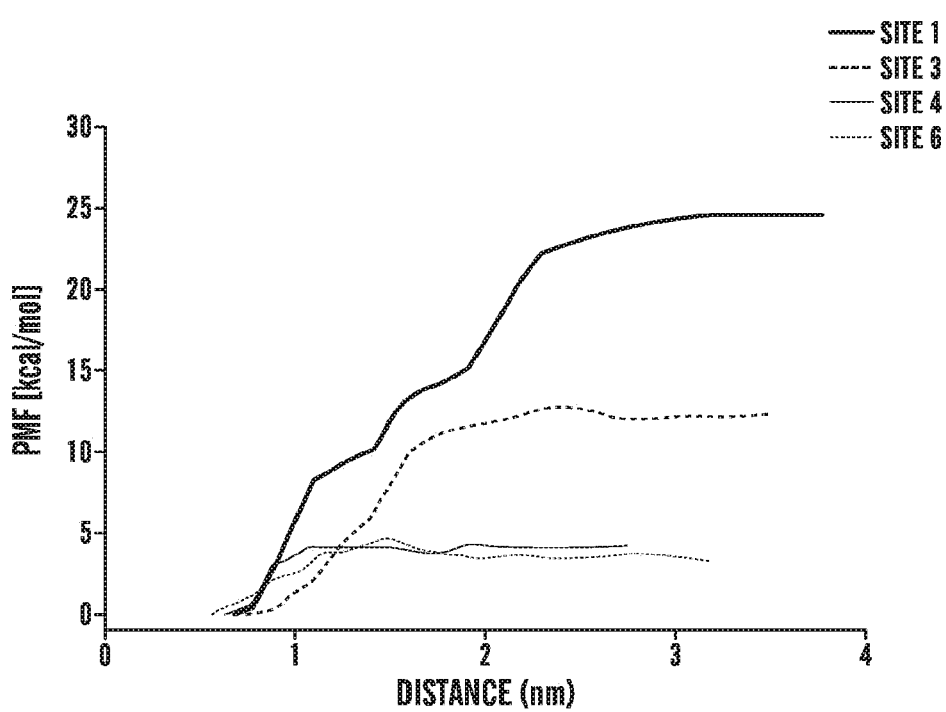
FIG. 37 shows PMF as a function of distance between ligand 2.18 and sites 1, 3, 4, and 6.
Figure 38A:
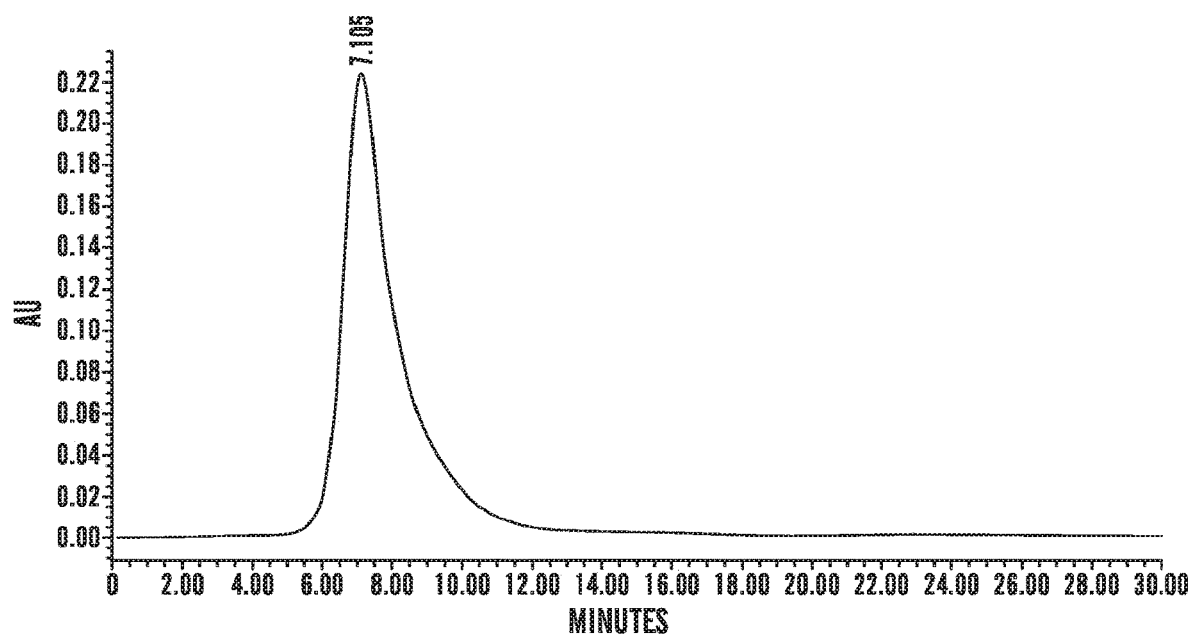
FIGS. 38A-D show the SE-HPLC profiles.
Figure 38B:
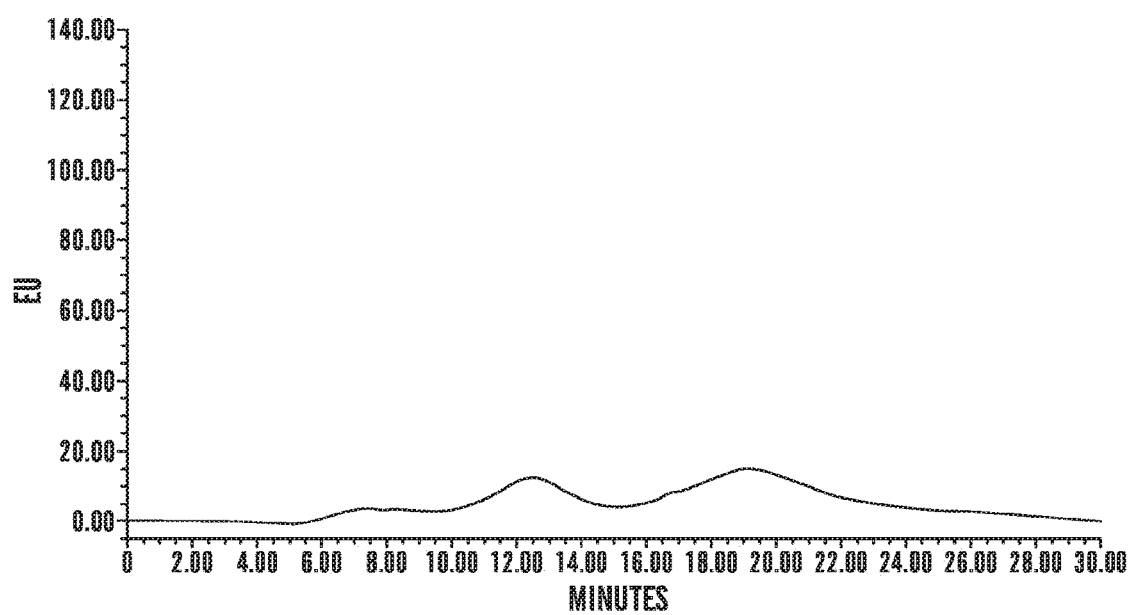
Figure 38C:
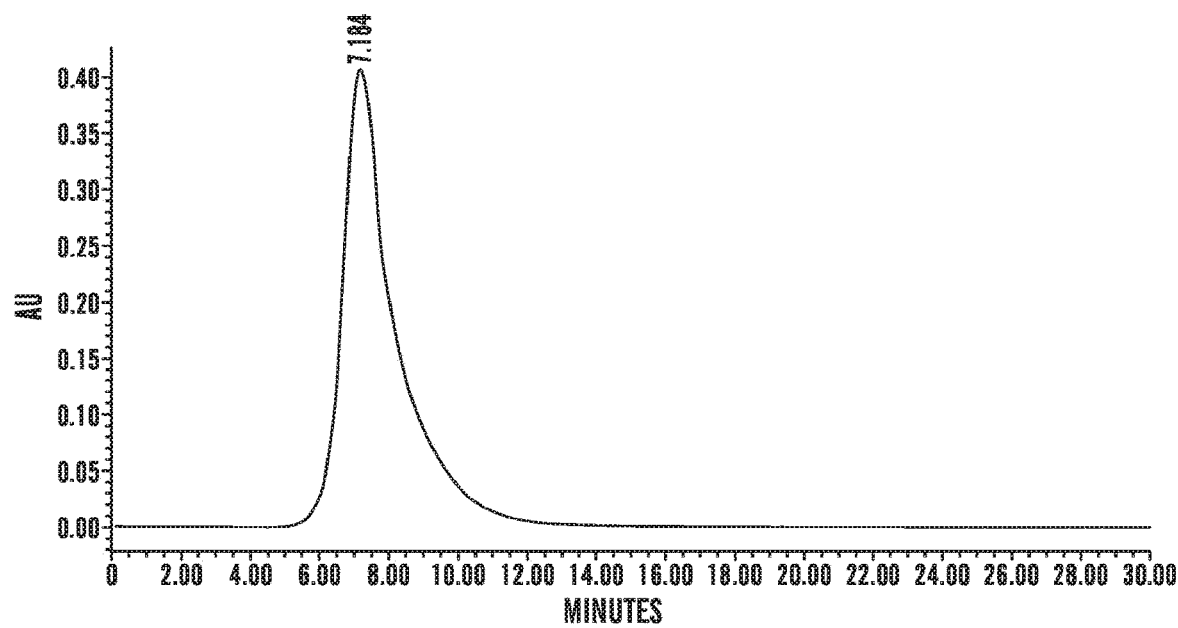
Figure 38D:
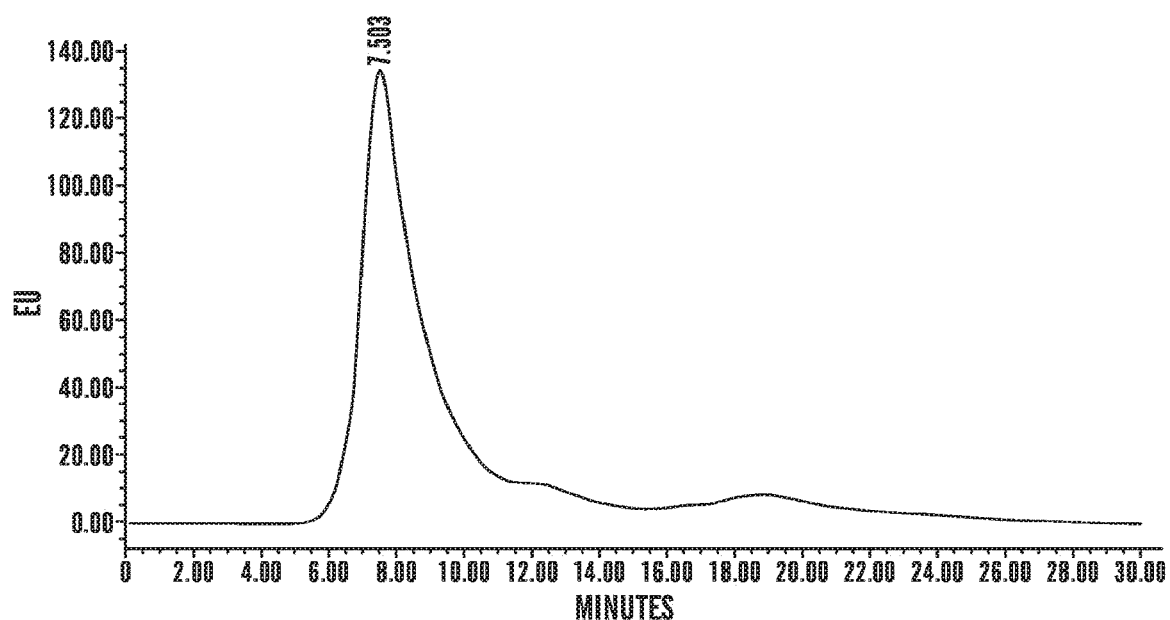

To further quantify and compare the affinity of sites 1, 3, 4, and 6 for ligand 2.18 we have performed free energy calculations using umbrella sampling method (Justin A. Lemkul and David R. Bevan, Assessing the Stability of Alzheimer's Amyloid Protofibrils Using Molecular Dynamics. J. Phys. Chem. B 2010, 114, 1652-1660) as implemented in Gromacs 4.6.7. For this, output configuration from 5 ns production run was chosen for all the four mentioned sites, and the ligand was pulled with a velocity of 10 nm $ns^{-1}$ by applying harmonic potential to its centre of mass (COM) with force constant of 1000 kJ/mol/$nm^2$. Different frames were extracted from pulling simulation at certain intervals (based on overlap of histograms) of COM distance between pulled chain and reference group. 500 ps of umbrella sampling production run was performed on each configuration by applying the same harmonic potential used during pulling and taking initial COM distance as reference. Then weighted histogram analysis method (WHAM) (Jochen S. Hub, Bert L. de Groot, and David van der Spoel, g_whams—A Free Weighted Histogram Analysis Implementation Including Robust Error and Autocorrelation Estimates. J. Chem. Theory Comput. 2010, 6, 3713-3720) was used to calculate potential of mean force (PMF) by analysing simulation trajectories of each umbrella windows. PMF as a function of distance is depicted in FIG. 37.

TABLE 2

Binding free energies of ligand 2.18 with sites 1, 3, 4, and 6.

| Sites | Binding free energy values (kcal/mol) |
|---|---|
| Site 1 | −24.63 |
| Site 3 | −12.14 |
| Site 4 | −3.96 |
| Site 6 | −3.33 |

Free energy of binding ligand 2.18 at sites 1, 3, 4, and 6 calculated from PMF (FIG. 37) are summarized in Table 2. Free energy of binding indicates how efficiently a ligand binds to a cavity. Binding free energy is highest for site 1 which shows that the ligand binds best with site 1 compared to the other sites. From Table 2 and FIG. 37 the order of binding free energy at different sites is as follows:

Site 1>Site 3>Site 4>Site 6

Example 7: Conjugation of 2.18 with Anti-EGFR Antibody 60 nmoles of anti-EGFR antibody was concentrated to a final volume of 1 mL and buffer exchanged into 20 mM sodium phosphate, 150 mM sodium chloride, pH 7.0 buffer. 10-fold excess (600 nmoles) of 2.18 was weighed and antibody was added to the compound. The reaction was incubated at 37° C. for 15 hrs with shaking. The mixture was then centrifuged and the supernatant was filtered through 0.2 µm filter to remove any particles/precipitate. The resulting solution was buffer-exchanged using Zeba spin desalting columns (7K MWCO, 5 ml) to remove any free linker-drug remaining.

The ADC solution was then analysed by SE-HPLC (FIG. 38). Reprosil SEC 200 (300×4.6, 5 µm) column was used with 20 mM sodium phosphate, 150 mM sodium chloride, pH 7.0 buffer as mobile phase. The column eluent was connected to photo-diode array detector (200-700 nm) and fluorescence detector ($\lambda_{ex}$=369 nm; $\lambda_{em}$=430 nm). Drug-to-antibody ratio was calculated based on fluorescence peak area. The concentration of the antibody was measured by UV absorbance at 280 nm using an extinction coefficient of 1.49 AU·ml·mg$^{-1}$·cm$^{-1}$.

Example 8: Cytotoxicity of ADC with 2.18

The cytotoxic potency of 2.18 conjugated to an anti-EGFR antibody was assessed using MTT cell proliferation assay. This is a high-throughput method that can be used to quantify cellular viability using colorimetric detection.

For the MTT assay, the metastatic breast cancer cell lines MDA-MB-231 (EGFR+) and MDA-MB-468 (EGFR+++) were cultured in DMEM media containing 10% Fetal Bovine Serum, 50 IU/mL Penicillin and 50 µg/mL Streptomycin.

Figure 39:
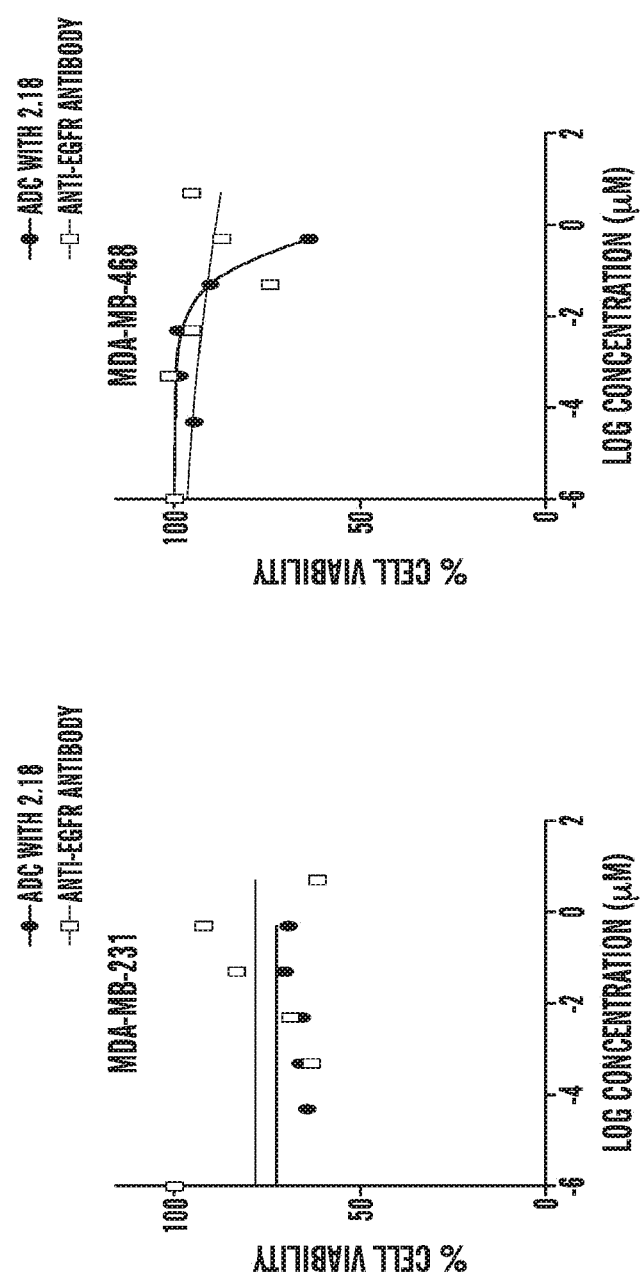
FIG. 39 shows the in vitro cytotoxicity profile of ADC with 2.18 conjugated to anti-EGFR antibody.

For testing the conjugate, cells were plated in 96-well plates (4000 cells/well). Serial dilutions of the ADC and antibody were made (15 µM-0.000015 µM) and the cells were treated with 100 µL/well of the above solutions. The survival profiles of the cells were measured by the MTT assay after 48 and 72 hours of drug treatment for MDA-MB-231 and MDA-MB-468 respectively. (FIG. 39). The survival profiles clearly demonstrate the potency of the anti-EGFR conjugate with 2.18 (IC50=1 µM) as compared to anti-EGFR antibody alone in EFGR+++ cells (MDA-MB-468). The antibody-drug conjugate (ADC) was also specific as both the ADC and the antibody alone were ineffective in killing EGFR+ cells (MDA-MB-231).

Example 9: Synthesis of 2.19

Figure 27:
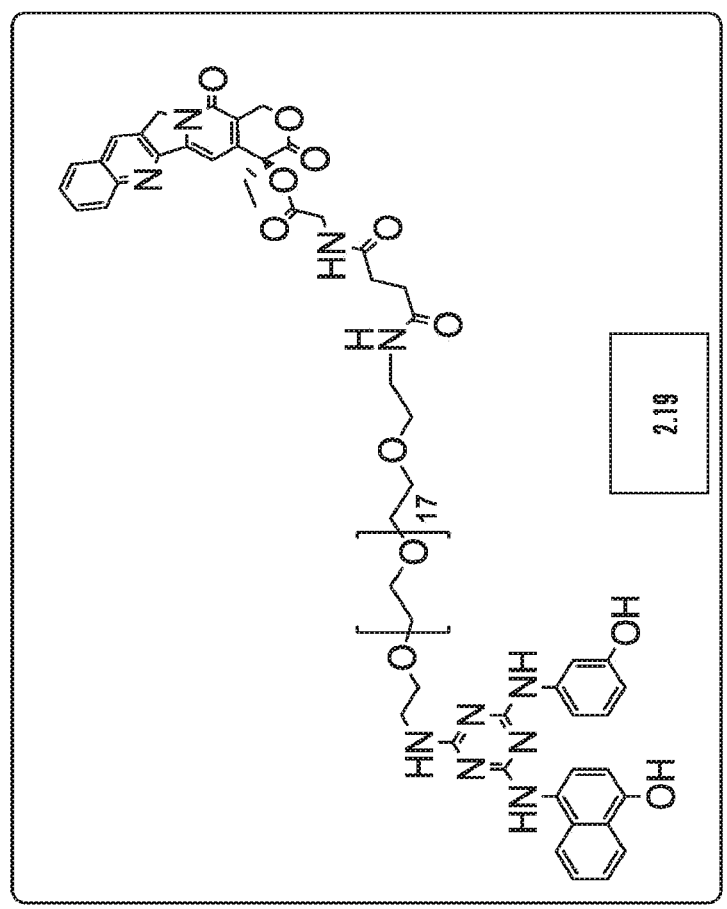
FIG. 27 shows the structure of compound 2.19 where triazine moeity is linked to camptothecin via a cleavable linker.

Conjugate 2.19, shown in FIG. 27, can be synthesized as outlined in Scheme 7.

Step A:

A solution of 3-aminophenol (1.1 g, 10 mmol) in acetone (15 mL) is added dropwise to a suspension of cyanuric chloride (1.8 g, 10 mmol) in acetone:deionised water (40 mL, 3:5) while stirring at 0° C. NaHCO$_3$ (0.8 g, 10 mmol) in distilled water (10 mL) is added to maintain the pH between 6-7 during the reaction. A white crystalline solid precipitate is obtained which is filtered off and washed with cold distilled water. The resulting white powder of 2.19.1 is dried under vacuum.

Step B:

4-amino-1-naphthol hydrochloride (1.8 g) is taken in acetone:water (30 mL, 1:1) and the solution of NaHCO$_3$ (80 mg, 1.0 mmol) in water (15 mL) is added to bring the pH between 6-7. This mixture is added to a solution of intermediate 2.19.1 (2.2 g, 8.0 mmol) in acetone (25 mL) and heated to 45° C. A solution of NaHCO$_3$ (1.0 mmol; 80 mg) in distilled water (10 mL) is added to maintain the pH between 6-7 during the course of reaction. After 5 h, the mixture is concentrated in vacuum and the resulting residue is partitioned between ethyl acetate (80 mL) and distilled water (20 mL). The organic phase is recovered and concentrated in vacuum to obtain intermediate 2.19.2.

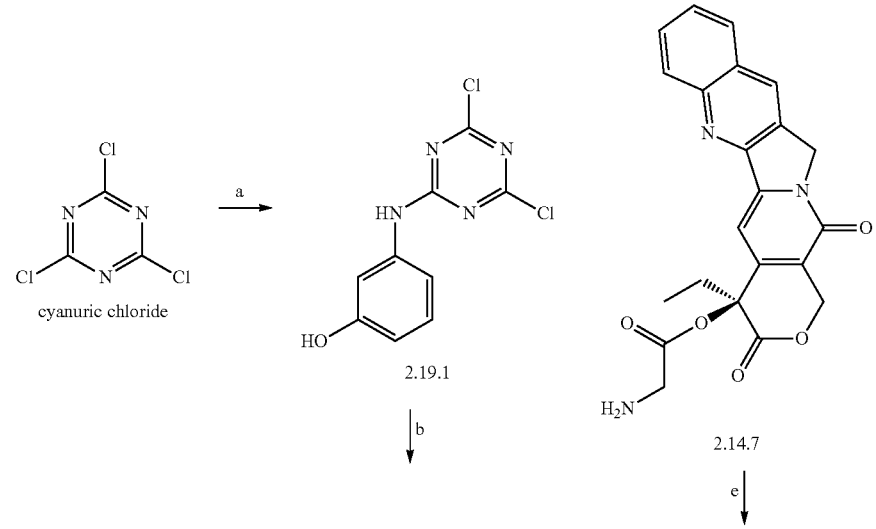

Scheme 7

75
76
-continued
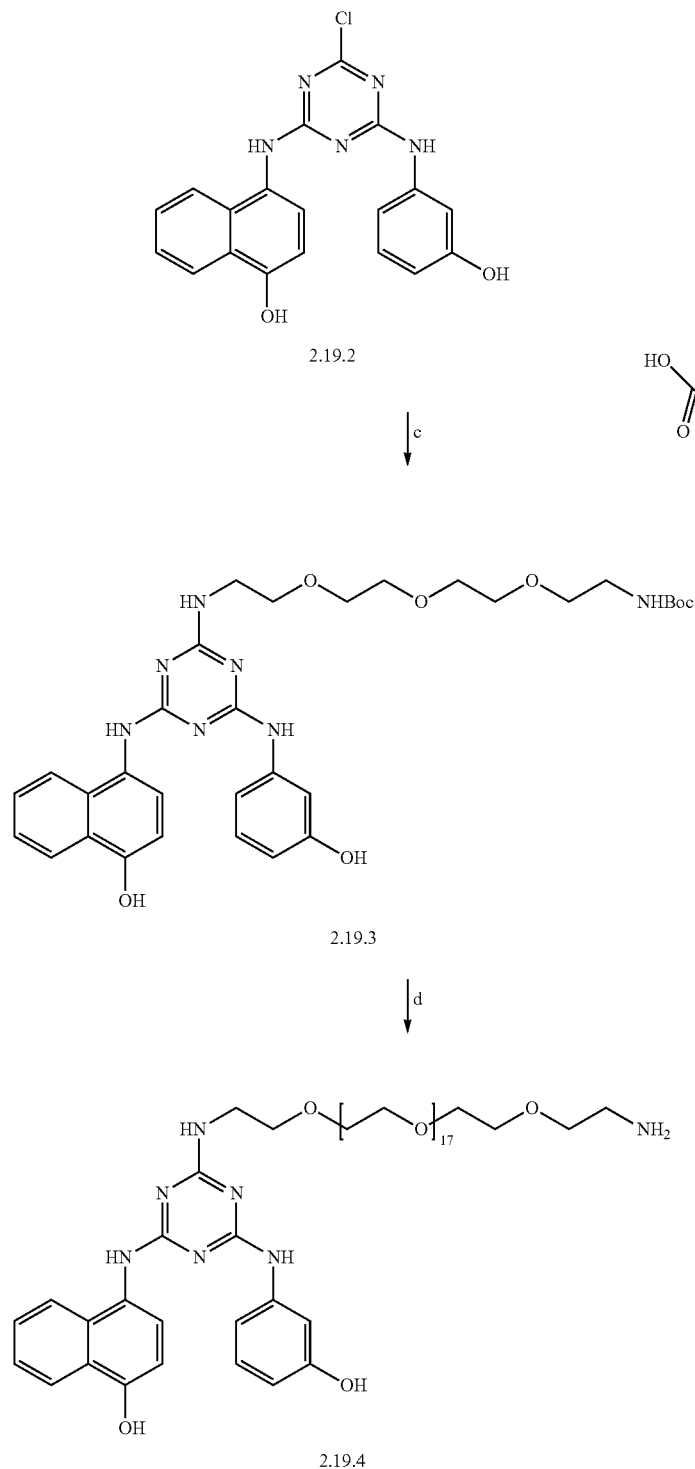
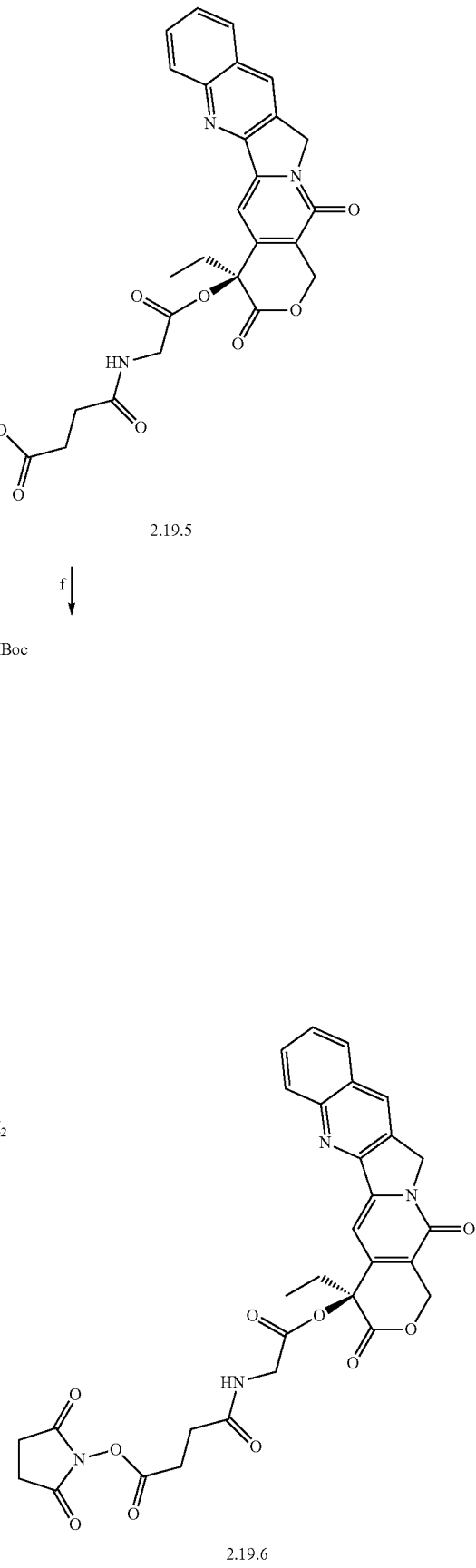

-continued

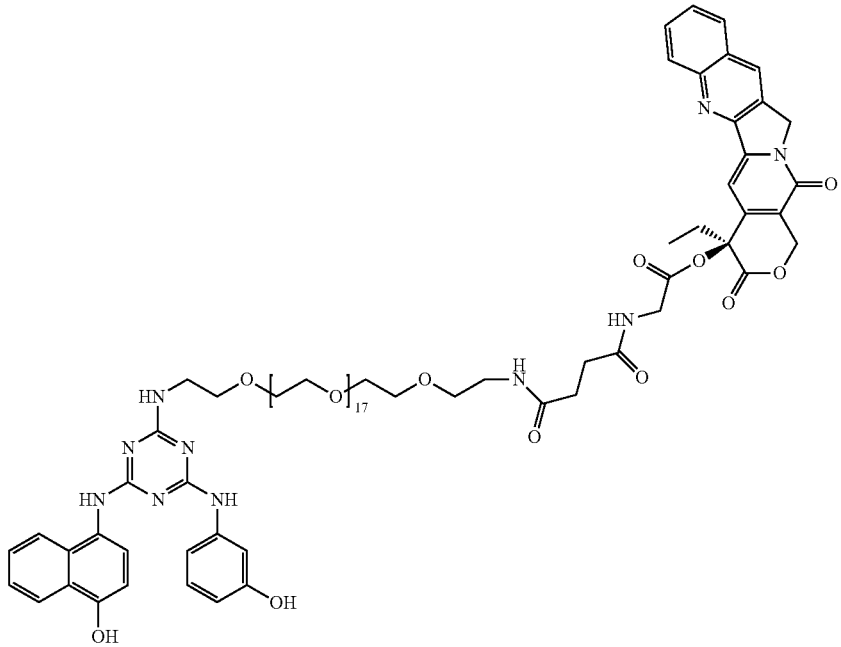

2.19

Reagents and conditions: (a) 3-Amino phenol, NaHCO$_3$, water/acetone, 3 h, 0° C.-rt, (b) 4-Amino-1-naphthol hydrochloride, NaHCO$_3$, water/acetone, 5 h, 45° C., (c) H$_2$NCH$_2$CH$_2$(PEG)$_{18}$CH$_2$CH$_2$NHBoc, DIPEA, THF, 12 h (d) TFA, DCM, 4 h (e) succinic anhydride, DIPEA, CH2Cl2, 12 h (f) NHS, DCC, 6 h, CH2Cl2, 0° C.-rt, 12 h (g) DIPEA, DMF, 12 h.

Step C:
In a 50 mL single neck round bottom flask, Boc-protected PEG-amine is taken in THF (10 mL) under nitrogen atmosphere. To this solution DIPEA is added and stirred for 15 minutes. Intermediate 2.19.2 is added to the reaction mixture and stirred for 12 h. After completion the reaction is quenched by water (20 mL) and extracted with dichloromethane (2×10 mL). The combined organic layer is concentrated and precipitated with diethyl ether (10 mL) to obtain intermediate 2.19.3.

Step D:
In a 100 ml round bottom flask, intermediate 2.19.3 is taken in dry dichloromethane (12 ml) under nitrogen atmosphere and cooled to 0° C. To this solution, TFA (6 ml) is added and stirred for 4 h at room temperature. After completion the reaction mixture is concentrated under vacuum using NaOH trap. The crude intermediate 2.19.4 is directly utilized for next reaction.

Step E:
In a 100 ml round bottom flask, intermediate 2.14.7 is taken in dry dichloromethane (15 ml) under nitrogen atmosphere and cooled to 0° C. To this solution DIPEA (1 mL) followed by succinic anhydride is added and the reaction mixture is stirred for 12 h at room temperature. After completion, the reaction mixture is concentrated on rotary evaporator and purified by silica gel chromatography to obtain intermediate 2.19.5.

Step F:
In a 100 ml round bottom flask, acid intermediate 2.19.5 is taken in dry dichloromethane (15 ml) under nitrogen atmosphere and cooled to 0° C. To this solution NHS and DCC is added and stirred for 12 h at room temperature. After completion, the reaction mixture is concentrated on rotary evaporator and purified by silica gel chromatography to obtain activated ester intermediate 2.19.6.

Step G:
Intermediate 2.19.4 is taken in dry DMF (15 ml) under nitrogen and cooled to 0° C. To this solution DIPEA followed by intermediate 2.19.6 in DMF (5 mL) is added and allowed to stir at room temperature for 12 h. After completion the reaction mixture is quenched with water (50 mL) and extracted with dichloromethane (2×20 mL). The combined organic layer is concentrated and purified by silica gel chromatography to obtain 2.19.

Example 10: Synthesis of 2.20

Figure 28:
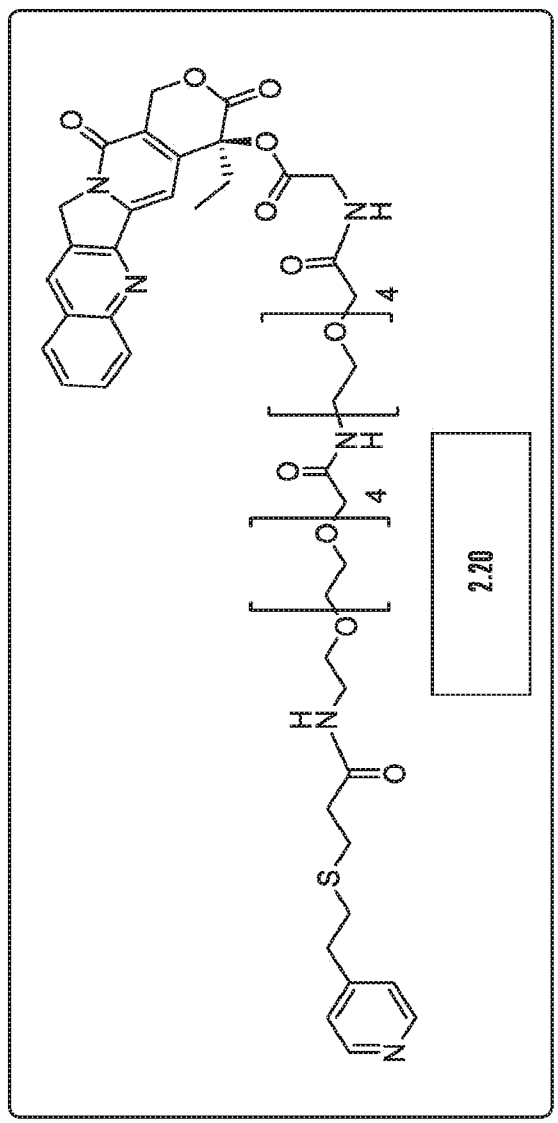
FIG. 28 shows the structure of compound 2.20 where 4-MEP moeity is linked to camptothecin via a cleavable linker.

Conjugate 2.20, shown in FIG. 28, can be synthesized as outlined in Scheme 8.

Step A:
In a 50 mL single neck round bottom flask, t-butyl-ester-protected PEG-azide is taken in dry dichloromethane (10 mL) under nitrogen atmosphere and cooled to 0° C. To this solution TFA (5 mL) is added and stirred for 2 h. After completion the reaction mixture is concentrated under vacuum using NaOH trap. The crude intermediate 2.20.1 is directly utilized for the next reaction.

Scheme 8
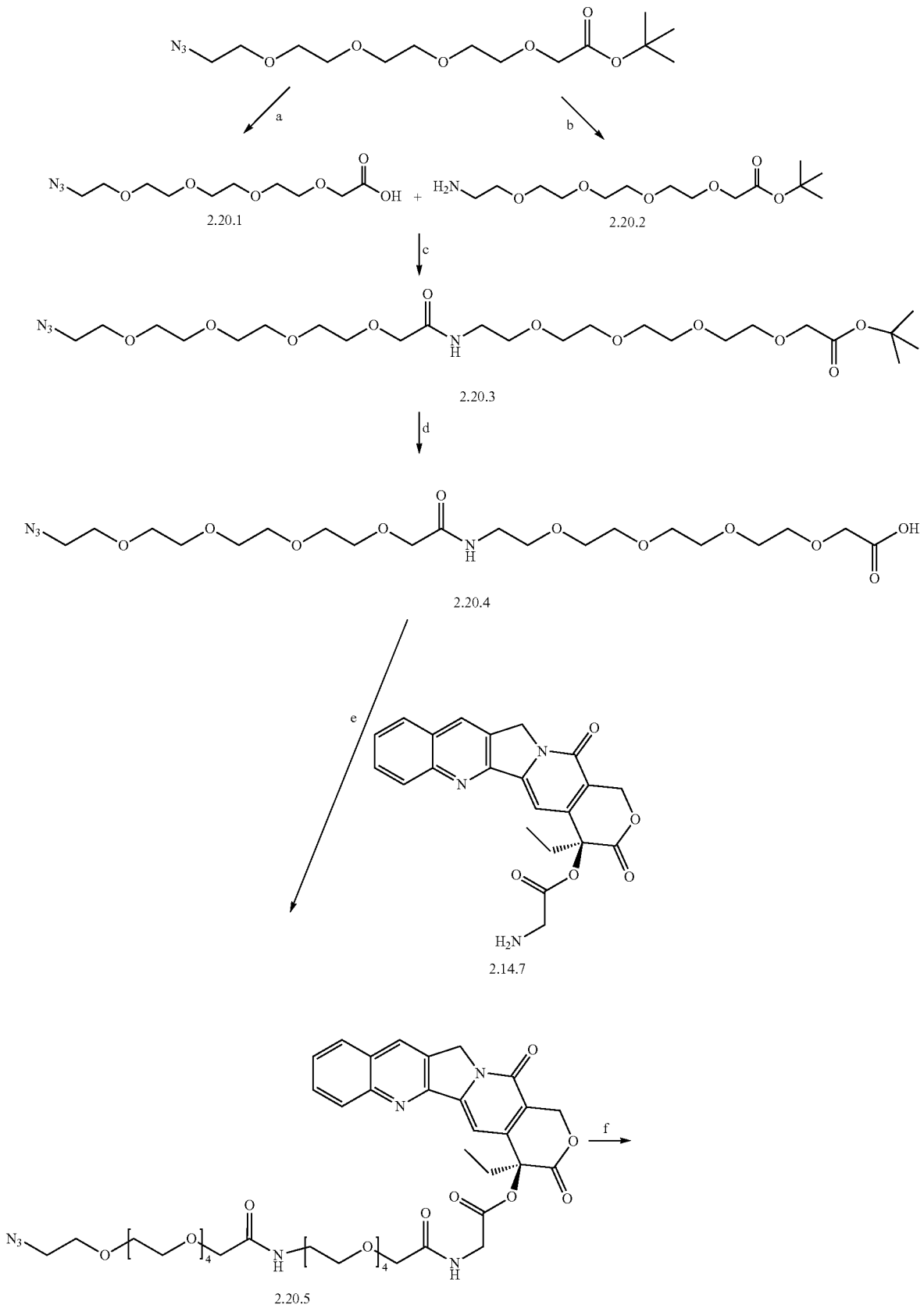

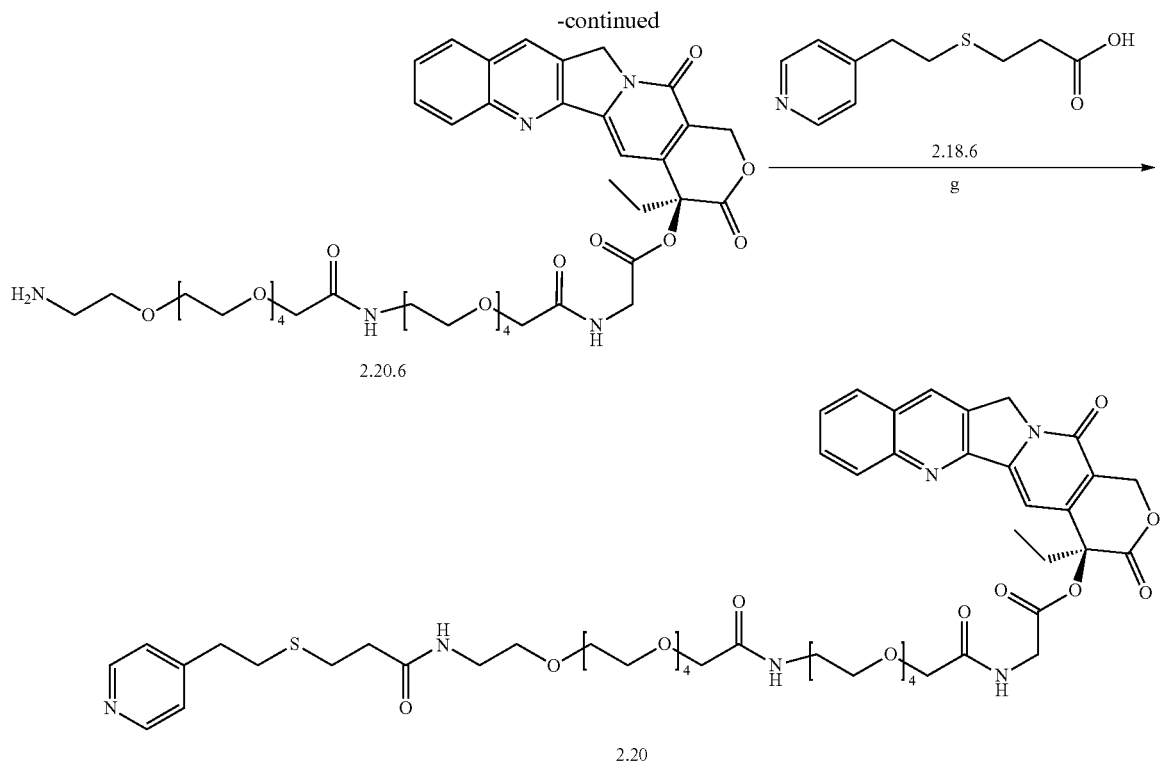

2.20

Reagents and Conditions: (a) TFA, DCM, 0° C., 2 h. (b) Pd/C, formic acid, ethanol, 0° C.-rt, 3 h.
(c) EDCl, HOBT, DIPEA, DCM, 12 h. (d) TFA, DCM, 4 h. (e) EDCl, HOBT, DIPEA, DCM, 12 h.
(f) Pd/C, MeOH, TFA, 1 h. (g) EDCl, HOBT, DIPEA, DCM, 5 h.

Step B:

In a 50 mL single neck round bottom flask, t-butyl-ester-protected PEG-azide is taken in ethanol (10 mL). To the above solution formic acid (1.2 mL) is added dropwise and the solution is warmed. To this solution pinch wise catalytic amount of Pd/C is added until no evolution of gas from the reaction mixture is observed while keeping the reaction mixture at 0° C. The reaction is allowed to stir for 3 h. After completion, the reaction mixture is filtered through thin pad of celite, washed with ethanol (10 mL) and concentrated. The residue is diluted with water, neutralized to pH 7 and extracted with dichloromethane (2×20 mL). The combined organic layer is concentrated under vacuum and the crude intermediate 2.20.2 is directly utilized for the next reaction.

Step C:

In a 100 mL single neck round bottom flask, intermediate 2.20.1 is taken in dry dichloromethane (15 mL) under nitrogen atmosphere and cooled to 0° C. To this ice-cooled solution, EDCI and HOBT are added successively. The reaction mixture is stirred for 30 minutes and then the intermediate 2.20.2 is added. To the reaction mixture DIPEA is added to render the mixture alkaline and the mixture is stirred for 12 h. After completion, the reaction mixture is quenched with water (2×20 mL) and extracted with dichloromethane (2×20 mL). The combined organic layer is concentrated under vacuum and the residue is purified by silica gel chromatography to obtain the intermediate 2.20.3.

Step D:

In a 50 mL single neck round bottom flask, intermediate 2.20.3 is taken in dry dichloromethane (10 ml) under nitrogen atmosphere and cooled to 0° C. To this ice-cooled solution, TFA (5 mL) is added and stirred for 4 h. After completion, the reaction mixture is concentrated under vacuum using NaOH trap and the residue is purified by silica gel chromatography to obtain the intermediate 2.20.4.

Step E:

In a 100 mL single neck round bottom flask, acid intermediate 2.20.4 is taken in dry dichloromethane (10 mL) under nitrogen atmosphere and cooled to 0° C. To this ice-cooled solution EDCI, HOBT and DIPEA are added successively. The reaction mixture is stirred for 30 minutes and the amine intermediate 2.14.7 is added. The reaction mixture is stirred for another 12 h. After completion the reaction mixture is quenched with water (2×50 mL) and extracted with dichloromethane (2×30 mL). The combined organic layer is concentrated under vacuum and the residue is purified by silica gel chromatography to obtain the intermediate 2.20.5.

Step F:

In a 100 mL single neck round bottom flask, intermediate 2.20.5 is taken in methanol (30 mL) and ethyl acetate (10 mL) is added till the solution become clear. To this solution, Palladium-Carbon and TFA (0.5 mL) are added and allowed to stir for 1 h under hydrogen atmosphere. After completion, the reaction is filtered through a thin pad of celite, washed with methanol (10 mL) and concentrated. The residue is precipitated with dichloromethane:diethyl ether (1:10) to obtain the intermediate 2.20.6.

Step G:

In a 100 mL single neck round bottom flask, acid intermediate 2.18.6 is taken in dry dichloromethane (15 mL) under nitrogen atmosphere and cooled to 0° C. To this ice-cooled solution, EDCI, HOBt and DIPEA are added successively. The reaction mixture is stirred for 30 minutes and the amine intermediate 2.20.6 is added. The reaction mixture is stirred for another 5 h. After completion, the reaction mixture is quenched with water (2×20 mL), washed with citric acid solution (5%, 10 mL) and extracted with dichloromethane (2×20 mL). The combined organic layer is concentrated under vacuum and precipitated with diethyl ether (20 mL). The residue is purified by silica gel chromatography to obtain 2.20.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A targeted drug delivery conjugate comprising:
   (i) a targeting ligand;
   (ii) an affinity ligand linked to said targeting ligand, wherein said targeting ligand is an antibody, and wherein said affinity ligand is non-covalently connected to said targeting ligand; and
   (iii) a therapeutic agent linked to said affinity ligand via a linker, and
   wherein the affinity ligand is a triazine,
   wherein the triazine has affinity to the targeting ligand,
   wherein the targeting ligand delivers the therapeutic agent to an antigen expressing cell through affinity binding to triazine,
   wherein the therapeutic agent is an anticancer agent or a cytotoxic drug.

2. The targeted drug delivery conjugate of claim 1, wherein the targeting ligand is a monoclonal antibody.

3. The targeted drug delivery conjugate of claim 1, wherein the linker is a branched linker.

4. A pharmaceutical composition comprising a conjugate of claim 1 and a pharmaceutically acceptable carrier.

* * * * *